United States Patent
Shi et al.

(10) Patent No.: US 11,370,837 B2
(45) Date of Patent: Jun. 28, 2022

(54) ANTI-TIGIT ANTIBODY AND USE THEREOF

(71) Applicant: INNOVENT BIOLOGICS (SUZHOU) CO., LTD., Jiangsu (CN)

(72) Inventors: Xinzhen Shi, Jiangsu (CN); Pan Zhang, Jiangsu (CN); Junjian Liu, Jiangsu (CN)

(73) Assignee: INNOVENT BIOLOGICS (SUZHOU) CO., LTD., Jiangsu (CN)

( * ) Notice: Subject to any disclaimer, the term of this patent is extended or adjusted under 35 U.S.C. 154(b) by 63 days.

(21) Appl. No.: 16/965,687

(22) PCT Filed: Jul. 25, 2019

(86) PCT No.: PCT/CN2019/097665
§ 371 (c)(1),
(2) Date: Jul. 29, 2020

(87) PCT Pub. No.: WO2020/020281
PCT Pub. Date: Jan. 30, 2020

(65) Prior Publication Data
US 2021/0040201 A1    Feb. 11, 2021

(30) Foreign Application Priority Data

Jul. 25, 2018 (CN) .......................... 201810823583.6

(51) Int. Cl.
| | |
|---|---|
| *C07K 16/28* | (2006.01) |
| *A61K 39/395* | (2006.01) |
| *A61P 35/00* | (2006.01) |
| *A61K 47/68* | (2017.01) |
| *C12N 15/63* | (2006.01) |
| *A61K 31/713* | (2006.01) |
| *G01N 33/53* | (2006.01) |
| *A61P 31/12* | (2006.01) |
| *A61P 37/04* | (2006.01) |
| *C07K 14/705* | (2006.01) |
| *A61K 45/06* | (2006.01) |

(52) U.S. Cl.
CPC ............ *C07K 16/28* (2013.01); *A61K 31/713* (2013.01); *A61K 39/3955* (2013.01); *A61K 47/6849* (2017.08); *A61P 31/12* (2018.01); *A61P 37/04* (2018.01); *C07K 16/2803* (2013.01); *C12N 15/63* (2013.01); *G01N 33/53* (2013.01); *A61K 45/06* (2013.01); *C07K 14/705* (2013.01); *C07K 14/70503* (2013.01); *C07K 2317/31* (2013.01); *C07K 2317/565* (2013.01); *C07K 2317/73* (2013.01)

(58) Field of Classification Search
CPC .............. C07K 14/705; C07K 14/70503; C07K 16/28; C07K 16/2083; A61K 39/395; A61K 39/3955; A61P 31/00; A61P 35/00; A61P 37/02; A61P 31/12; A61P 37/04
See application file for complete search history.

(56) References Cited

U.S. PATENT DOCUMENTS

| | | | |
|---|---|---|---|
| 5,648,237 | A | 7/1997 | Carter |
| 5,677,425 | A | 10/1997 | Bodmer et al. |
| 5,760,185 | A | 6/1998 | Kimachi et al. |
| 5,762,905 | A | 6/1998 | Burton et al. |
| 5,789,199 | A | 8/1998 | Joly et al. |
| 5,833,943 | A | 11/1998 | Courtenay-Luck |
| 5,840,523 | A | 11/1998 | Simmons et al. |
| 6,090,382 | A | 7/2000 | Salfeld et al. |
| 6,156,313 | A | 12/2000 | Burton et al. |
| 6,171,586 | B1 | 1/2001 | Lam et al. |
| 6,194,551 | B1 | 2/2001 | Idusogie et al. |
| 6,818,216 | B2 | 11/2004 | Young et al. |
| 6,827,925 | B1 | 12/2004 | Williams et al. |
| 6,914,128 | B1 | 7/2005 | Salfeld et al. |
| 6,951,646 | B1 | 10/2005 | Reiter et al. |

FOREIGN PATENT DOCUMENTS

| | | |
|---|---|---|
| CN | 107148430 A | 9/2017 |
| CN | 107207594 A | 9/2017 |
| CN | 108137691 A | 6/2018 |
| CN | 108290936 A | 7/2018 |
| EP | 0154316 A2 | 9/1985 |
| EP | 0401384 A1 | 12/1990 |
| RU | 2732591 C2 | 9/2020 |
| TW | 201718636 A | 6/2017 |
| TW | 201734043 A | 10/2017 |
| WO | 99/51642 A1 | 10/1999 |
| WO | 2006/004490 A1 | 1/2006 |

(Continued)

OTHER PUBLICATIONS

Solomon et al, 2018. Cancer Immunology, Immunotherapy. 67: 1659-1667.*
Chauvin, Joe-Marc, et al. "TIGIT and PD-1 impair tumor antigen-specific CD8+ T cells in melanoma patients." The Journal of clinical investigation 125.5 (2015): 2046-2058.
Estep, Patricia, et al. "High throughput solution-based measurement of antibody-antigen affinity and epitope binning." MAbs. vol. 5. No. 2 Taylor & Francis, 2013.
Gemgross, Tillman U. "Advances in the production of human therapeutic proteins in yeasts and filamentous fungi." Nature biotechnology 22.11 (2004): 1409-1414.

(Continued)

*Primary Examiner* — Zachary C Howard
(74) *Attorney, Agent, or Firm* — Leason Ellis LLP

(57) ABSTRACT

The present invention relates to a novel antibody and an antibody fragment thereof that specifically bind to TIGIT and a composition comprising the antibody or the antibody fragment. In addition, the present invention relates to a nucleic acid encoding the antibody or the antibody fragment thereof, a host cell comprising the nucleic acid, and related use. Furthermore, the present invention relates to therapeutic and diagnostic use of the antibody and the antibody fragment.

22 Claims, 13 Drawing Sheets
Specification includes a Sequence Listing.

(56) References Cited

FOREIGN PATENT DOCUMENTS

| WO | 2006044908 | A2 | 4/2006 |
|---|---|---|---|
| WO | 2009/036379 | A2 | 3/2009 |
| WO | 2009/080251 | A1 | 7/2009 |
| WO | 2009/080252 | A1 | 7/2009 |
| WO | 2009/080253 | A1 | 7/2009 |
| WO | 2009/080254 | A1 | 7/2009 |
| WO | 2010/105256 | A1 | 9/2010 |
| WO | 2010/112193 | A1 | 10/2010 |
| WO | 2010/115589 | A1 | 10/2010 |
| WO | 2010/136172 | A1 | 12/2010 |
| WO | 2010/145792 | A1 | 12/2010 |
| WO | 2010/145793 | A1 | 12/2010 |
| WO | 2012/009568 | A2 | 1/2012 |
| WO | 2015/009856 | A2 | 1/2015 |
| WO | 2015/153513 | A1 | 10/2015 |
| WO | 2016/028656 | A1 | 2/2016 |
| WO | 2016/106302 | A1 | 6/2016 |
| WO | 2016/191643 | A2 | 12/2016 |
| WO | 2017/025016 | A1 | 2/2017 |
| WO | 2017/053748 | A2 | 3/2017 |
| WO | 2017/059095 | A1 | 4/2017 |
| WO | 2017/133540 | A1 | 8/2017 |
| WO | 2017/152088 | A1 | 9/2017 |

OTHER PUBLICATIONS

Li, Huijuan, et al. "Optimization of humanized IgGs in glycoengineered Pichia pastoris." Nature biotechnology 24.2 (2006): 210-215.
Graham, Frank L., et al. "Characteristics of a human cell line transformed by DNA from human adenovirus type 5." Journal of general virology 36.1 (1977): 59-72.
Urlaub, Gail et al., "Isolation of Chinese hamster cell mutants deficient in dihydrofolate reductase activity." Proceedings of the National Academy of Sciences 77.7 (1980): 4216-4220.
Idusogie, Esohe E., et al. "Mapping of the C1q binding site on rituxan, a chimeric antibody with a human IgG1 Fc." The Journal of Immunology 164.8 (2000): 4178-4184.
Hudson, Peter J., and Christelle Souriau. "Engineered antibodies." Nature medicine 9.1 (2003): 129-134.
Chothia, Cyrus, and Arthur M. Lesk. "Canonical structures for the hypervariable regions of immunoglobulins." Journal of molecular biology 196.4 (1987): 901-917.
Clackson, Tim, et al. "Making antibody fragments using phage display libraries." Nature 352.6336 (1991): 624-628.
Gao, Y., "Generation and Characterization of Polyclonal Antibodies against Mouse TIGIT by DNA-Base Immunization", A Dissertation Submitted to Huazhong University of Science and Technology for the Degree of Master of Medicine, May 2013.
Hollinger et al., "Diabodies: Small bivalent and bispecific antibody fragments": PNAS USA 90:6444-6448 (1993).
Grogan et al. (2014) J. Immunol. 192(1) Suppl. 203.15.
Inozume et al. (2014) J. Invest. Dermatol. 134:S121—Abstract 693.
Johnston et al. "The Immunoreceptor TIGIT Regulates Antitumor and Antiviral CD8+ T Cell effector Function" (2014) Cancer Cell 26:1-15.
Flatman, Stephen, et al. "Process analytics for purification of monoclonal antibodies." Journal of Chromatography B 848.1 (2007): 79-87.
Portolano, Stefano, et al. "Lack of promiscuity in autoantigen-specific H and L chain combinations as revealed by human H and L chain" roulette"." The Journal of Immunology 150.3 (1993): 880-887.
Manieri, Nicholas A., Eugene Y. Chiang, and Jane L. Grogan. "TIGIT: a key inhibitor of the cancer immunity cycle." Trends in immunology 38.1 (2017): 20-28.
International Search Report and Written Opinion in Corresponding PCT Application No. PCT/CN2019/097605 dated Oct. 29, 2019.

* cited by examiner

Human TIGIT sequence

MRWCLLLIWAQGLRQAPLASGMMTGTIETTGNISAEKGGSIILQCHLSSTTAQVTQVNWEQQDQLLAICNADLGWHISPSFKDR

VAPGPGLGLTLQSLTVNDTGEYFCIYHTYPDGTYTGRIFLEVLESSVAEHGARFQIPLLGAMAATLVVICTAVIVVVALTRKKKALRIHS

VEGDLRRKSAGQEEWSPSAPSPPGSCVQAEAAPAGLCGEQRGEDCAELHDYFNVLSYRSLGNCSFFTETG (SEQ ID NO: 208)

FIG. 9

SEQUENCE LISTING

```
<160> NUMBER OF SEQ ID NOS: 209

<210> SEQ ID NO 1
<211> LENGTH: 9
<212> TYPE: PRT
<213> ORGANISM: artificial sequence
<220> FEATURE:
<223> OTHER INFORMATION: Antibody Sequence 1 ADI-27238 HCDR1 KABAT
      numbering positions H27-35B

<400> SEQUENCE: 1

Tyr Thr Phe Thr Ser Tyr Tyr Met Ser
1               5

<210> SEQ ID NO 2
<211> LENGTH: 9
<212> TYPE: PRT
<213> ORGANISM: artificial sequence
<220> FEATURE:
<223> OTHER INFORMATION: Antibody Sequence 2 ADI-30263 HCDR1 KABAT
      numbering positions H27-35B

<400> SEQUENCE: 2

Tyr Thr Phe Leu Ser Tyr Tyr Met Asn
1               5

<210> SEQ ID NO 3
<211> LENGTH: 9
<212> TYPE: PRT
<213> ORGANISM: artificial sequence
<220> FEATURE:
<223> OTHER INFORMATION: Antibody Sequence 3 ADI-30267 HCDR1 KABAT
      numbering positions H27-35B

<400> SEQUENCE: 3
```

```
Tyr Thr Phe Arg Ser Tyr Tyr Met Ser
1               5
```

<210> SEQ ID NO 4
<211> LENGTH: 9
<212> TYPE: PRT
<213> ORGANISM: artificial sequence
<220> FEATURE:
<223> OTHER INFORMATION: Antibody Sequence 4 ADI-30268 HCDR1 KABAT
      numbering positions H27-35B

<400> SEQUENCE: 4

```
Tyr Thr Phe Gly Ser Tyr Tyr Met Gly
1               5
```

<210> SEQ ID NO 5
<211> LENGTH: 9
<212> TYPE: PRT
<213> ORGANISM: artificial sequence
<220> FEATURE:
<223> OTHER INFORMATION: Antibody Sequence 5 Consensus sequence
<220> FEATURE:
<221> NAME/KEY: misc_feature
<222> LOCATION: (4)..(4)
<223> OTHER INFORMATION: Xaa may be any natural amino acid, preferably
      selected from T, L, R, G and a conservatively substituted residue
      thereof
<220> FEATURE:
<221> NAME/KEY: misc_feature
<222> LOCATION: (9)..(9)
<223> OTHER INFORMATION: Xaa may be any natural amino acid, preferably
      selected from S, N, G and a conservatively substituted residue
      thereof

<400> SEQUENCE: 5

```
Tyr Thr Phe Xaa Ser Tyr Tyr Met Xaa
1               5
```

<210> SEQ ID NO 6
<211> LENGTH: 17
<212> TYPE: PRT
<213> ORGANISM: artificial sequence
<220> FEATURE:
<223> OTHER INFORMATION: Antibody Sequence 6 ADI-27238, ADI-27297 HCDR2
      KABAT numbering positions H50-65

<400> SEQUENCE: 6

```
Ile Ile Asn Pro Ser Gly Gly Ser Thr Ser Tyr Ala Gln Lys Phe Gln
1               5                   10                  15

Gly
```

<210> SEQ ID NO 7
<211> LENGTH: 17
<212> TYPE: PRT
<213> ORGANISM: artificial sequence
<220> FEATURE:
<223> OTHER INFORMATION: Antibody Sequence 7 ADI-30263 HCDR2 KABAT
      H50-65

<400> SEQUENCE: 7

```
Ile Ile Asp Pro Ser Gly Gly Arg Thr Ser Tyr Ala Gln Lys Phe Gln
1               5                   10                  15

Gly
```

<210> SEQ ID NO 8
<211> LENGTH: 17
<212> TYPE: PRT
<213> ORGANISM: artificial sequence

```
<220> FEATURE:
<223> OTHER INFORMATION: Antibody Sequence 8 ADI-30267 HCDR2 KABAT
      H50-65

<400> SEQUENCE: 8

Ile Ile Asp Pro Ser Gly Gly Arg Thr Ser Phe Ala Gln Lys Phe Gln
1               5                   10                  15

Gly

<210> SEQ ID NO 9
<211> LENGTH: 17
<212> TYPE: PRT
<213> ORGANISM: artificial sequence
<220> FEATURE:
<223> OTHER INFORMATION: Antibody Sequence 9 ADI-30268 HCDR2 KABAT
      H50-65

<400> SEQUENCE: 9

Ile Ile Asp Pro Ser Gly Gly Arg Thr Ser Tyr Ala Arg Lys Phe Gln
1               5                   10                  15

Gly

<210> SEQ ID NO 10
<211> LENGTH: 17
<212> TYPE: PRT
<213> ORGANISM: artificial sequence
<220> FEATURE:
<223> OTHER INFORMATION: Antibody Sequence 10 Consensus sequence
<220> FEATURE:
<221> NAME/KEY: misc_feature
<222> LOCATION: (3)..(3)
<223> OTHER INFORMATION: Xaa may be any natural amino acid, preferably
      selected from N, D and a conservatively substituted residue
      thereof
<220> FEATURE:
<221> NAME/KEY: misc_feature
<222> LOCATION: (8)..(8)
<223> OTHER INFORMATION: Xaa may be any natural amino acid, preferably
      selected from S, R and a conservatively substituted residue
      thereof
<220> FEATURE:
<221> NAME/KEY: misc_feature
<222> LOCATION: (11)..(11)
<223> OTHER INFORMATION: Xaa may be any natural amino acid, preferably
      selected from Y, F and a conservatively substituted residue
      thereof
<220> FEATURE:
<221> NAME/KEY: misc_feature
<222> LOCATION: (13)..(13)
<223> OTHER INFORMATION: Xaa may be any natural amino acid, preferably
      selected from Q, R and a conservatively substituted residue
      thereof

<400> SEQUENCE: 10

Ile Ile Xaa Pro Ser Gly Gly Xaa Thr Ser Xaa Ala Xaa Lys Phe Gln
1               5                   10                  15

Gly

<210> SEQ ID NO 11
<211> LENGTH: 15
<212> TYPE: PRT
<213> ORGANISM: artificial sequence
<220> FEATURE:
<223> OTHER INFORMATION: Antibody Sequence 11 ADI-27238 HCDR3 Kabat
      H93-102

<400> SEQUENCE: 11

Ala Arg Ala Arg Tyr Pro Ser Ser Trp Pro Tyr Gly Met Asp Val
1               5                   10                  15
```

```
<210> SEQ ID NO 12
<211> LENGTH: 15
<212> TYPE: PRT
<213> ORGANISM: artificial sequence
<220> FEATURE:
<223> OTHER INFORMATION: Antibody Sequence 12 ADI-30263 HCDR3 Kabat
      H93-102

<400> SEQUENCE: 12

Ala Arg Ala Arg Tyr Pro Ser Ser Trp Pro Tyr Gly Thr Asp Val
1               5                   10                  15

<210> SEQ ID NO 13
<211> LENGTH: 15
<212> TYPE: PRT
<213> ORGANISM: artificial sequence
<220> FEATURE:
<223> OTHER INFORMATION: Antibody Sequence 13 ADI-30267 HCDR3 Kabat
      H93-102

<400> SEQUENCE: 13

Ala Arg Ala Arg Tyr Pro Glu Ser Trp Pro Tyr Gly Met Asp Val
1               5                   10                  15

<210> SEQ ID NO 14
<211> LENGTH: 15
<212> TYPE: PRT
<213> ORGANISM: artificial sequence
<220> FEATURE:
<223> OTHER INFORMATION: Antibody Sequence 14 ADI-30268 HCDR3 Kabat
      H93-102

<400> SEQUENCE: 14

Ala Arg Ala Arg Thr Pro Ser Ser Trp Pro Tyr Gly Met Asp Val
1               5                   10                  15

<210> SEQ ID NO 15
<211> LENGTH: 15
<212> TYPE: PRT
<213> ORGANISM: artificial sequence
<220> FEATURE:
<223> OTHER INFORMATION: Antibody Sequence 15 Consensus sequence
<220> FEATURE:
<221> NAME/KEY: misc_feature
<222> LOCATION: (5)..(5)
<223> OTHER INFORMATION: Xaa may be any natural amino acid, preferably
      selected from Y, T and a conservatively substituted residue
      thereof
<220> FEATURE:
<221> NAME/KEY: misc_feature
<222> LOCATION: (13)..(13)
<223> OTHER INFORMATION: Xaa may be any natural amino acid, preferably
      selected from M, T and a conservatively substituted residue
      thereof

<400> SEQUENCE: 15

Ala Arg Ala Arg Xaa Pro Ser Ser Trp Pro Tyr Gly Xaa Asp Val
1               5                   10                  15

<210> SEQ ID NO 16
<211> LENGTH: 11
<212> TYPE: PRT
<213> ORGANISM: artificial sequence
<220> FEATURE:
<223> OTHER INFORMATION: Antibody Sequence 16 ADI-27238, ADI-30263,
      ADI-30267, ADI-30268 LCDR1 Kabat L24-34

<400> SEQUENCE: 16
```

Arg Ala Ser Gln Ser Ile Asn Ser Tyr Leu Asn
1               5                   10

<210> SEQ ID NO 17
<211> LENGTH: 7
<212> TYPE: PRT
<213> ORGANISM: artificial sequence
<220> FEATURE:
<223> OTHER INFORMATION: Antibody Sequence 17 ADI-27238, ADI-30263,
      ADI-30267, ADI-30268, ADI-27297, ADI-30272, ADI-30272 LCDR
2 Kabat L50-56

<400> SEQUENCE: 17

Ala Ala Ser Ser Leu Gln Ser
1               5

<210> SEQ ID NO 18
<211> LENGTH: 9
<212> TYPE: PRT
<213> ORGANISM: artificial sequence
<220> FEATURE:
<223> OTHER INFORMATION: Antibody Sequence 18 ADI-27238, ADI-30263,
      ADI-30267, ADI-30268 LCDR3 Kabat L89-97

<400> SEQUENCE: 18

Gln Gln Ser Leu Leu Thr Pro Phe Thr
1               5

<210> SEQ ID NO 19
<211> LENGTH: 11
<212> TYPE: PRT
<213> ORGANISM: artificial sequence
<220> FEATURE:
<223> OTHER INFORMATION: Antibody Sequence 19 ADI-27243, ADI-30336 HCDR1
      KABAT numbering positions H27-35B

<400> SEQUENCE: 19

Gly Ser Ile Ser Ser Ser Arg Tyr Tyr Trp Gly
1               5                   10

<210> SEQ ID NO 20
<211> LENGTH: 11
<212> TYPE: PRT
<213> ORGANISM: artificial sequence
<220> FEATURE:
<223> OTHER INFORMATION: Antibody Sequence 20 ADI-30302 HCDR1 KABAT
      numbering positions H27-35B

<400> SEQUENCE: 20

Gly Ser Ile Gly Ser Ser Gln Tyr Tyr Trp Gly
1               5                   10

<210> SEQ ID NO 21
<211> LENGTH: 11
<212> TYPE: PRT
<213> ORGANISM: artificial sequence
<220> FEATURE:
<223> OTHER INFORMATION: Antibody Sequence 21 Consensus sequence
<220> FEATURE:
<221> NAME/KEY: misc_feature
<222> LOCATION: (4)..(4)
<223> OTHER INFORMATION: Xaa may be any natural amino acid, preferably
      selected from S, G and a conservatively substituted residue
      thereof
<220> FEATURE:
<221> NAME/KEY: misc_feature
<222> LOCATION: (7)..(7)
<223> OTHER INFORMATION: Xaa may be any natural amino acid, preferably
      selected from R, Q and a conservatively substituted residue
      thereof

```
<400> SEQUENCE: 21

Gly Ser Ile Xaa Ser Ser Xaa Tyr Tyr Trp Gly
1               5                   10

<210> SEQ ID NO 22
<211> LENGTH: 16
<212> TYPE: PRT
<213> ORGANISM: artificial sequence
<220> FEATURE:
<223> OTHER INFORMATION: Antibody Sequence 22 ADI-27243, ADI-30336,
      ADI-27301 HCDR2 KABAT H50-65

<400> SEQUENCE: 22

Ser Ile Tyr Tyr Ser Gly Ser Thr Tyr Tyr Asn Pro Ser Leu Lys Ser
1               5                   10                  15

<210> SEQ ID NO 23
<211> LENGTH: 16
<212> TYPE: PRT
<213> ORGANISM: artificial sequence
<220> FEATURE:
<223> OTHER INFORMATION: Antibody Sequence 23 ADI-30302 HCDR2 KABAT
      H50-65

<400> SEQUENCE: 23

Ser Ile Tyr Arg Ser Gly Gly Thr Tyr Tyr Asn Pro Ser Leu Lys Ser
1               5                   10                  15

<210> SEQ ID NO 24
<211> LENGTH: 16
<212> TYPE: PRT
<213> ORGANISM: artificial sequence
<220> FEATURE:
<223> OTHER INFORMATION: Antibody Sequence 24 Consensus sequence
<220> FEATURE:
<221> NAME/KEY: misc_feature
<222> LOCATION: (4)..(4)
<223> OTHER INFORMATION: Xaa may be any natural amino acid, preferably
      selected from Y, R and a conservatively substituted residue
      thereof
<220> FEATURE:
<221> NAME/KEY: misc_feature
<222> LOCATION: (7)..(7)
<223> OTHER INFORMATION: Xaa may be any natural amino acid, preferably
      selected from S, G and a conservatively substituted residue
      thereof

<400> SEQUENCE: 24

Ser Ile Tyr Xaa Ser Gly Xaa Thr Tyr Tyr Asn Pro Ser Leu Lys Ser
1               5                   10                  15

<210> SEQ ID NO 25
<211> LENGTH: 14
<212> TYPE: PRT
<213> ORGANISM: artificial sequence
<220> FEATURE:
<223> OTHER INFORMATION: Antibody Sequence 25 ADI-27243, ADI-30302,
      ADI-30336 HCDR3 Kabat H93-102

<400> SEQUENCE: 25

Ala Arg Asp Gly Leu Tyr His Thr Pro Glu Tyr Phe Gln His
1               5                   10

<210> SEQ ID NO 26
<211> LENGTH: 11
<212> TYPE: PRT
<213> ORGANISM: artificial sequence
<220> FEATURE:
```

```
<223> OTHER INFORMATION: Antibody Sequence 26 ADI-27243, ADI-30302,
     ADI-30336 LCDR1 Kabat L24-34

<400> SEQUENCE: 26

Arg Ala Ser Gln Ser Val Ser Ser Tyr Leu Ala
1               5                   10

<210> SEQ ID NO 27
<211> LENGTH: 7
<212> TYPE: PRT
<213> ORGANISM: artificial sequence
<220> FEATURE:
<223> OTHER INFORMATION: Antibody Sequence 27 ADI-27243, ADI-30302,
     ADI-30336 LCDR2 Kabat L50-56

<400> SEQUENCE: 27

Asp Ala Ser Asn Arg Ala Thr
1               5

<210> SEQ ID NO 28
<211> LENGTH: 9
<212> TYPE: PRT
<213> ORGANISM: artificial sequence
<220> FEATURE:
<223> OTHER INFORMATION: Antibody Sequence 28 ADI-27243, ADI-30302 LCDR3
     Kabat L89-97

<400> SEQUENCE: 28

Gln Gln Arg Phe Ala Phe Pro Tyr Thr
1               5

<210> SEQ ID NO 29
<211> LENGTH: 9
<212> TYPE: PRT
<213> ORGANISM: artificial sequence
<220> FEATURE:
<223> OTHER INFORMATION: Antibody Sequence 29 ADI-30336 LCDR3 Kabat
     L89-97

<400> SEQUENCE: 29

Gln Gln Arg Phe Ala His Pro Tyr Thr
1               5

<210> SEQ ID NO 30
<211> LENGTH: 9
<212> TYPE: PRT
<213> ORGANISM: artificial sequence
<220> FEATURE:
<223> OTHER INFORMATION: Antibody Sequence 30 Consensus sequence
<220> FEATURE:
<221> NAME/KEY: misc_feature
<222> LOCATION: (6)..(6)
<223> OTHER INFORMATION: Xaa may be any natural amino acid, preferably
     selected from F, H and a conservatively substituted residue
     thereof

<400> SEQUENCE: 30

Gln Gln Arg Phe Ala Xaa Pro Tyr Thr
1               5

<210> SEQ ID NO 31
<211> LENGTH: 9
<212> TYPE: PRT
<213> ORGANISM: artificial sequence
<220> FEATURE:
<223> OTHER INFORMATION: Antibody Sequence 31 ADI-27278, ADI-30293 HCDR1
     KABAT numbering positions H27-35B

<400> SEQUENCE: 31
```

```
Phe Thr Phe Ser Ser Tyr Ser Met Asn
1               5
```

```
<210> SEQ ID NO 32
<211> LENGTH: 9
<212> TYPE: PRT
<213> ORGANISM: artificial sequence
<220> FEATURE:
<223> OTHER INFORMATION: Antibody Sequence 32 ADI-30296 HCDR1 KABAT
      numbering positions H27-35B

<400> SEQUENCE: 32
```

```
Phe Thr Ile Gly Gly Tyr Ser Met Asn
1               5
```

```
<210> SEQ ID NO 33
<211> LENGTH: 9
<212> TYPE: PRT
<213> ORGANISM: artificial sequence
<220> FEATURE:
<223> OTHER INFORMATION: Antibody Sequence 33 Consensus sequence
<220> FEATURE:
<221> NAME/KEY: misc_feature
<222> LOCATION: (3)..(5)
<223> OTHER INFORMATION: Xaa may be any natural amino acid, and
      preferably, Xaa at position 3 is selected from F, I and a
      conservatively substituted residue thereof, Xaa at position 4 is
      selected from S, G and a conservatively substituted residue
      thereof, and Xaa at position 5 is selected from S, G and a
      conservatively substituted residue thereof

<400> SEQUENCE: 33
```

```
Phe Thr Xaa Xaa Xaa Tyr Ser Met Asn
1               5
```

```
<210> SEQ ID NO 34
<211> LENGTH: 17
<212> TYPE: PRT
<213> ORGANISM: artificial sequence
<220> FEATURE:
<223> OTHER INFORMATION: Antibody Sequence 34 ADI-27278 HCDR2 KABAT
      H50-65

<400> SEQUENCE: 34
```

```
Tyr Ile Ser Gly Ser Ser Ser Thr Ile Tyr Tyr Ala Asp Ser Val Lys
1               5                   10                  15

Gly
```

```
<210> SEQ ID NO 35
<211> LENGTH: 16
<212> TYPE: PRT
<213> ORGANISM: artificial sequence
<220> FEATURE:
<223> OTHER INFORMATION: Antibody Sequence 35 ADI-30293 HCDR2 KABAT
      H50-65

<400> SEQUENCE: 35
```

```
Tyr Ile Ser Ser Ser Gly Thr Ile Asn Tyr Ala Asp Ser Val Lys Gly
1               5                   10                  15
```

```
<210> SEQ ID NO 36
<211> LENGTH: 16
<212> TYPE: PRT
<213> ORGANISM: artificial sequence
<220> FEATURE:
<223> OTHER INFORMATION: Antibody Sequence 36 ADI-30296 HCDR2 KABAT
      H50-65
```

-continued

```
<400> SEQUENCE: 36

Tyr Ile Ser Ser Ser Ser Thr Ile His Tyr Ala Asp Ser Val Lys Gly
1               5                   10                  15

<210> SEQ ID NO 37
<211> LENGTH: 17
<212> TYPE: PRT
<213> ORGANISM: artificial sequence
<220> FEATURE:
<223> OTHER INFORMATION: Antibody Sequence 37 Consensus sequence
<220> FEATURE:
<221> NAME/KEY: misc_feature
<222> LOCATION: (3)..(4)
<223> OTHER INFORMATION: Xaa may be any natural amino acid, and
      preferably, Xaa at position 3 is selected from deletion, S and a
      conservatively substituted residue thereof, and Xaa at position 4
      is selected from G, S and a conservatively substituted residue
      thereof
<220> FEATURE:
<221> NAME/KEY: misc_feature
<222> LOCATION: (7)..(7)
<223> OTHER INFORMATION: Xaa may be any natural amino acid, preferably
      selected from S, G and a conservatively substituted residue
      thereof
<220> FEATURE:
<221> NAME/KEY: misc_feature
<222> LOCATION: (10)..(10)
<223> OTHER INFORMATION: Xaa may be any natural amino acid, preferably
      selected from Y, N, H and a conservatively substituted residue
      thereof

<400> SEQUENCE: 37

Tyr Ile Xaa Xaa Ser Ser Xaa Thr Ile Xaa Tyr Ala Asp Ser Val Lys
1               5                   10                  15

Gly

<210> SEQ ID NO 38
<211> LENGTH: 15
<212> TYPE: PRT
<213> ORGANISM: artificial sequence
<220> FEATURE:
<223> OTHER INFORMATION: Antibody Sequence 38 ADI-27278, ADI-30293 HCDR3
      Kabat H93-102

<400> SEQUENCE: 38

Ala Arg His Arg Ile Ala Asp Ser Pro Ser Arg Ala Phe Asp Ile
1               5                   10                  15

<210> SEQ ID NO 39
<211> LENGTH: 15
<212> TYPE: PRT
<213> ORGANISM: artificial sequence
<220> FEATURE:
<223> OTHER INFORMATION: Antibody Sequence 39 ADI-30296 HCDR3 Kabat
      H93-102

<400> SEQUENCE: 39

Ala Arg His Arg Ile Gly Arg Ser Pro Ser Arg Ala Phe Asp Ile
1               5                   10                  15

<210> SEQ ID NO 40
<211> LENGTH: 15
<212> TYPE: PRT
<213> ORGANISM: artificial sequence
<220> FEATURE:
<223> OTHER INFORMATION: Antibody Sequence 40 Consensus sequence
<220> FEATURE:
<221> NAME/KEY: misc_feature
<222> LOCATION: (6)..(7)
<223> OTHER INFORMATION: Xaa may be any natural amino acid, and
``` preferably, Xaa at position 6 is selected from A, G and a
conservatively substituted residue thereof, and Xaa at position 7
is selected from D, R and a conservatively substituted residue
thereof

<400> SEQUENCE: 40

Ala Arg His Arg Ile Xaa Xaa Ser Pro Ser Arg Ala Phe Asp Ile
1               5                   10                  15

<210> SEQ ID NO 41
<211> LENGTH: 17
<212> TYPE: PRT
<213> ORGANISM: artificial sequence
<220> FEATURE:
<223> OTHER INFORMATION: Antibody Sequence 41 ADI-27278, ADI-30293,
      ADI-30296 LCDR1-Kabat L24-34

<400> SEQUENCE: 41

Lys Ser Ser Gln Ser Val Leu Phe Ser Ser Asn Asn Lys Asn Tyr Leu
1               5                   10                  15

Ala

<210> SEQ ID NO 42
<211> LENGTH: 7
<212> TYPE: PRT
<213> ORGANISM: artificial sequence
<220> FEATURE:
<223> OTHER INFORMATION: Antibody Sequence 42 ADI-27278, ADI-30293,
      ADI-30296 LCDR2-Kabat L50-56

<400> SEQUENCE: 42

Trp Ala Ser Thr Arg Glu Ser
1               5

<210> SEQ ID NO 43
<211> LENGTH: 8
<212> TYPE: PRT
<213> ORGANISM: artificial sequence
<220> FEATURE:
<223> OTHER INFORMATION: Antibody Sequence 43 ADI-27278, ADI-30293,
      ADI-30296 LCDR3 Kabat L89-97

<400> SEQUENCE: 43

Gln Gln Ser Tyr Phe Phe Pro Thr
1               5

<210> SEQ ID NO 44
<211> LENGTH: 9
<212> TYPE: PRT
<213> ORGANISM: artificial sequence
<220> FEATURE:
<223> OTHER INFORMATION: Antibody Sequence 44 ADI-27291 HCDR1 KABAT
      numbering positions H27-35B

<400> SEQUENCE: 44

Phe Thr Phe Ser Ser Tyr Ala Met Ser
1               5

<210> SEQ ID NO 45
<211> LENGTH: 9
<212> TYPE: PRT
<213> ORGANISM: artificial sequence
<220> FEATURE:
<223> OTHER INFORMATION: Antibody Sequence 45 ADI-30283 HCDR1 KABAT
      numbering positions H27-35B

<400> SEQUENCE: 45

Phe Thr Phe Ser Pro Tyr Gly Met Ser
1               5

<210> SEQ ID NO 46
<211> LENGTH: 9
<212> TYPE: PRT
<213> ORGANISM: artificial sequence
<220> FEATURE:
<223> OTHER INFORMATION: Antibody Sequence 46 ADI-30286, ADI-30288 HCDR1
      KABAT numbering positions H27-35B

<400> SEQUENCE: 46

Phe Thr Phe Gly Pro Tyr Gly Met Ser
1               5

<210> SEQ ID NO 47
<211> LENGTH: 9
<212> TYPE: PRT
<213> ORGANISM: artificial sequence
<220> FEATURE:
<223> OTHER INFORMATION: Antibody Sequence 47 Consensus sequence
<220> FEATURE:
<221> NAME/KEY: misc_feature
<222> LOCATION: (4)..(5)
<223> OTHER INFORMATION: Xaa may be any natural amino acid, and
      preferably, Xaa at position 4 is selected from S, G and a
      conservatively substituted residue thereof, and Xaa at position 5
      is selected from S, P and a conservatively substituted residue
      thereof
<220> FEATURE:
<221> NAME/KEY: misc_feature
<222> LOCATION: (7)..(7)
<223> OTHER INFORMATION: Xaa may be any natural amino acid, preferably
      selected from A, G and a conservatively substituted residue
      thereof

<400> SEQUENCE: 47

Phe Thr Phe Xaa Xaa Tyr Xaa Met Ser
1               5

<210> SEQ ID NO 48
<211> LENGTH: 17
<212> TYPE: PRT
<213> ORGANISM: artificial sequence
<220> FEATURE:
<223> OTHER INFORMATION: Antibody Sequence 48 ADI-27291 HCDR2 KABAT
      H50-65

<400> SEQUENCE: 48

Ala Ile Ser Gly Ser Gly Gly Ser Thr Tyr Tyr Ala Asp Ser Val Lys
1               5                   10                  15

Gly

<210> SEQ ID NO 49
<211> LENGTH: 17
<212> TYPE: PRT
<213> ORGANISM: artificial sequence
<220> FEATURE:
<223> OTHER INFORMATION: Antibody Sequence 49 ADI-30283 HCDR2 KABAT
      H50-65

<400> SEQUENCE: 49

Ser Ile Ser Gly Ser Gly Gly Arg Thr Tyr Tyr Ala Asp Ser Val Lys
1               5                   10                  15

Gly

<210> SEQ ID NO 50
<211> LENGTH: 17

```
<212> TYPE: PRT
<213> ORGANISM: artificial sequence
<220> FEATURE:
<223> OTHER INFORMATION: Antibody Sequence 50 ADI-30286 HCDR2 KABAT
      H50-65

<400> SEQUENCE: 50

Ala Ile Ser Gly Ser Gly Ala Ser Thr Trp Tyr Ala Asp Ser Val Lys
1               5                   10                  15

Gly

<210> SEQ ID NO 51
<211> LENGTH: 17
<212> TYPE: PRT
<213> ORGANISM: artificial sequence
<220> FEATURE:
<223> OTHER INFORMATION: Antibody Sequence 51 ADI-30288 HCDR2 KABAT
      H50-65

<400> SEQUENCE: 51

Ala Ile Ser Gly Ser Gly Ala Ser Thr Trp His Ala Asp Ser Val Lys
1               5                   10                  15

Gly

<210> SEQ ID NO 52
<211> LENGTH: 17
<212> TYPE: PRT
<213> ORGANISM: artificial sequence
<220> FEATURE:
<223> OTHER INFORMATION: Antibody Sequence 52 Consensus sequence
<220> FEATURE:
<221> NAME/KEY: misc_feature
<222> LOCATION: (1)..(1)
<223> OTHER INFORMATION: Xaa may be any natural amino acid, preferably
      selected from A, S and a conservatively substituted residue
      thereof
<220> FEATURE:
<221> NAME/KEY: misc_feature
<222> LOCATION: (7)..(8)
<223> OTHER INFORMATION: Xaa may be any natural amino acid, and
      preferably, Xaa at position 7 is selected from G, A and a
      conservatively substituted residue thereof, and Xaa at position 8
      is selected from S, R and a conservatively substituted residue
      thereof
<220> FEATURE:
<221> NAME/KEY: misc_feature
<222> LOCATION: (10)..(11)
<223> OTHER INFORMATION: Xaa may be any natural amino acid, and
      preferably, Xaa at position 10 is selected from Y, W and a
      conservatively substituted residue thereof, and Xaa at position 11
      is selected from Y, H and a conservatively substituted residue
      thereof

<400> SEQUENCE: 52

Xaa Ile Ser Gly Ser Gly Xaa Xaa Thr Xaa Xaa Ala Asp Ser Val Lys
1               5                   10                  15

Gly

<210> SEQ ID NO 53
<211> LENGTH: 17
<212> TYPE: PRT
<213> ORGANISM: artificial sequence
<220> FEATURE:
<223> OTHER INFORMATION: Antibody Sequence 53 ADI-27291, ADI-30283 HCDR3
      Kabat H93-102

<400> SEQUENCE: 53

Ala Lys Asp Pro Gly Thr Asp Ser Ser Gly Tyr Tyr Tyr Ile Trp Arg
1               5                   10                  15
```

Tyr

<210> SEQ ID NO 54
<211> LENGTH: 17
<212> TYPE: PRT
<213> ORGANISM: artificial sequence
<220> FEATURE:
<223> OTHER INFORMATION: Antibody Sequence 54 ADI-30286 HCDR3 Kabat
      H93-102

<400> SEQUENCE: 54

Ala Lys Asp Pro Gly Thr His Tyr Ser Gly Tyr Tyr Tyr Ile Trp Arg
1               5                   10                  15

Tyr

<210> SEQ ID NO 55
<211> LENGTH: 17
<212> TYPE: PRT
<213> ORGANISM: artificial sequence
<220> FEATURE:
<223> OTHER INFORMATION: Antibody Sequence 55 ADI-30288 HCDR3 Kabat
      H93-102

<400> SEQUENCE: 55

Ala Lys Asp Pro Gly Thr Asp Ser Thr Gly Tyr Tyr Tyr Ile Trp Arg
1               5                   10                  15

Tyr

<210> SEQ ID NO 56
<211> LENGTH: 17
<212> TYPE: PRT
<213> ORGANISM: artificial sequence
<220> FEATURE:
<223> OTHER INFORMATION: Antibody Sequence 56 Consensus sequence
<220> FEATURE:
<221> NAME/KEY: misc_feature
<222> LOCATION: (7)..(9)
<223> OTHER INFORMATION: Xaa may be any natural amino acid, and
      preferably, Xaa at position 7 is selected from D, H and a
      conservatively substituted residue thereof, Xaa at position 8 is
      selected from S, Y and a conservatively substituted residue
      thereof, and Xaa at position 9 is selected from S, T and a
      conservatively substituted residue thereof

<400> SEQUENCE: 56

Ala Lys Asp Pro Gly Thr Xaa Xaa Xaa Gly Tyr Tyr Tyr Ile Trp Arg
1               5                   10                  15

Tyr

<210> SEQ ID NO 57
<211> LENGTH: 11
<212> TYPE: PRT
<213> ORGANISM: artificial sequence
<220> FEATURE:
<223> OTHER INFORMATION: Antibody Sequence 57 ADI-27291, ADI-30296,
      ADI-30286, ADI-30288 LCDR1 Kabat L24-34

<400> SEQUENCE: 57

Arg Ala Ser Gln Ser Val Ser Ser Asn Leu Ala
1               5                   10

<210> SEQ ID NO 58
<211> LENGTH: 7
<212> TYPE: PRT
<213> ORGANISM: artificial sequence
<220> FEATURE:

<223> OTHER INFORMATION: Antibody Sequence 58 ADI-27291, ADI-30283,
      ADI-30286, ADI-30288 LCDR2 Kabat L50-56

<400> SEQUENCE: 58

Ser Ala Ser Thr Arg Ala Thr
1               5

<210> SEQ ID NO 59
<211> LENGTH: 10
<212> TYPE: PRT
<213> ORGANISM: artificial sequence
<220> FEATURE:
<223> OTHER INFORMATION: Antibody Sequence 59 ADI-27291, ADI-30283,
      ADI-30286, ADI-30288 LCDR3 Kabat L89-97

<400> SEQUENCE: 59

Gln Gln Tyr Val Pro His Pro Pro Phe Thr
1               5                   10

<210> SEQ ID NO 60
<211> LENGTH: 9
<212> TYPE: PRT
<213> ORGANISM: artificial sequence
<220> FEATURE:
<223> OTHER INFORMATION: Antibody Sequence 60 ADI-27297 HCDR1 KABAT
      numbering positions H27-35B

<400> SEQUENCE: 60

Tyr Thr Phe Thr Ser Tyr Tyr Met His
1               5

<210> SEQ ID NO 61
<211> LENGTH: 9
<212> TYPE: PRT
<213> ORGANISM: artificial sequence
<220> FEATURE:
<223> OTHER INFORMATION: Antibody Sequence 61 ADI-30272, ADI-30278 HCDR1
      KABAT numbering positions H27-35B

<400> SEQUENCE: 61

Tyr Thr Phe Thr Glu Tyr Tyr Met His
1               5

<210> SEQ ID NO 62
<211> LENGTH: 9
<212> TYPE: PRT
<213> ORGANISM: artificial sequence
<220> FEATURE:
<223> OTHER INFORMATION: Antibody Sequence 62 Consensus sequence
<220> FEATURE:
<221> NAME/KEY: misc_feature
<222> LOCATION: (5)..(5)
<223> OTHER INFORMATION: Xaa may be any natural amino acid, preferably
      selected from S, E and a conservatively substituted residue
      thereof

<400> SEQUENCE: 62

Tyr Thr Phe Thr Xaa Tyr Tyr Met His
1               5

<210> SEQ ID NO 63
<211> LENGTH: 17
<212> TYPE: PRT
<213> ORGANISM: artificial sequence
<220> FEATURE:
<223> OTHER INFORMATION: Antibody Sequence 63 ADI-30272 HCDR2 KABAT
      H50-65

<400> SEQUENCE: 63

```
Ile Ile Ser Pro Ser Ala Gly Ser Thr Ser Tyr Ala Gln Lys Phe Gln
1               5                   10                  15

Gly
```

<210> SEQ ID NO 64
<211> LENGTH: 17
<212> TYPE: PRT
<213> ORGANISM: artificial sequence
<220> FEATURE:
<223> OTHER INFORMATION: Antibody Sequence 64 ADI-30278 HCDR2 KABAT
      H50-65

<400> SEQUENCE: 64

```
Ile Ile Ser Pro Ser Ala Gly Ser Thr Lys Tyr Ala Gln Lys Phe Gln
1               5                   10                  15

Gly
```

<210> SEQ ID NO 65
<211> LENGTH: 17
<212> TYPE: PRT
<213> ORGANISM: artificial sequence
<220> FEATURE:
<223> OTHER INFORMATION: Antibody Sequence 65 Consensus sequence
<220> FEATURE:
<221> NAME/KEY: misc_feature
<222> LOCATION: (3)..(3)
<223> OTHER INFORMATION: Xaa may be any natural amino acid, preferably
      selected from N, S and a conservatively substituted residue
      thereof
<220> FEATURE:
<221> NAME/KEY: misc_feature
<222> LOCATION: (6)..(6)
<223> OTHER INFORMATION: Xaa may be any natural amino acid, preferably
      selected from G, A and a conservatively substituted residue
      thereof
<220> FEATURE:
<221> NAME/KEY: misc_feature
<222> LOCATION: (10)..(10)
<223> OTHER INFORMATION: Xaa may be any natural amino acid, preferably
      selected from S, K and a conservatively substituted residue
      thereof

<400> SEQUENCE: 65

```
Ile Ile Xaa Pro Ser Xaa Gly Ser Thr Xaa Tyr Ala Gln Lys Phe Gln
1               5                   10                  15

Gly
```

<210> SEQ ID NO 66
<211> LENGTH: 15
<212> TYPE: PRT
<213> ORGANISM: artificial sequence
<220> FEATURE:
<223> OTHER INFORMATION: Antibody Sequence 66 ADI-27297, ADI-30272 HCDR3
      Kabat H93-102

<400> SEQUENCE: 66

```
Ala Arg Asp His Asp Ile Ala Ala Ala Gly Arg Leu Ala Asp Tyr
1               5                   10                  15
```

<210> SEQ ID NO 67
<211> LENGTH: 15
<212> TYPE: PRT
<213> ORGANISM: artificial sequence
<220> FEATURE:
<223> OTHER INFORMATION: Antibody Sequence 67 ADI-30278 HCDR3 Kabat
      H93-102

<400> SEQUENCE: 67

```
Ala Arg Asp His Asp Ile Arg Leu Ala Gly Arg Leu Ala Asp Tyr
1               5                   10                  15

<210> SEQ ID NO 68
<211> LENGTH: 15
<212> TYPE: PRT
<213> ORGANISM: artificial sequence
<220> FEATURE:
<223> OTHER INFORMATION: Antibody Sequence 68 Consensus sequence
<220> FEATURE:
<221> NAME/KEY: misc_feature
<222> LOCATION: (7)..(8)
<223> OTHER INFORMATION: Xaa may be any natural amino acid, and
      preferably, Xaa at position 7 is selected from A, R and a
      conservatively substituted residue thereof, and Xaa at position 8
      is selected from A, L and a conservatively substituted residue
      thereof

<400> SEQUENCE: 68

Ala Arg Asp His Asp Ile Xaa Xaa Ala Gly Arg Leu Ala Asp Tyr
1               5                   10                  15

<210> SEQ ID NO 69
<211> LENGTH: 11
<212> TYPE: PRT
<213> ORGANISM: artificial sequence
<220> FEATURE:
<223> OTHER INFORMATION: Antibody Sequence 69 ADI-27297, ADI-30272,
      ADI-30278 LCDR1-Kabat L24-34

<400> SEQUENCE: 69

Arg Ala Ser Gln Gly Ile Ser Ser Trp Leu Ala
1               5                   10

<210> SEQ ID NO 70
<211> LENGTH: 9
<212> TYPE: PRT
<213> ORGANISM: artificial sequence
<220> FEATURE:
<223> OTHER INFORMATION: Antibody Sequence 70 ADI-27297, ADI-30272,
      ADI-30278 LCDR3 Kabat L89-97

<400> SEQUENCE: 70

Gln Gln Ala Val Ile Leu Pro Ile Thr
1               5

<210> SEQ ID NO 71
<211> LENGTH: 11
<212> TYPE: PRT
<213> ORGANISM: artificial sequence
<220> FEATURE:
<223> OTHER INFORMATION: Antibody Sequence 71 ADI-27301 HCDR1 KABAT
      numbering positions H27-35B

<400> SEQUENCE: 71

Gly Ser Ile Ser Ser Ser Ser Tyr Tyr Trp Gly
1               5                   10

<210> SEQ ID NO 72
<211> LENGTH: 11
<212> TYPE: PRT
<213> ORGANISM: artificial sequence
<220> FEATURE:
<223> OTHER INFORMATION: Antibody Sequence 72 ADI-30306 HCDR1 KABAT
      numbering positions H27-35B

<400> SEQUENCE: 72

Gly Ser Ile Ser Ser Ser Leu Tyr Tyr Trp Gly
```

```
<210> SEQ ID NO 73
<211> LENGTH: 11
<212> TYPE: PRT
<213> ORGANISM: artificial sequence
<220> FEATURE:
<223> OTHER INFORMATION: Antibody Sequence 73 ADI-30311 HCDR1 KABAT
      numbering positions H27-35B

<400> SEQUENCE: 73

Gly Ser Ile Ala Ser Ser Val Tyr Tyr Trp Gly
1               5                   10

<210> SEQ ID NO 74
<211> LENGTH: 11
<212> TYPE: PRT
<213> ORGANISM: artificial sequence
<220> FEATURE:
<223> OTHER INFORMATION: Antibody Sequence 74 Consensus sequence
<220> FEATURE:
<221> NAME/KEY: misc_feature
<222> LOCATION: (4)..(4)
<223> OTHER INFORMATION: Xaa may be any natural amino acid, preferably
      selected from A, S and a conservatively substituted residue
      thereof
<220> FEATURE:
<221> NAME/KEY: misc_feature
<222> LOCATION: (7)..(7)
<223> OTHER INFORMATION: Xaa may be any natural amino acid, preferably
      selected from S, L, V and a conservatively substituted residue
      thereof

<400> SEQUENCE: 74

Gly Ser Ile Xaa Ser Ser Xaa Tyr Tyr Trp Gly
1               5                   10

<210> SEQ ID NO 75
<211> LENGTH: 16
<212> TYPE: PRT
<213> ORGANISM: artificial sequence
<220> FEATURE:
<223> OTHER INFORMATION: Antibody Sequence 75 ADI-30306 HCDR2 KABAT
      H50-65

<400> SEQUENCE: 75

Ser Ile Tyr Tyr Ser Gly Ser Thr Phe Tyr Asn Pro Ser Phe Lys Ser
1               5                   10                  15

<210> SEQ ID NO 76
<211> LENGTH: 16
<212> TYPE: PRT
<213> ORGANISM: artificial sequence
<220> FEATURE:
<223> OTHER INFORMATION: Antibody Sequence 76 ADI-30311 HCDR2 KABAT
      H50-65

<400> SEQUENCE: 76

Ser Ile Tyr Tyr Ser Gly Ser Thr Trp Tyr Asn Pro Ser Leu Lys Ser
1               5                   10                  15

<210> SEQ ID NO 77
<211> LENGTH: 16
<212> TYPE: PRT
<213> ORGANISM: artificial sequence
<220> FEATURE:
<223> OTHER INFORMATION: Antibody Sequence 77 Consensus sequence
<220> FEATURE:
<221> NAME/KEY: misc_feature
<222> LOCATION: (9)..(9)
```

```
<223> OTHER INFORMATION: Xaa may be any natural amino acid, preferably
      selected from Y, F, W and a conservatively substituted residue
      thereof
<220> FEATURE:
<221> NAME/KEY: misc_feature
<222> LOCATION: (14)..(14)
<223> OTHER INFORMATION: Xaa may be any natural amino acid, preferably
      selected from L, F and a conservatively substituted residue
      thereof

<400> SEQUENCE: 77

Ser Ile Tyr Tyr Ser Gly Ser Thr Xaa Tyr Asn Pro Ser Xaa Lys Ser
1               5                   10                  15

<210> SEQ ID NO 78
<211> LENGTH: 15
<212> TYPE: PRT
<213> ORGANISM: artificial sequence
<220> FEATURE:
<223> OTHER INFORMATION: Antibody Sequence 78 ADI-27301, ADI-30306 HCDR3
      Kabat H93-102

<400> SEQUENCE: 78

Ala Arg Glu Ala Gly Arg Gly Thr Thr Gly Leu Leu Phe Asp Tyr
1               5                   10                  15

<210> SEQ ID NO 79
<211> LENGTH: 15
<212> TYPE: PRT
<213> ORGANISM: artificial sequence
<220> FEATURE:
<223> OTHER INFORMATION: Antibody Sequence 79 ADI-30311 HCDR3 Kabat
      H93-102

<400> SEQUENCE: 79

Ala Arg Glu Ala Gly Arg Thr Gly Thr Gly Leu Leu Phe Asp Tyr
1               5                   10                  15

<210> SEQ ID NO 80
<211> LENGTH: 15
<212> TYPE: PRT
<213> ORGANISM: artificial sequence
<220> FEATURE:
<223> OTHER INFORMATION: Antibody Sequence 80 Consensus sequence
<220> FEATURE:
<221> NAME/KEY: misc_feature
<222> LOCATION: (7)..(8)
<223> OTHER INFORMATION: Xaa may be any natural amino acid, and
      preferably, Xaa at position 7 is selected from G, T and a
      conservatively substituted residue thereof, and Xaa at position 8
      is selected from T, G and a conservatively substituted residue
      thereof

<400> SEQUENCE: 80

Ala Arg Glu Ala Gly Arg Xaa Xaa Thr Gly Leu Leu Phe Asp Tyr
1               5                   10                  15

<210> SEQ ID NO 81
<211> LENGTH: 11
<212> TYPE: PRT
<213> ORGANISM: artificial sequence
<220> FEATURE:
<223> OTHER INFORMATION: Antibody Sequence 81 ADI-27301, ADI-30306,
      ADI-30311 LCDR1 Kabat L24-34

<400> SEQUENCE: 81

Arg Ala Ser Gln Ser Ile Ser Ser Trp Leu Ala
1               5                   10
```

```
<210> SEQ ID NO 82
<211> LENGTH: 7
<212> TYPE: PRT
<213> ORGANISM: artificial sequence
<220> FEATURE:
<223> OTHER INFORMATION: Antibody Sequence 82 ADI-27301, ADI-30306,
      ADI-30311 LCDR2-Kabat L50-56

<400> SEQUENCE: 82

Lys Ala Ser Ser Leu Glu Ser
1               5

<210> SEQ ID NO 83
<211> LENGTH: 9
<212> TYPE: PRT
<213> ORGANISM: artificial sequence
<220> FEATURE:
<223> OTHER INFORMATION: Antibody Sequence 83 ADI-27301, ADI-30306,
      ADI-30311 LCDR3 Kabat L89-97

<400> SEQUENCE: 83

Gln Gln Tyr Gly Ile Leu Pro Arg Thr
1               5

<210> SEQ ID NO 84
<211> LENGTH: 122
<212> TYPE: PRT
<213> ORGANISM: artificial sequence
<220> FEATURE:
<223> OTHER INFORMATION: Antibody Sequence 84 ADI-27238 VH

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Ser Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Arg Tyr Pro Ser Ser Trp Pro Tyr Gly Met Asp Val Trp
            100                 105                 110

Gly Gln Gly Thr Thr Val Thr Val Ser Ser
        115                 120

<210> SEQ ID NO 85
<211> LENGTH: 122
<212> TYPE: PRT
<213> ORGANISM: artificial sequence
<220> FEATURE:
<223> OTHER INFORMATION: Antibody Sequence 85 ADI-30263 VH

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Leu Ser Tyr
            20                  25                  30

Tyr Met Asn Trp Val Arg Gln Ala Pro Gly Gln Gly Leu Glu Trp Met
        35                  40                  45
```

Gly Ile Ile Asp Pro Ser Gly Arg Thr Ser Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Arg Tyr Pro Ser Ser Trp Pro Tyr Gly Thr Asp Val Trp
            100                 105                 110

Gly Gln Gly Thr Thr Val Thr Val Ser Ser
            115                 120

<210> SEQ ID NO 86
<211> LENGTH: 122
<212> TYPE: PRT
<213> ORGANISM: artificial sequence
<220> FEATURE:
<223> OTHER INFORMATION: Antibody Sequence 86 ADI-30267 VH

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Tyr
                20                  25                  30

Tyr Met Ser Trp Val Arg Gln Ala Pro Gly Gln Gly Leu Glu Trp Met
            35                  40                  45

Gly Ile Ile Asp Pro Ser Gly Arg Thr Ser Phe Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Arg Tyr Pro Glu Ser Trp Pro Tyr Gly Met Asp Val Trp
            100                 105                 110

Gly Gln Gly Thr Thr Val Thr Val Ser Ser
            115                 120

<210> SEQ ID NO 87
<211> LENGTH: 122
<212> TYPE: PRT
<213> ORGANISM: artificial sequence
<220> FEATURE:
<223> OTHER INFORMATION: Antibody Sequence 87 ADI-30268 VH

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Ser Tyr
                20                  25                  30

Tyr Met Gly Trp Val Arg Gln Ala Pro Gly Gln Gly Leu Glu Trp Met
            35                  40                  45

Gly Ile Ile Asp Pro Ser Gly Arg Thr Ser Tyr Ala Arg Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Arg Thr Pro Ser Ser Trp Pro Tyr Gly Met Asp Val Trp

```
                100                 105                 110
Gly Gln Gly Thr Thr Val Thr Val Ser Ser
        115                 120

<210> SEQ ID NO 88
<211> LENGTH: 122
<212> TYPE: PRT
<213> ORGANISM: artificial sequence
<220> FEATURE:
<223> OTHER INFORMATION: Antibody Sequence 88 ADI-27243 VH

<400> SEQUENCE: 88

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Arg Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Leu Tyr His Thr Pro Glu Tyr Phe Gln His Trp
            100                 105                 110

Gly Gln Gly Thr Leu Val Thr Val Ser Ser
        115                 120

<210> SEQ ID NO 89
<211> LENGTH: 122
<212> TYPE: PRT
<213> ORGANISM: artificial sequence
<220> FEATURE:
<223> OTHER INFORMATION: Antibody Sequence 89 ADI-30302 VH

<400> SEQUENCE: 89

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Ser Ser
            20                  25                  30

Gln Tyr Tyr Trp Gly Trp Ile Arg Gln Pro Pro Gly Lys Gly Leu Glu
        35                  40                  45

Trp Ile Gly Ser Ile Tyr Arg Ser Gly Gly Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Leu Tyr His Thr Pro Glu Tyr Phe Gln His Trp
            100                 105                 110

Gly Gln Gly Thr Leu Val Thr Val Ser Ser
        115                 120

<210> SEQ ID NO 90
<211> LENGTH: 122
<212> TYPE: PRT
<213> ORGANISM: artificial sequence
<220> FEATURE:
```

<223> OTHER INFORMATION: Antibody Sequence 90 ADI-30336 VH

<400> SEQUENCE: 90

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Arg Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Leu Tyr His Thr Pro Glu Tyr Phe Gln His Trp
            100                 105                 110

Gly Gln Gly Thr Leu Val Thr Val Ser Ser
        115                 120

<210> SEQ ID NO 91
<211> LENGTH: 122
<212> TYPE: PRT
<213> ORGANISM: artificial sequence
<220> FEATURE:
<223> OTHER INFORMATION: Antibody Sequence 91 ADI-27278 VH

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Gly Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Arg Ile Ala Asp Ser Pro Ser Arg Ala Phe Asp Ile Trp
            100                 105                 110

Gly Gln Gly Thr Met Val Thr Val Ser Ser
        115                 120

<210> SEQ ID NO 92
<211> LENGTH: 121
<212> TYPE: PRT
<213> ORGANISM: artificial sequence
<220> FEATURE:
<223> OTHER INFORMATION: Antibody Sequence 92 ADI-30293 VH

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val

```
                35                  40                  45
Ser Tyr Ile Ser Ser Ser Gly Thr Ile Asn Tyr Ala Asp Ser Val Lys
 50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Arg His Arg Ile Ala Asp Ser Pro Ser Arg Ala Phe Asp Ile Trp Gly
                100                 105                 110

Gln Gly Thr Met Val Thr Val Ser Ser
        115                 120

<210> SEQ ID NO 93
<211> LENGTH: 121
<212> TYPE: PRT
<213> ORGANISM: artificial sequence
<220> FEATURE:
<223> OTHER INFORMATION: Antibody Sequence 93 ADI-30296 VH

<400> SEQUENCE: 93

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ile Gly Gly Tyr
                20                  25                  30

Ser Met Asn Trp Val Arg Gln Ala Pro Gly Lys Gly Leu Glu Trp Val
                35                  40                  45

Ser Tyr Ile Ser Ser Ser Thr Ile His Tyr Ala Asp Ser Val Lys
 50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Arg His Arg Ile Gly Arg Ser Pro Ser Arg Ala Phe Asp Ile Trp Gly
                100                 105                 110

Gln Gly Thr Met Val Thr Val Ser Ser
        115                 120

<210> SEQ ID NO 94
<211> LENGTH: 124
<212> TYPE: PRT
<213> ORGANISM: artificial sequence
<220> FEATURE:
<223> OTHER INFORMATION: Antibody Sequence 94 ADI-27291 VH

<400> SEQUENCE: 94

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Lys Asp Pro Gly Thr Asp Ser Ser Gly Tyr Tyr Ile Trp Arg
            100                 105                 110

Tyr Trp Gly Gln Gly Thr Leu Val Thr Val Ser Ser
        115                 120

<210> SEQ ID NO 95
<211> LENGTH: 124
<212> TYPE: PRT
<213> ORGANISM: artificial sequence
<220> FEATURE:
<223> OTHER INFORMATION: Antibody Sequence 95 ADI-30283 VH

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Gly Met Ser Trp Val Arg Gln Ala Pro Gly Lys Gly Leu Glu Trp Val
        35                  40                  45

Ser Ser Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Asp Ser Ser Gly Tyr Tyr Tyr Ile Trp Arg
            100                 105                 110

Tyr Trp Gly Gln Gly Thr Leu Val Thr Val Ser Ser
        115                 120

<210> SEQ ID NO 96
<211> LENGTH: 124
<212> TYPE: PRT
<213> ORGANISM: artificial sequence
<220> FEATURE:
<223> OTHER INFORMATION: Antibody Sequence 96 ADI-30286 VH

<400> SEQUENCE: 96

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Pro Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Ala Ser Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr His Tyr Ser Gly Tyr Tyr Tyr Ile Trp Arg
            100                 105                 110

Tyr Trp Gly Gln Gly Thr Leu Val Thr Val Ser Ser
        115                 120

<210> SEQ ID NO 97
<211> LENGTH: 124
<212> TYPE: PRT
<213> ORGANISM: artificial sequence
<220> FEATURE:
<223> OTHER INFORMATION: Antibody Sequence 97 ADI-30288 VH

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Pro Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Ala Ser Thr Trp His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Asp Ser Thr Gly Tyr Tyr Tyr Ile Trp Arg
            100                 105                 110

Tyr Trp Gly Gln Gly Thr Leu Val Thr Val Ser Ser
        115                 120

<210> SEQ ID NO 98
<211> LENGTH: 122
<212> TYPE: PRT
<213> ORGANISM: artificial sequence
<220> FEATURE:
<223> OTHER INFORMATION: Antibody Sequence 98 ADI-27297 VH

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp His Asp Ile Ala Ala Gly Arg Leu Ala Asp Tyr Trp
            100                 105                 110

Gly Gln Gly Thr Leu Val Thr Val Ser Ser
        115                 120

<210> SEQ ID NO 99
<211> LENGTH: 122
<212> TYPE: PRT
<213> ORGANISM: artificial sequence
<220> FEATURE:
<223> OTHER INFORMATION: Antibody Sequence 99 ADI-30272 VH

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Tyr Met His Trp Val Arg Gln Ala Pro Gly Gln Gly Leu Glu Trp Met
            35                  40                  45

Gly Ile Ile Ser Pro Ser Ala Gly Ser Thr Ser Tyr Ala Gln Lys Phe
 50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp His Asp Ile Ala Ala Gly Arg Leu Ala Asp Tyr Trp
                100                 105                 110

Gly Gln Gly Thr Leu Val Thr Val Ser Ser
            115                 120

<210> SEQ ID NO 100
<211> LENGTH: 122
<212> TYPE: PRT
<213> ORGANISM: artificial sequence
<220> FEATURE:
<223> OTHER INFORMATION: Antibody Sequence 100 ADI-30278 VH

<400> SEQUENCE: 100

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Tyr Met His Trp Val Arg Gln Ala Pro Gly Gln Gly Leu Glu Trp Met
            35                  40                  45

Gly Ile Ile Ser Pro Ser Ala Gly Ser Thr Lys Tyr Ala Gln Lys Phe
 50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp His Asp Ile Arg Leu Ala Gly Arg Leu Ala Asp Tyr Trp
                100                 105                 110

Gly Gln Gly Thr Leu Val Thr Val Ser Ser
            115                 120

<210> SEQ ID NO 101
<211> LENGTH: 123
<212> TYPE: PRT
<213> ORGANISM: artificial sequence
<220> FEATURE:
<223> OTHER INFORMATION: Antibody Sequence 101 ADI-27301 VH

<400> SEQUENCE: 101

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

```
Cys Ala Arg Glu Ala Gly Arg Gly Thr Thr Gly Leu Leu Phe Asp Tyr
            100                 105                 110

Trp Gly Gln Gly Thr Leu Val Thr Val Ser Ser
        115                 120

<210> SEQ ID NO 102
<211> LENGTH: 123
<212> TYPE: PRT
<213> ORGANISM: artificial sequence
<220> FEATURE:
<223> OTHER INFORMATION: Antibody Sequence 102 ADI-30306 VH

<400> SEQUENCE: 102

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Leu Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Phe Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ala Gly Arg Gly Thr Thr Gly Leu Leu Phe Asp Tyr
            100                 105                 110

Trp Gly Gln Gly Thr Leu Val Thr Val Ser Ser
        115                 120

<210> SEQ ID NO 103
<211> LENGTH: 123
<212> TYPE: PRT
<213> ORGANISM: artificial sequence
<220> FEATURE:
<223> OTHER INFORMATION: Antibody Sequence 103 ADI-30311 VH

<400> SEQUENCE: 103

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ala Ser Ser
            20                  25                  30

Val Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Trp Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ala Gly Arg Thr Gly Thr Gly Leu Leu Phe Asp Tyr
            100                 105                 110

Trp Gly Gln Gly Thr Leu Val Thr Val Ser Ser
        115                 120

<210> SEQ ID NO 104
<211> LENGTH: 107
<212> TYPE: PRT
```

<213> ORGANISM: artificial sequence
<220> FEATURE:
<223> OTHER INFORMATION: Antibody Sequence 104 ADI-27238, ADI-30263,
ADI-30267, ADI-30268 VL

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Leu Thr Pro Phe
                85                  90                  95

Thr Phe Gly Gly Gly Thr Lys Val Glu Ile Lys
            100                 105

<210> SEQ ID NO 105
<211> LENGTH: 107
<212> TYPE: PRT
<213> ORGANISM: artificial sequence
<220> FEATURE:
<223> OTHER INFORMATION: Antibody Sequence 105 ADI-27243, ADI-30302 VL

<400> SEQUENCE: 105

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Phe Ala Phe Pro Tyr
                85                  90                  95

Thr Phe Gly Gly Gly Thr Lys Val Glu Ile Lys
            100                 105

<210> SEQ ID NO 106
<211> LENGTH: 107
<212> TYPE: PRT
<213> ORGANISM: artificial sequence
<220> FEATURE:
<223> OTHER INFORMATION: Antibody Sequence 106 ADI-30336 VL

<400> SEQUENCE: 106

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly

-continued

```
                    50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Phe Ala His Pro Tyr
                     85                  90                  95

Thr Phe Gly Gly Gly Thr Lys Val Glu Ile Lys
                100                 105

<210> SEQ ID NO 107
<211> LENGTH: 112
<212> TYPE: PRT
<213> ORGANISM: artificial sequence
<220> FEATURE:
<223> OTHER INFORMATION: Antibody Sequence 107 ADI-27278, ADI-30293,
      ADI-30296 VL

<400> SEQUENCE: 107

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Phe Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Phe Phe Pro Thr Phe Gly Gly Gly Thr Lys Val Glu Ile Lys
                100                 105                 110

<210> SEQ ID NO 108
<211> LENGTH: 108
<212> TYPE: PRT
<213> ORGANISM: artificial sequence
<220> FEATURE:
<223> OTHER INFORMATION: Antibody Sequence 108 ADI-27291, ADI-30283,
      ADI-30286, ADI-30288 VL

<400> SEQUENCE: 108

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Ser Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Val Pro His Pro Pro
                 85                  90                  95

Phe Thr Phe Gly Gly Gly Thr Lys Val Glu Ile Lys
                100                 105

<210> SEQ ID NO 109
<211> LENGTH: 107
<212> TYPE: PRT
```

<213> ORGANISM: artificial sequence
<220> FEATURE:
<223> OTHER INFORMATION: Antibody Sequence 109 ADI-27297, ADI-30272, ADI-30278 VL

<400> SEQUENCE: 109

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Val Ile Leu Pro Ile
                85                  90                  95

Thr Phe Gly Gly Gly Thr Lys Val Glu Ile Lys
            100                 105

<210> SEQ ID NO 110
<211> LENGTH: 107
<212> TYPE: PRT
<213> ORGANISM: artificial sequence
<220> FEATURE:
<223> OTHER INFORMATION: Antibody Sequence 110 ADI-27301, ADI-30306, ADI-30311 VL

<400> SEQUENCE: 110

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ile Leu Pro Arg
                85                  90                  95

Thr Phe Gly Gly Gly Thr Lys Val Glu Ile Lys
            100                 105

<210> SEQ ID NO 111
<211> LENGTH: 448
<212> TYPE: PRT
<213> ORGANISM: artificial sequence
<220> FEATURE:
<223> OTHER INFORMATION: Antibody Sequence 111 ADI-27238 HC

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Ser Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ala Arg Tyr Pro Ser Ser Trp Pro Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 112
<211> LENGTH: 448
<212> TYPE: PRT

<213> ORGANISM: artificial sequence
<220> FEATURE:
<223> OTHER INFORMATION: Antibody Sequence 112 ADI-30263 HC

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Leu Ser Tyr
            20                  25                  30

Tyr Met Asn Trp Val Arg Gln Ala Pro Gly Gln Gly Leu Glu Trp Met
        35                  40                  45

Gly Ile Ile Asp Pro Ser Gly Gly Arg Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Arg Tyr Pro Ser Ser Trp Pro Tyr Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu

```
              385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 113
<211> LENGTH: 448
<212> TYPE: PRT
<213> ORGANISM: artificial sequence
<220> FEATURE:
<223> OTHER INFORMATION: Antibody Sequence 113 ADI-30267 HC

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Tyr
            20                  25                  30

Tyr Met Ser Trp Val Arg Gln Ala Pro Gly Gln Gly Leu Glu Trp Met
        35                  40                  45

Gly Ile Ile Asp Pro Ser Gly Arg Thr Ser Phe Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Arg Tyr Pro Glu Ser Trp Pro Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
```

```
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Gln Glu Glu Met Thr Lys Asn Gln Val Ser Leu Thr
                355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
                420                 425                 430
Ala Leu His Asn His Tyr Thr Gln Lys Ser Leu Ser Leu Ser Leu Gly
                435                 440                 445

<210> SEQ ID NO 114
<211> LENGTH: 448
<212> TYPE: PRT
<213> ORGANISM: artificial sequence
<220> FEATURE:
<223> OTHER INFORMATION: Antibody Sequence 114 ADI-30268 HC

<400> SEQUENCE: 114

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Gly Ser Tyr
                20                  25                  30
Tyr Met Gly Trp Val Arg Gln Ala Pro Gly Gln Gly Leu Glu Trp Met
            35                  40                  45
Gly Ile Ile Asp Pro Ser Gly Gly Arg Thr Ser Tyr Ala Arg Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Ala Arg Thr Pro Ser Ser Trp Pro Tyr Gly Met Asp Val Trp
                100                 105                 110
Gly Gln Gly Thr Thr Val Thr Val Ser Ser Ala Ser Thr Lys Gly Pro
            115                 120                 125
Ser Val Phe Pro Leu Ala Pro Cys Ser Arg Ser Thr Ser Glu Ser Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Lys Thr Tyr Thr Cys Asn Val Asp
            195                 200                 205
His Lys Pro Ser Asn Thr Lys Val Asp Lys Arg Val Glu Ser Lys Tyr
    210                 215                 220
Gly Pro Pro Cys Pro Pro Cys Pro Ala Pro Glu Ala Ala Gly Gly Pro
```

```
            225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

<210> SEQ ID NO 115
<211> LENGTH: 448
<212> TYPE: PRT
<213> ORGANISM: artificial sequence
<220> FEATURE:
<223> OTHER INFORMATION: Antibody Sequence 115 ADI-27243 HC

<400> SEQUENCE: 115

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Arg Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Leu Tyr His Thr Pro Glu Tyr Phe Gln His Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
```

```
                145                 150                 155                 160
Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
                210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

<210> SEQ ID NO 116
<211> LENGTH: 448
<212> TYPE: PRT
<213> ORGANISM: artificial sequence
<220> FEATURE:
<223> OTHER INFORMATION: Antibody Sequence 116 ADI-30302 HC

<400> SEQUENCE: 116

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Ser Ser
                20                  25                  30

Gln Tyr Tyr Trp Gly Trp Ile Arg Gln Pro Pro Gly Lys Gly Leu Glu
                35                  40                  45

Trp Ile Gly Ser Ile Tyr Arg Ser Gly Gly Thr Tyr Tyr Asn Pro Ser
                50                  55                  60

Leu Lys Ser Arg Val Thr Ile Ser Val Asp Thr Ser Lys Asn Gln Phe
```

Ser Leu Lys Leu Ser Ser Val Thr Ala Ala Asp Thr Ala Val Tyr Tyr
 65                  70                  75                  80

Cys Ala Arg Asp Gly Leu Tyr His Thr Pro Glu Tyr Phe Gln His Trp
             85                  90                  95

Gly Gln Gly Thr Leu Val Thr Val Ser Ser Ala Ser Thr Lys Gly Pro
        100                 105                 110

Ser Val Phe Pro Leu Ala Pro Cys Ser Arg Ser Thr Ser Glu Ser Thr
    115                 120                 125

Ala Ala Leu Gly Cys Leu Val Lys Asp Tyr Phe Pro Glu Pro Val Thr
130                 135                 140

Val Ser Trp Asn Ser Gly Ala Leu Thr Ser Gly Val His Thr Phe Pro
145                 150                 155                 160

Ala Val Leu Gln Ser Ser Gly Leu Tyr Ser Leu Ser Ser Val Val Thr
                165                 170                 175

Val Pro Ser Ser Ser Leu Gly Thr Lys Thr Tyr Thr Cys Asn Val Asp
            180                 185                 190

His Lys Pro Ser Asn Thr Lys Val Asp Lys Arg Val Glu Ser Lys Tyr
        195                 200                 205

Gly Pro Pro Cys Pro Pro Cys Pro Ala Pro Glu Ala Ala Gly Gly Pro
    210                 215                 220

Ser Val Phe Leu Phe Pro Pro Lys Pro Lys Asp Thr Leu Met Ile Ser
225                 230                 235                 240

Arg Thr Pro Glu Val Thr Cys Val Val Val Asp Val Ser Gln Glu Asp
                245                 250                 255

Pro Glu Val Gln Phe Asn Trp Tyr Val Asp Gly Val Glu Val His Asn
            260                 265                 270

Ala Lys Thr Lys Pro Arg Glu Glu Gln Phe Asn Ser Thr Tyr Arg Val
        275                 280                 285

Val Ser Val Leu Thr Val Leu His Gln Asp Trp Leu Asn Gly Lys Glu
    290                 295                 300

Tyr Lys Cys Lys Val Ser Asn Lys Gly Leu Pro Ser Ser Ile Glu Lys
305                 310                 315                 320

Thr Ile Ser Lys Ala Lys Gly Gln Pro Arg Glu Pro Gln Val Tyr Thr
                325                 330                 335

Leu Pro Pro Ser Gln Glu Glu Met Thr Lys Asn Gln Val Ser Leu Thr
            340                 345                 350

Cys Leu Val Lys Gly Phe Tyr Pro Ser Asp Ile Ala Val Glu Trp Glu
        355                 360                 365

Ser Asn Gly Gln Pro Glu Asn Asn Tyr Lys Thr Thr Pro Pro Val Leu
    370                 375                 380

Asp Ser Asp Gly Ser Phe Phe Leu Tyr Ser Arg Leu Thr Val Asp Lys
385                 390                 395                 400

Ser Arg Trp Gln Glu Gly Asn Val Phe Ser Cys Ser Val Met His Glu
                405                 410                 415

Ala Leu His Asn His Tyr Thr Gln Lys Ser Leu Ser Leu Ser Leu Gly
            420                 425                 430

435                 440                 445

<210> SEQ ID NO 117
<211> LENGTH: 448
<212> TYPE: PRT
<213> ORGANISM: artificial sequence
<220> FEATURE:
<223> OTHER INFORMATION: Antibody Sequence 117 ADI-30336 HC

```
<400> SEQUENCE: 117

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Arg Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Leu Tyr His Thr Pro Glu Tyr Phe Gln His Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415
```

-continued

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

<210> SEQ ID NO 118
<211> LENGTH: 448
<212> TYPE: PRT
<213> ORGANISM: artificial sequence
<220> FEATURE:
<223> OTHER INFORMATION: Antibody Sequence 118 ADI-27278 HC

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Gly Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Arg Ile Ala Asp Ser Pro Ser Arg Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

```
Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
            435                 440                 445
```

<210> SEQ ID NO 119
<211> LENGTH: 447
<212> TYPE: PRT
<213> ORGANISM: artificial sequence
<220> FEATURE:
<223> OTHER INFORMATION: Antibody Sequence 119 ADI-30293 HC

<400> SEQUENCE: 119

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Gly Thr Ile Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg His Arg Ile Ala Asp Ser Pro Ser Arg Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly
            435                 440                 445

<210> SEQ ID NO 120
<211> LENGTH: 447
<212> TYPE: PRT
<213> ORGANISM: artificial sequence
<220> FEATURE:
<223> OTHER INFORMATION: Antibody Sequence 120 ADI-30296 HC

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Gly Gly Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile His Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg His Arg Ile Gly Arg Ser Pro Ser Arg Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 121
<211> LENGTH: 450
<212> TYPE: PRT
<213> ORGANISM: artificial sequence
<220> FEATURE:
<223> OTHER INFORMATION: Antibody Sequence 121 ADI-27291 HC

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Asp Ser Ser Gly Tyr Tyr Ile Trp Arg
            100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
            195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
            435                 440                 445

Leu Gly
    450

<210> SEQ ID NO 122
<211> LENGTH: 450
<212> TYPE: PRT
<213> ORGANISM: artificial sequence
<220> FEATURE:
<223> OTHER INFORMATION: Antibody Sequence 122 ADI-30283 HC

<400> SEQUENCE: 122

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Gly Met Ser Trp Val Arg Gln Ala Pro Gly Lys Gly Leu Glu Trp Val
        35                  40                  45

Ser Ser Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Asp Ser Ser Gly Tyr Tyr Tyr Ile Trp Arg
                100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415
```

```
Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly
    450

<210> SEQ ID NO 123
<211> LENGTH: 450
<212> TYPE: PRT
<213> ORGANISM: artificial sequence
<220> FEATURE:
<223> OTHER INFORMATION: Antibody Sequence 123 ADI-30286 HC

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Pro Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Ala Ser Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr His Tyr Ser Gly Tyr Tyr Ile Trp Arg
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320
```

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly
    450

<210> SEQ ID NO 124
<211> LENGTH: 450
<212> TYPE: PRT
<213> ORGANISM: artificial sequence
<220> FEATURE:
<223> OTHER INFORMATION: Antibody Sequence 124 ADI-30288 HC

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Pro Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Ala Ser Thr Trp His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Asp Ser Thr Gly Tyr Tyr Tyr Ile Trp Arg
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

```
Lys Tyr Gly Pro Pro Cys Pro Pro Cys Pro Ala Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly
    450

<210> SEQ ID NO 125
<211> LENGTH: 448
<212> TYPE: PRT
<213> ORGANISM: artificial sequence
<220> FEATURE:
<223> OTHER INFORMATION: Antibody Sequence 125 ADI-27297 HC

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp His Asp Ile Ala Ala Gly Arg Leu Ala Asp Tyr Trp
            100                 105                 110

Gly Gln Gly Thr Leu Val Thr Val Ser Ser Ala Ser Thr Lys Gly Pro
        115                 120                 125
```

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 126
<211> LENGTH: 448
<212> TYPE: PRT
<213> ORGANISM: artificial sequence
<220> FEATURE:
<223> OTHER INFORMATION: Antibody Sequence 126 ADI-30272 HC

<400> SEQUENCE: 126

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Tyr Met His Trp Val Arg Gln Ala Pro Gly Gln Gly Leu Glu Trp Met
            35                  40                  45

```
Gly Ile Ile Ser Pro Ser Ala Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp His Asp Ile Ala Ala Gly Arg Leu Ala Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

<210> SEQ ID NO 127
<211> LENGTH: 448
<212> TYPE: PRT
```

<213> ORGANISM: artificial sequence
<220> FEATURE:
<223> OTHER INFORMATION: Antibody Sequence 127 ADI-30278 HC

<400> SEQUENCE: 127

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Tyr Met His Trp Val Arg Gln Ala Pro Gly Gln Gly Leu Glu Trp Met
        35                  40                  45

Gly Ile Ile Ser Pro Ser Ala Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp His Asp Ile Arg Leu Ala Gly Arg Leu Ala Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

```
                385                 390                 395                 400
Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

<210> SEQ ID NO 128
<211> LENGTH: 449
<212> TYPE: PRT
<213> ORGANISM: artificial sequence
<220> FEATURE:
<223> OTHER INFORMATION: Antibody Sequence 128 ADI-27301 HC

<400> SEQUENCE: 128

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ala Gly Arg Gly Thr Thr Gly Leu Leu Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
```

```
                305                 310                 315                 320
Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Met Thr Lys Asn Gln Val Ser Leu
                355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly

<210> SEQ ID NO 129
<211> LENGTH: 449
<212> TYPE: PRT
<213> ORGANISM: artificial sequence
<220> FEATURE:
<223> OTHER INFORMATION: Antibody Sequence 129 ADI-30306 HC

<400> SEQUENCE: 129

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Leu Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Phe Tyr Asn Pro Ser
    50                  55                  60

Phe Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ala Gly Arg Gly Thr Thr Gly Leu Leu Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220
```

```
Tyr Gly Pro Pro Cys Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
        260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

Gly

<210> SEQ ID NO 130
<211> LENGTH: 449
<212> TYPE: PRT
<213> ORGANISM: artificial sequence
<220> FEATURE:
<223> OTHER INFORMATION: Antibody Sequence 130 ADI-30311 HC

<400> SEQUENCE: 130

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ala Ser Ser
            20                  25                  30

Val Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Trp Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Glu Ala Gly Arg Thr Gly Thr Gly Leu Leu Phe Asp Tyr
            100                 105                 110

Trp Gly Gln Gly Thr Leu Val Thr Val Ser Ser Ala Ser Thr Lys Gly
        115                 120                 125
```

```
Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly

<210> SEQ ID NO 131
<211> LENGTH: 441
<212> TYPE: PRT
<213> ORGANISM: artificial sequence
<220> FEATURE:
<223> OTHER INFORMATION: Antibody Sequence 131 Positive control antibody
      10A7-IgG4 (Genentech) HC

<400> SEQUENCE: 131

Glu Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
                20                  25                  30
```

```
Thr Met His Trp Val Arg Gln Ser Pro Gly Lys Gly Leu Glu Trp Val
         35                  40                  45

Ala Phe Ile Arg Ser Gly Ser Gly Ile Val Phe Tyr Ala Asp Ala Val
 50                  55                  60

Arg Gly Arg Phe Thr Ile Ser Arg Asp Asn Ala Lys Asn Leu Leu Phe
 65                  70                  75                  80

Leu Gln Met Asn Asp Leu Lys Ser Glu Asp Thr Ala Met Tyr Tyr Cys
                 85                  90                  95

Ala Arg Arg Pro Leu Gly His Asn Thr Phe Asp Ser Trp Gly Gln Gly
             100                 105                 110

Thr Leu Ala Ser Thr Lys Gly Pro Ser Val Phe Pro Leu Ala Pro Cys
         115                 120                 125

Ser Arg Ser Thr Ser Glu Ser Thr Ala Ala Leu Gly Cys Leu Val Lys
     130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                 165                 170                 175

Tyr Ser Leu Ser Ser Val Val Thr Val Pro Ser Ser Ser Leu Gly Thr
             180                 185                 190

Lys Thr Tyr Thr Cys Asn Val Asp His Lys Pro Ser Asn Thr Lys Val
         195                 200                 205

Asp Lys Arg Val Glu Ser Lys Tyr Gly Pro Pro Cys Pro Pro Cys Pro
     210                 215                 220

Ala Pro Glu Phe Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                 245                 250                 255

Val Val Asp Val Ser Gln Glu Asp Pro Glu Val Gln Phe Asn Trp Tyr
             260                 265                 270

Val Asp Gly Val Glu Val His Asn Ala Lys Thr Lys Pro Arg Glu Glu
         275                 280                 285

Gln Phe Asn Ser Thr Tyr Arg Val Val Ser Val Leu Thr Val Leu His
     290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                 325                 330                 335

Pro Arg Glu Pro Gln Val Tyr Thr Leu Pro Pro Ser Gln Glu Glu Met
             340                 345                 350

Thr Lys Asn Gln Val Ser Leu Thr Cys Leu Val Lys Gly Phe Tyr Pro
         355                 360                 365

Ser Asp Ile Ala Val Glu Trp Glu Ser Asn Gly Gln Pro Glu Asn Asn
     370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                 405                 410                 415

Phe Ser Cys Ser Val Met His Glu Ala Leu His Asn His Tyr Thr Gln
             420                 425                 430

Lys Ser Leu Ser Leu Ser Leu Gly Lys
         435                 440
```

```
<210> SEQ ID NO 132
<211> LENGTH: 457
<212> TYPE: PRT
<213> ORGANISM: artificial sequence
<220> FEATURE:
<223> OTHER INFORMATION: Antibody Sequence 132 Positive control antibody
      22G2-IgG4(BMS) HC

<400> SEQUENCE: 132

Gln Val His Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ile Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Tyr Val Ser Gly Asn Tyr Tyr Asn Val Asp Tyr
            100                 105                 110

Tyr Phe Phe Gly Val Asp Val Trp Gly Gln Gly Thr Thr Val Thr Val
        115                 120                 125

Ser Ser Ala Ser Thr Lys Gly Pro Ser Val Phe Pro Leu Ala Pro Cys
130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Lys Thr Tyr Thr Cys Asn Val Asp His Lys Pro Ser Asn Thr Lys Val
    210                 215                 220

Asp Lys Arg Val Glu Ser Lys Tyr Gly Pro Pro Cys Pro Pro Cys Pro
225                 230                 235                 240

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
        275                 280                 285

Val Asp Gly Val Glu Val His Asn Ala Lys Thr Lys Pro Arg Glu Glu
    290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Gln Glu Glu Met
        355                 360                 365
```

```
Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Glu Gly Asn Val
                420                 425                 430

Phe Ser Cys Ser Val Met His Glu Ala Leu His Asn His Tyr Thr Gln
                435                 440                 445

Lys Ser Leu Ser Leu Ser Leu Gly Lys
    450                 455

<210> SEQ ID NO 133
<211> LENGTH: 446
<212> TYPE: PRT
<213> ORGANISM: artificial sequence
<220> FEATURE:
<223> OTHER INFORMATION: Antibody Sequence 133 Positive control antibody
      31C6--IgG4(MSD) HC

<400> SEQUENCE: 133

Glu Val Gln Leu Gln Gln Ser Gly Pro Glu Leu Val Lys Pro Gly Ser
1               5                   10                  15

Ser Val Lys Met Ser Cys Lys Ala Ser Gly Tyr Thr Phe Ser Ser Tyr
                20                  25                  30

Val Met His Trp Val Lys Gln Lys Pro Gly Gln Gly Leu Glu Trp Ile
            35                  40                  45

Gly Tyr Ile Asp Pro Tyr Asn Asp Gly Ala Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Gly Pro Tyr Gly Trp Tyr Phe Asp Val Trp Gly Ala Gly
                100                 105                 110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
    195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270
```

```
Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 134
<211> LENGTH: 446
<212> TYPE: PRT
<213> ORGANISM: artificial sequence
<220> FEATURE:
<223> OTHER INFORMATION: Antibody Sequence 134 Positive control antibody
      1F4 HC

<400> SEQUENCE: 134

Glu Val Gln Leu Gln Gln Ser Gly Pro Glu Leu Val Lys Pro Gly Thr
1               5                   10                  15

Ser Met Lys Ile Ser Cys Lys Ala Ser Gly Tyr Ser Phe Thr Gly His
            20                  25                  30

Leu Met Asn Trp Val Lys Gln Ser His Gly Lys Asn Leu Glu Trp Ile
        35                  40                  45

Gly Leu Ile Ile Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Asp Asp Ser Ala Val Tyr Phe Cys
                85                  90                  95

Ser Arg Gly Leu Arg Gly Phe Tyr Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
                180             185             190
Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
            210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 135
<211> LENGTH: 467
<212> TYPE: PRT
<213> ORGANISM: artificial sequence
<220> FEATURE:
<223> OTHER INFORMATION: Antibody Sequence 135 Negative control IgG1 HC

<400> SEQUENCE: 135

Met Gly Trp Ser Leu Ile Leu Leu Phe Leu Val Ala Val Ala Thr Arg
1               5                   10                  15

Val Leu Ser Glu Val Arg Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Ala Met Gly Trp Val Arg Gln Ala Pro Gly Lys Gly Leu
    50                  55                  60

Glu Trp Val Ser Ala Ile Ser Gly Ser Gly Ser Thr Tyr Tyr Ala
65                  70                  75                  80

Asp Ser Val Lys Gly Arg Phe Thr Thr Ser Arg Asp Asp Ser Lys Asn
            85                  90                  95

Ala Leu Tyr Leu Gln Met Asn Ser Leu Arg Ala Glu Asp Thr Ala Val
```

```
            100                 105                 110
Tyr Tyr Cys Ala Arg Gly Gly Pro Gly Trp Tyr Ala Ala Asp Val Trp
            115                 120                 125
Gly Gln Gly Thr Thr Val Thr Val Ser Ser Ala Ser Thr Lys Gly Pro
            130                 135                 140
Ser Val Phe Pro Leu Ala Pro Ser Ser Lys Ser Thr Ser Gly Gly Thr
145                 150                 155                 160
Ala Ala Leu Gly Cys Leu Val Lys Asp Tyr Phe Pro Glu Pro Val Thr
            165                 170                 175
Val Ser Trp Asn Ser Gly Ala Leu Thr Ser Gly Val His Thr Phe Pro
            180                 185                 190
Ala Val Leu Gln Ser Ser Gly Leu Tyr Ser Leu Ser Ser Val Val Thr
            195                 200                 205
Val Pro Ser Ser Ser Leu Gly Thr Gln Thr Tyr Ile Cys Asn Val Asn
            210                 215                 220
His Lys Pro Ser Asn Thr Lys Val Asp Lys Lys Val Glu Pro Lys Ser
225                 230                 235                 240
Cys Asp Lys Thr His Thr Cys Pro Pro Cys Pro Ala Pro Glu Leu Leu
            245                 250                 255
Gly Gly Pro Ser Val Phe Leu Phe Pro Pro Lys Pro Lys Asp Thr Leu
            260                 265                 270
Met Ile Ser Arg Thr Pro Glu Val Thr Cys Val Val Val Asp Val Ser
            275                 280                 285
His Glu Asp Pro Glu Val Lys Phe Asn Trp Tyr Val Asp Gly Val Glu
            290                 295                 300
Val His Asn Ala Lys Thr Lys Pro Arg Glu Glu Gln Tyr Asn Ser Thr
305                 310                 315                 320
Tyr Arg Val Val Ser Val Leu Thr Val Leu His Gln Asp Trp Leu Asn
            325                 330                 335
Gly Lys Glu Tyr Lys Cys Lys Val Ser Asn Lys Ala Leu Pro Ala Pro
            340                 345                 350
Ile Glu Lys Thr Ile Ser Lys Ala Lys Gly Gln Pro Arg Glu Pro Gln
            355                 360                 365
Val Tyr Thr Leu Pro Pro Ser Arg Asp Glu Leu Thr Lys Asn Gln Val
            370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Lys Leu Thr
                420                 425                 430
Val Asp Lys Ser Arg Trp Gln Gln Gly Asn Val Phe Ser Cys Ser Val
                435                 440                 445
Met His Glu Ala Leu His Asn His Tyr Thr Gln Lys Ser Leu Ser Leu
                450                 455                 460
Ser Pro Gly
465

<210> SEQ ID NO 136
<211> LENGTH: 465
<212> TYPE: PRT
<213> ORGANISM: artificial sequence
<220> FEATURE:
<223> OTHER INFORMATION: Antibody Sequence 136 Negative control IgG4 HC
```

```
<400> SEQUENCE: 136

Met Gly Trp Ser Leu Ile Leu Leu Phe Leu Val Ala Val Ala Thr Arg
1               5                   10                  15

Val Leu Ser Glu Val Arg Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Ala Met Gly Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Thr Ser Arg Asp Asp Ser Lys Asn
                85                  90                  95

Ala Leu Tyr Leu Gln Met Asn Ser Leu Arg Ala Glu Asp Thr Ala Val
            100                 105                 110

Tyr Tyr Cys Ala Arg Gly Gly Pro Gly Trp Tyr Ala Ala Asp Val Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415
```

-continued

```
Asp Ser Asp Gly Ser Phe Phe Leu Tyr Ser Arg Leu Thr Val Asp Lys
                420                 425                 430

Ser Arg Trp Gln Glu Gly Asn Val Phe Ser Cys Ser Val Met His Glu
            435                 440                 445

Ala Leu His Asn His Tyr Thr Gln Lys Ser Leu Ser Leu Ser Leu Gly
        450                 455                 460

Lys
465

<210> SEQ ID NO 137
<211> LENGTH: 214
<212> TYPE: PRT
<213> ORGANISM: artificial sequence
<220> FEATURE:
<223> OTHER INFORMATION: Antibody Sequence 137 ADI-27238, ADI-30263,
      ADI-30267, ADI-30268 LC

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Leu Thr Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 138
<211> LENGTH: 214
<212> TYPE: PRT
<213> ORGANISM: artificial sequence
<220> FEATURE:
<223> OTHER INFORMATION: Antibody Sequence 138 ADI-27243, ADI-30302 LC

<400> SEQUENCE: 138

Glu Ile Val Leu Thr Gln Ser Pro Ala Thr Leu Ser Leu Ser Pro Gly
1               5                   10                  15
```

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Phe Ala Phe Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 139
<211> LENGTH: 214
<212> TYPE: PRT
<213> ORGANISM: artificial sequence
<220> FEATURE:
<223> OTHER INFORMATION: Antibody Sequence 139 ADI-30336 LC

<400> SEQUENCE: 139

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Phe Ala His Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 140
<211> LENGTH: 219
<212> TYPE: PRT
<213> ORGANISM: artificial sequence
<220> FEATURE:
<223> OTHER INFORMATION: Antibody Sequence 140 ADI-27278, ADI-30293,
      ADI-30296 LC

<400> SEQUENCE: 140

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Phe Phe Pro Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 141
<211> LENGTH: 215
<212> TYPE: PRT
<213> ORGANISM: artificial sequence
<220> FEATURE:
<223> OTHER INFORMATION: Antibody Sequence 141 ADI-27291, ADI-30283,
      ADI-30286, ADI-30288 LC

<400> SEQUENCE: 141

```
Glu Ile Val Met Thr Gln Ser Pro Ala Thr Leu Ser Val Ser Pro Gly
1               5                   10                  15
```

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
         35                  40                  45

Tyr Ser Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Val Pro His Pro Pro
                 85                  90                  95

Phe Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 142
<211> LENGTH: 214
<212> TYPE: PRT
<213> ORGANISM: artificial sequence
<220> FEATURE:
<223> OTHER INFORMATION: Antibody Sequence 142 ADI-27297, ADI-30272,
      ADI-30278 LC

<400> SEQUENCE: 142

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
         35                  40                  45

Ser Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Val Ile Leu Pro Ile
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 143
<211> LENGTH: 214
<212> TYPE: PRT
<213> ORGANISM: artificial sequence
<220> FEATURE:
<223> OTHER INFORMATION: Antibody Sequence 143 ADI-27301, ADI-30306,
      ADI-30311 LC

<400> SEQUENCE: 143

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ile Leu Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 144
<211> LENGTH: 220
<212> TYPE: PRT
<213> ORGANISM: artificial sequence
<220> FEATURE:
<223> OTHER INFORMATION: Antibody Sequence 144 Positive control antibody
      10A7-IgG4 LC

<400> SEQUENCE: 144

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Thr Gly Val
 50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 145
<211> LENGTH: 214
<212> TYPE: PRT
<213> ORGANISM: artificial sequence
<220> FEATURE:
<223> OTHER INFORMATION: Antibody Sequence 145 Positive control antibody
      22G2-IgG4(BMS) LC

<400> SEQUENCE: 145

Gly Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ile Asn Tyr
            20                  25                  30

Leu Ala Trp Cys Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Ser Gly
 50                  55                  60

Ser Gly Ser Gly Thr Asp Phe Thr Leu Thr Ile Ser Ser Leu Gln Ala
65                  70                  75                  80

Glu Asp Leu Ala Val Tyr Tyr Cys Gln Gln His Tyr Ser Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 146
<211> LENGTH: 214
<212> TYPE: PRT
<213> ORGANISM: artificial sequence
<220> FEATURE:
<223> OTHER INFORMATION: Antibody Sequence 146 Positive control antibody
      31C6-IgG4(MSD) LC

<400> SEQUENCE: 146

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu His Ile Tyr Ser Tyr
            20                  25                  30

Leu Ser Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Thr Tyr Tyr Cys Gln His His Phe Gly Ser Pro Leu
                85                  90                  95

Thr Phe Gly Ala Gly Thr Thr Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 147
<211> LENGTH: 219
<212> TYPE: PRT
<213> ORGANISM: artificial sequence
<220> FEATURE:
<223> OTHER INFORMATION: Antibody Sequence 147 Positive control antibody
      1F4 LC

<400> SEQUENCE: 147

Asp Val Val Leu Thr Gln Thr Pro Leu Ser Leu Ser Val Ser Phe Gly
```

```
1               5                   10                  15
Asp Gln Val Ser Ile Ser Cys Arg Ser Ser Gln Ser Leu Val Asn Ser
                20                  25                  30

Tyr Gly Asn Thr Phe Leu Ser Trp Tyr Leu His Lys Pro Gly Gln Ser
                35                  40                  45

Pro Gln Leu Leu Ile Phe Gly Ile Ser Asn Arg Phe Ser Gly Val Pro
            50                  55                  60

Asp Arg Phe Ser Gly Ser Gly Ser Gly Thr Asp Phe Thr Leu Lys Ile
65                  70                  75                  80

Ser Thr Ile Lys Pro Glu Asp Leu Gly Met Tyr Tyr Cys Leu Gln Gly
                85                  90                  95

Thr His Gln Pro Pro Thr Phe Gly Pro Gly Thr Lys Leu Glu Val Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
            210                 215

<210> SEQ ID NO 148
<211> LENGTH: 236
<212> TYPE: PRT
<213> ORGANISM: artificial sequence
<220> FEATURE:
<223> OTHER INFORMATION: Antibody Sequence 148 Negative control IgG1 LC

<400> SEQUENCE: 148

Met Asp Phe Gln Val Gln Ile Ile Ser Phe Leu Leu Ile Ser Ala Ser
1               5                   10                  15

Val Ile Met Ser Arg Gly Asp Ile Gln Met Thr Gln Ser Pro Ser Ser
                20                  25                  30

Leu Ser Ala Ser Val Gly Asp Arg Val Thr Ile Thr Cys Arg Ala Ser
                35                  40                  45

Gln Ser Ile Ser Ser Tyr Leu Asn Trp Tyr Gln Gln Lys Pro Gly Lys
            50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
                100                 105                 110

Ala Asp Leu Pro Ala Phe Ala Phe Gly Gly Gly Thr Lys Val Glu Ile
                115                 120                 125

Lys Arg Thr Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
```

```
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Cys
225                 230                 235

<210> SEQ ID NO 149
<211> LENGTH: 236
<212> TYPE: PRT
<213> ORGANISM: artificial sequence
<220> FEATURE:
<223> OTHER INFORMATION: Antibody Sequence 149 Negative control IgG4 LC

<400> SEQUENCE: 149

Met Asp Phe Gln Val Gln Ile Ile Ser Phe Leu Leu Ile Ser Ala Ser
1               5                   10                  15

Val Ile Met Ser Arg Gly Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Ser Ile Ser Ser Tyr Leu Asn Trp Tyr Gln Gln Lys Pro Gly Lys
        50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Asp Leu Pro Ala Phe Ala Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Cys
225                 230                 235

<210> SEQ ID NO 150
<211> LENGTH: 366
<212> TYPE: DNA
<213> ORGANISM: artificial sequence
<220> FEATURE:
<223> OTHER INFORMATION: Antibody Sequence 150 ADI-27238 VH DNA
```

<400> SEQUENCE: 150

```
caggtgcagc tggtgcagtc tggggctgag gtgaagaagc ctggggcctc agtgaaggtt      60
tcctgcaagg catctggata caccttcacc agctactata tgtcatgggt gcgacaggcc     120
cctggacaag gcttgagtg gatgggaata atcaaccta gtggtggtag cacaagctac      180
gcacagaagt tccagggcag agtcaccatg accagggaca cgtccacgag cacagtctac     240
atggagctga gcagcctgag atctgaggac acggcggtgt actactgcgc aagggctaga     300
tacccatcaa gctggccata cggaatggac gtatggggcc agggaacaac tgtcaccgtc     360
tcctca                                                                366
```

<210> SEQ ID NO 151
<211> LENGTH: 366
<212> TYPE: DNA
<213> ORGANISM: artificial sequence
<220> FEATURE:
<223> OTHER INFORMATION: Antibody Sequence 151 ADI-30263 VH DNA

<400> SEQUENCE: 151

```
caggtgcagc tggtgcagtc tggggctgag gtgaagaagc ctggggcctc agtgaaggtt      60
tcctgcaagg catctggata cacattcctg agctactata tgaattgggt gcgacaggcc     120
cctggacaag gcttgagtg gatgggaata atcgatccta gtggtggtag gacaagctac      180
gcacagaagt tccagggcag agtcaccatg accagggaca cgtccacgag cacagtctac     240
atggagctga gcagcctgag atctgaggac acggcggtgt actactgcgc aagggctaga     300
tacccatcaa gctggccata cggaacggat gtatggggcc agggaacaac tgtcaccgtc     360
tcctca                                                                366
```

<210> SEQ ID NO 152
<211> LENGTH: 366
<212> TYPE: DNA
<213> ORGANISM: artificial sequence
<220> FEATURE:
<223> OTHER INFORMATION: Antibody Sequence 152 ADI-30267 VH DNA

<400> SEQUENCE: 152

```
caggtgcagc tggtgcagtc tggggctgag gtgaagaagc ctggggcctc agtgaaggtt      60
tcctgcaagg catctggata caccttccgg agctactata tgagttgggt gcgacaggcc     120
cctggacaag gcttgagtg gatgggaata atcgatccta gtggtggtcg tacaagcttc      180
gcacaaaagt tccagggcag agtcaccatg accagggaca cgtccacgag cacagtctac     240
atggagctga gcagcctgag atctgaggac acggcggtgt actactgcgc aagggctaga     300
tacccagagt cttggccata cggaatggac gtatggggcc agggaacaac tgtcaccgtc     360
tcctca                                                                366
```

<210> SEQ ID NO 153
<211> LENGTH: 366
<212> TYPE: DNA
<213> ORGANISM: artificial sequence
<220> FEATURE:
<223> OTHER INFORMATION: Antibody Sequence 153 ADI-30268 VH DNA

<400> SEQUENCE: 153

```
caggtgcagc tggtgcagtc tggggctgag gtgaagaagc ctggggcctc agtgaaggtt      60
tcctgcaagg catctggata caccttcggg agctactata tggggtgggt gcgacaggcc     120
```

| | |
|---|---|
| cctggacaag ggcttgagtg gatgggaata atcgacccta gtggtggtag gacaagttac | 180 |
| gcacggaagt tccagggcag agtcaccatg accaggaca cgtccacgag cacagtctac | 240 |
| atggagctga gcagcctgag atctgaggac acggcggtgt actactgcgc aagggctcgt | 300 |
| acgccatcaa gctggccata cggaatggac gtatggggcc agggaacaac tgtcaccgtc | 360 |
| tcctca | 366 |

<210> SEQ ID NO 154
<211> LENGTH: 366
<212> TYPE: DNA
<213> ORGANISM: artificial sequence
<220> FEATURE:
<223> OTHER INFORMATION: Antibody Sequence 154 ADI-27243 VH DNA

<400> SEQUENCE: 154

| | |
|---|---|
| cagctgcagc tgcaggagtc gggcccagga ctggtgaagc cttcggagac cctgtccctc | 60 |
| acctgcactg tctctggtgg ctccatcagc agtagtcgct actactgggg ctggatccgc | 120 |
| cagcccccag ggaaggggct ggagtggatt gggagtatct attatagtgg gagcacctac | 180 |
| tacaacccgt ccctcaagag tcgagtcacc atatccgtag acacgtccaa gaaccagttc | 240 |
| tccctgaagc tgagttctgt gaccgccgca gacacggcgg tgtactactg cgccagagat | 300 |
| gggttgtacc acaccccaga atacttccaa cactggggac agggtacatt ggtcaccgtc | 360 |
| tcctca | 366 |

<210> SEQ ID NO 155
<211> LENGTH: 366
<212> TYPE: DNA
<213> ORGANISM: artificial sequence
<220> FEATURE:
<223> OTHER INFORMATION: Antibody Sequence 155 ADI-30302 VH DNA

<400> SEQUENCE: 155

| | |
|---|---|
| cagctgcagc tgcaggagtc gggcccagga ctggtgaagc cttcggagac cctgtccctc | 60 |
| acctgcactg tctctggtgg ctccatcggg agtagtcagt actactgggg ctggatccgc | 120 |
| cagcccccag ggaaggggct ggagtggatt gggagtatct atcgtagtgg ggggacctac | 180 |
| tacaacccgt ccctcaagag tcgagtcacc atatccgtag acacgtccaa gaaccagttc | 240 |
| tccctgaagc tgagttctgt gaccgccgca gacacggcgg tgtactactg cgccagagat | 300 |
| gggttgtacc acaccccaga atacttccaa cactggggac agggtacatt ggtcaccgtc | 360 |
| tcctca | 366 |

<210> SEQ ID NO 156
<211> LENGTH: 366
<212> TYPE: DNA
<213> ORGANISM: artificial sequence
<220> FEATURE:
<223> OTHER INFORMATION: Antibody Sequence 156 ADI-30336 VH DNA

<400> SEQUENCE: 156

| | |
|---|---|
| cagctgcagc tgcaggagtc gggcccagga ctggtgaagc cttcggagac cctgtccctc | 60 |
| acctgcactg tctctggtgg ctccatcagc agtagtcgct actactgggg ctggatccgc | 120 |
| cagcccccag ggaaggggct ggagtggatt gggagtatct attatagtgg gagcacctac | 180 |
| tacaacccgt ccctcaagag tcgagtcacc atatccgtag acacgtccaa gaaccagttc | 240 |
| tccctgaagc tgagttctgt gaccgccgca gacacggcgg tgtactactg cgccagagat | 300 |
| gggttgtacc acaccccaga atacttccaa cactggggac agggtacatt ggtcaccgtc | 360 | tcctca 366

<210> SEQ ID NO 157
<211> LENGTH: 366
<212> TYPE: DNA
<213> ORGANISM: artificial sequence
<220> FEATURE:
<223> OTHER INFORMATION: Antibody Sequence 157 ADI-27278 VH DNA

<400> SEQUENCE: 157

```
gaggtgcagc tggtggagtc tgggggaggc ttggtacagc ctgggggtc cctgagactc      60
tcctgtgcag cctctggatt caccttcagt agctatagca tgaactgggt ccgccaggct    120
ccagggaagg ggctggagtg ggtttcatac attagtggaa gtagtagtac catatactac    180
gcagactctg tgaagggccg attcaccatc tccagagaca tgccaagaa ctcactgtat     240
ctgcaaatga acagcctgag agccgaggac acggcggtgt actactgcgc cagacaccgc    300
atagcagact caccaagcag agccttcgat atatggggtc agggtacaat ggtcaccgtc    360
tcctca                                                               366
```

<210> SEQ ID NO 158
<211> LENGTH: 363
<212> TYPE: DNA
<213> ORGANISM: artificial sequence
<220> FEATURE:
<223> OTHER INFORMATION: Antibody Sequence 158 ADI-30293 VH DNA

<400> SEQUENCE: 158

```
gaggtgcagc tggtggagtc tgggggaggc ttggtacagc ctgggggtc cctgagactc      60
tcctgtgcag cctctggatt caccttcagt agctatagca tgaactgggt ccgccaggct    120
ccagggaagg gactggagtg ggtttcatac attagtagta gtgggaccat aaattacgca    180
gactctgtga agggccgatt caccatctcc agagacaatg ccaagaactc actgtatctg    240
caaatgaaca gcctgagagc cgaggacacg gcggtgtact actgcgccag acaccgcata    300
gcagactcac caagcagagc cttcgatata tggggtcagg gtacaatggt caccgtctcc    360
tca                                                                 363
```

<210> SEQ ID NO 159
<211> LENGTH: 363
<212> TYPE: DNA
<213> ORGANISM: artificial sequence
<220> FEATURE:
<223> OTHER INFORMATION: Antibody Sequence 159 ADI-30296 VH DNA

<400> SEQUENCE: 159

```
gaggtgcagc tggtggagtc tgggggaggc ttggtacagc ctgggggtc cctgagactc      60
tcctgtgcag cctctggatt caccatcggg ggttatagca tgaactgggt ccgccaggct    120
ccagggaagg ggctggagtg ggtttcatac attagtagta gtgtaccat acattacgca     180
gactctgtga agggccgatt caccatctcc agagacaatg ccaagaactc actgtatctg    240
caaatgaaca gcctgagagc tgaggacacg gcggtgtact actgcgccag acaccgcata    300
gggcgttcac caagcagagc cttcgatata tggggtcagg gtacaatggt caccgtctcc    360
tca                                                                 363
```

<210> SEQ ID NO 160
<211> LENGTH: 372
<212> TYPE: DNA

<213> ORGANISM: artificial sequence
<220> FEATURE:
<223> OTHER INFORMATION: Antibody Sequence 160 ADI-27291 VH DNA

<400> SEQUENCE: 160

| | | | | | |
|---|---|---|---|---|---|
| gaggtgcagc | tgttggagtc | tgggggaggc | ttggtacagc | ctgggggtc | cctgagactc | 60 |
| tcctgtgcag | cctctggatt | cacctttagc | agctatgcca | tgagctgggt | ccgccaggct | 120 |
| ccagggaagg | ggctggagtg | ggtctcagct | attagtggta | gtggtggtag | cacatactac | 180 |
| gcagactccg | tgaagggccg | gttcaccatc | tccagagaca | attccaagaa | cacgctgtat | 240 |
| ctgcaaatga | acagcctgag | agccgaggac | acggcggtgt | actactgcgc | caaggacccc | 300 |
| ggaacagaca | gcagcggcta | ctactacata | tggcgatact | ggggacaggg | tacattggtc | 360 |
| accgtctcct | ca | | | | | 372 |

<210> SEQ ID NO 161
<211> LENGTH: 372
<212> TYPE: DNA
<213> ORGANISM: artificial sequence
<220> FEATURE:
<223> OTHER INFORMATION: Antibody Sequence 161 ADI-30283 VH DNA

<400> SEQUENCE: 161

| | | | | | |
|---|---|---|---|---|---|
| gaggtgcagc | tgttggagtc | tgggggaggc | ttggtacagc | ctgggggtc | cctgagactc | 60 |
| tcctgtgcag | cctctggatt | cacctttagc | ccgtatggga | tgagctgggt | ccgccaggct | 120 |
| ccagggaagg | ggctggagtg | ggtctcaagt | attagtggaa | gtggtggtag | gacatactac | 180 |
| gcagactccg | tgaagggccg | gttcaccatc | tccagagaca | attccaagaa | cacgctgtat | 240 |
| ctgcaaatga | acagcctgag | agccgaggac | acggcggtgt | actactgcgc | caaggacccc | 300 |
| ggaacagaca | gcagcggcta | ctactacata | tggcgatact | ggggacaggg | tacattggtc | 360 |
| accgtctcct | ca | | | | | 372 |

<210> SEQ ID NO 162
<211> LENGTH: 372
<212> TYPE: DNA
<213> ORGANISM: artificial sequence
<220> FEATURE:
<223> OTHER INFORMATION: Antibody Sequence 162 ADI-30286 VH DNA

<400> SEQUENCE: 162

| | | | | | |
|---|---|---|---|---|---|
| gaggtgcagc | tgttggagtc | tgggggaggc | ttggtacagc | ctgggggtc | cctgagactc | 60 |
| tcctgtgcag | cctctggatt | cacctttggc | ccgtatggta | tgagctgggt | ccgccaggct | 120 |
| ccagggaagg | ggctggagtg | ggtctcagct | attagtggaa | gtggtgcgag | cacatggtac | 180 |
| gcagactccg | tgaagggccg | gttcaccatc | tccagagaca | actccaagaa | cacgctgtat | 240 |
| ctgcaaatga | acagcctgag | agccgaggac | acggcggtgt | actactgcgc | caaggacccc | 300 |
| ggaacacatt | atagcggcta | ctactacata | tggcgatact | ggggacaggg | tacattggtc | 360 |
| accgtctcct | ca | | | | | 372 |

<210> SEQ ID NO 163
<211> LENGTH: 372
<212> TYPE: DNA
<213> ORGANISM: artificial sequence
<220> FEATURE:
<223> OTHER INFORMATION: Antibody Sequence 163 ADI-30288 VH DNA

<400> SEQUENCE: 163

| | | | | | |
|---|---|---|---|---|---|
| gaggtgcagc | tgttggagtc | tgggggaggc | ttggtacagc | ctgggggtc | cctgagactc | 60 |

```
tcctgtgcag cctctggatt cacctttggc ccgtatggta tgagctgggt ccgccaggct    120
ccagggaagg ggctggagtg ggtctcagct attagtggaa gtggtgcgag cacatggcac    180
gcagactccg tgaagggccg gttcaccatc tccagagaca attccaagaa cacgctgtat    240
ctgcaaatga acagcctgag agccgaggac acggcggtgt actactgcgc caaggacccc    300
ggaacagaca gcactgggta ctactacata tggcgatact ggggacaggg tacattggtc    360
accgtctcct ca                                                        372
```

<210> SEQ ID NO 164
<211> LENGTH: 366
<212> TYPE: DNA
<213> ORGANISM: artificial sequence
<220> FEATURE:
<223> OTHER INFORMATION: Antibody Sequence 164 ADI-27297 VH DNA

<400> SEQUENCE: 164

```
caggtgcagc tggtgcagtc tggggctgag gtgaagaagc ctggggcctc agtgaaggtt    60
tcctgcaagg catctggata caccttcacc agctactata tgcactgggt gcgacaggcc    120
cctggacaag ggcttgagtg gatgggaata atcaaccctc gtggtggtag cacaagctac    180
gcacagaagt tccagggcag agtcaccatg accagggaca cgtccacgag cacagtctac    240
atggagctga gcagcctgag atctgaggac acggcggtgt actactgcgc aagagaccac    300
gacatagcag cagcaggaag attggctgat tactggggac agggtacatt ggtcaccgtc    360
tcctca                                                                366
```

<210> SEQ ID NO 165
<211> LENGTH: 366
<212> TYPE: DNA
<213> ORGANISM: artificial sequence
<220> FEATURE:
<223> OTHER INFORMATION: Antibody Sequence 165 ADI-30272 VH DNA

<400> SEQUENCE: 165

```
caggtgcagc tggtgcagtc tggggctgag gtgaagaagc ctggggcctc agtgaaggtt    60
tcctgcaagg catctggata caccttcacg gagtactata tgcactgggt gcgacaggcc    120
cctggacaag ggcttgagtg gatgggaata atctcgccta gtgcgggtag cacaagctac    180
gcacagaagt tccagggcag agtcaccatg accagggaca cgtccacgag cacagtctac    240
atggagctga gcagcctgag atctgaggac acggcggtgt actactgcgc aagagaccac    300
gacatagcag cagcaggaag attggctgat tactggggac agggtacatt ggtcaccgtc    360
tcctca                                                                366
```

<210> SEQ ID NO 166
<211> LENGTH: 366
<212> TYPE: DNA
<213> ORGANISM: artificial sequence
<220> FEATURE:
<223> OTHER INFORMATION: Antibody Sequence 166 ADI-30278 VH DNA

<400> SEQUENCE: 166

```
caggtgcagc tggtgcagtc tggggctgag gtgaagaagc ctggggcctc agtgaaggtt    60
tcctgcaagg catctggata caccttcacg gagtactata tgcactgggt gcgacaggcc    120
cctggacaag ggcttgagtg gatgggaata atctcgccta gtgcgggtag cacaaagtac    180
gcacagaagt tccagggcag agtcaccatg accagggaca cgtccacgag cacagtctac    240
```

```
atggagctga gcagcctgag atctgaggac acggcggtgt actactgcgc aagagaccac    300
gacatacgtc tggcaggaag attggctgat tactggggac agggtacatt ggtcaccgtc    360
tcctca                                                               366
```

<210> SEQ ID NO 167
<211> LENGTH: 369
<212> TYPE: DNA
<213> ORGANISM: artificial sequence
<220> FEATURE:
<223> OTHER INFORMATION: Antibody Sequence 167 ADI-27301 VH DNA

<400> SEQUENCE: 167

```
cagctgcagc tgcaggagtc gggcccagga ctggtgaagc cttcggagac cctgtccctc     60
acctgcactg tctctggtgg ctccatcagc agtagtagtt actactgggg ctggatccgc    120
cagcccccag gaaggggct ggagtggatt gggagtatct attatagtgg gagcacctac    180
tacaacccgt ccctcaagag tcgagtcacc atatccgtag acacgtccaa gaaccagttc    240
tccctgaagc tgagttctgt gaccgccgca gacacggcgg tgtactactg cgccagagaa    300
gccggacgcg gcaccactgg tctcttgttc gactactggg gacagggtac attggtcacc    360
gtctcctca                                                            369
```

<210> SEQ ID NO 168
<211> LENGTH: 369
<212> TYPE: DNA
<213> ORGANISM: artificial sequence
<220> FEATURE:
<223> OTHER INFORMATION: Antibody Sequence 168 ADI-30306 VH DNA

<400> SEQUENCE: 168

```
cagctgcagc tgcaggagtc gggcccagga ctggtgaagc cttcggagac cctgtccctc     60
acctgcactg tctctggtgg ctccatcagc agtagtcttt actactgggg ctggatccgc    120
cagcccccag gaaggggct ggagtggatt gggtctatct attatagtgg gagcacctttt    180 tacaacccgt ccttcaagag tcgagtcacc atatccgtag acacgtccaa gaaccagttc    240
tccctgaagc tgagttctgt gaccgccgca gacacggcgg tgtactactg cgccagagaa    300
gccggacgcg gcaccactgg tctcttgttc gactactggg gacagggtac attggtcacc    360
gtctcctca                                                            369
```

<210> SEQ ID NO 169
<211> LENGTH: 369
<212> TYPE: DNA
<213> ORGANISM: artificial sequence
<220> FEATURE:
<223> OTHER INFORMATION: Antibody Sequence 169 ADI-30311 VH DNA

<400> SEQUENCE: 169

```
cagctgcagc tgcaggagtc gggcccagga ctggtgaagc cttcggagac cctgtccctc     60
acctgcactg tctctggtgg ctccatcgcg agtagtgttt actactgggg ctggatccgc    120
cagcccccag gaaggggct ggagtggatt gggagtatct attatagtgg gagcacctgg    180
tacaacccgt ccctcaagag tcgagtcacc atatccgtag acacgtccaa gaaccagttc    240
tccctgaagc tgagttctgt gaccgccgca gacacggcgg tgtactactg cgccagagaa    300
gccggacgca ctgggactgg tctcttgttc gactactggg gacagggtac attggtcacc    360
gtctcctca                                                            369
```

```
<210> SEQ ID NO 170
<211> LENGTH: 321
<212> TYPE: DNA
<213> ORGANISM: artificial sequence
<220> FEATURE:
<223> OTHER INFORMATION: Antibody Sequence 170 ADI-27238, ADI-30263,
      ADI-30267, ADI-30268 VL DNA

<400> SEQUENCE: 170
gacatccaga tgacccagtc tccatcctcc ctgtctgcat ctgtaggaga cagagtcacc    60
atcacttgcc gggcaagtca gagcattaac agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcaa agcctcctca ctcctttcac ttttggcgga   300
gggaccaagg ttgagatcaa a                                              321

<210> SEQ ID NO 171
<211> LENGTH: 321
<212> TYPE: DNA
<213> ORGANISM: artificial sequence
<220> FEATURE:
<223> OTHER INFORMATION: Antibody Sequence 171 ADI-27243, ADI-30302 VL
      DNA

<400> SEQUENCE: 171
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag agattcgcct tcccttacac ttttggcgga   300
gggaccaagg ttgagatcaa a                                              321

<210> SEQ ID NO 172
<211> LENGTH: 321
<212> TYPE: DNA
<213> ORGANISM: artificial sequence
<220> FEATURE:
<223> OTHER INFORMATION: Antibody Sequence 172 ADI-30336 VL DNA

<400> SEQUENCE: 172
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag agattcgccc atccttacac ttttggcgga   300
gggaccaagg ttgagatcaa a                                              321

<210> SEQ ID NO 173
<211> LENGTH: 336
<212> TYPE: DNA
<213> ORGANISM: artificial sequence
<220> FEATURE:
<223> OTHER INFORMATION: Antibody Sequence 173 ADI-27278, ADI-30293,
      ADI-30296 VL DNA

<400> SEQUENCE: 173
gacatcgtga tgacccagtc tccagactcc ctggctgtgt ctctgggcga gagggccacc    60
```

```
atcaactgca agtccagcca gagtgtttta ttcagctcca acaataagaa ctacttagct    120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtgcaa gtttattact gtcagcagtc ctacttcttc    300
cctacttttg gcggagggac caaggttgag atcaaa                              336
```

<210> SEQ ID NO 174
<211> LENGTH: 324
<212> TYPE: DNA
<213> ORGANISM: artificial sequence
<220> FEATURE:
<223> OTHER INFORMATION: Antibody Sequence 174 ADI-27291, ADI-30283,
      ADI-30286, ADI-30288 VL DNA

<400> SEQUENCE: 174

```
gaaatagtga tgacgcagtc tccagccacc ctgtctgtgt ctccagggga aagagccacc     60
ctctcctgca gggccagtca gagtgttagc agcaacttag cctggtacca gcagaaacct    120
ggccaggctc ccaggctcct catctatagc gcatccacca gggccactgg tatcccagcc    180
aggttcagtg gcagtgggtc tgggacagag ttcactctca ccatcagcag cctgcagtct    240
gaagattttg cagtttatta ctgtcagcag tacgtccccc accctccttt cacttttggc    300
ggagggacca aggttgagat caaa                                            324
```

<210> SEQ ID NO 175
<211> LENGTH: 321
<212> TYPE: DNA
<213> ORGANISM: artificial sequence
<220> FEATURE:
<223> OTHER INFORMATION: Antibody Sequence 175 ADI-27297, ADI-30272,
      ADI-30278 VL DNA

<400> SEQUENCE: 175

```
gacatccaga tgacccagtc tccatcttcc gtgtctgcat ctgtaggaga cagagtcacc     60
atcacttgtc gggcgagtca gggtattagc agctggttag cctggtatca gcagaaacca    120
gggaaagccc ctaagctcct gatctccgct gcatccagtt tgcaaagtgg ggtcccatca    180
aggttcagcg gcagtggatc tgggacagat ttcactctca ccatcagcag cctgcagcct    240
gaagattttg caacttatta ctgtcagcag cagtcatcc tccctatcac ttttggcgga    300
gggaccaagg ttgagatcaa a                                               321
```

<210> SEQ ID NO 176
<211> LENGTH: 321
<212> TYPE: DNA
<213> ORGANISM: artificial sequence
<220> FEATURE:
<223> OTHER INFORMATION: Antibody Sequence 176 ADI-27301, ADI-30306,
      ADI-30311 VL DNA

<400> SEQUENCE: 176

```
gacatccaga tgacccagtc tccttccacc ctgtctgcat ctgtaggaga cagagtcacc     60
atcacttgcc gggccagtca gagtattagt agctggttgg cctggtatca gcagaaacca    120
gggaaagccc ctaagctcct gatctataaa gcctccagtt tggaaagtgg ggtcccatca    180
aggttcagcg gcagtggatc tgggacagaa ttcactctca ccatcagcag cctgcagcct    240
gatgattttg caacttatta ctgccagcag tacggcatcc tccctaggac ttttggcgga    300
gggaccaagg ttgagatcaa a                                               321
```

<210> SEQ ID NO 177
<211> LENGTH: 327
<212> TYPE: PRT
<213> ORGANISM: artificial sequence
<220> FEATURE:
<223> OTHER INFORMATION: Antibody 177 Heavy chain constant region
      (IgG4_PAA)
<220> FEATURE:
<221> NAME/KEY: misc_feature
<222> LOCATION: (327)..(327)
<223> OTHER INFORMATION: Xaa may be any natural amino acid, and
      preferably Xaa is lysine or is deleted

<400> SEQUENCE: 177

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Xaa
                325

<210> SEQ ID NO 178
<211> LENGTH: 10
<212> TYPE: PRT
<213> ORGANISM: artificial sequence
<220> FEATURE:
<223> OTHER INFORMATION: Antibody Sequence 178 ADI-27238 HCDR1-AbM

<400> SEQUENCE: 178

Gly Tyr Thr Phe Thr Ser Tyr Tyr Met Ser
1               5                   10

<210> SEQ ID NO 179
<211> LENGTH: 10
<212> TYPE: PRT
<213> ORGANISM: artificial sequence
<220> FEATURE:
<223> OTHER INFORMATION: Antibody Sequence 179 ADI-30263 HCDR1-AbM

<400> SEQUENCE: 179

Gly Tyr Thr Phe Leu Ser Tyr Tyr Met Asn
1               5                   10

<210> SEQ ID NO 180
<211> LENGTH: 10
<212> TYPE: PRT
<213> ORGANISM: artificial sequence
<220> FEATURE:
<223> OTHER INFORMATION: Antibody Sequence 180 ADI-30267 HCDR1-AbM

<400> SEQUENCE: 180

Gly Tyr Thr Phe Arg Ser Tyr Tyr Met Ser
1               5                   10

<210> SEQ ID NO 181
<211> LENGTH: 10
<212> TYPE: PRT
<213> ORGANISM: artificial sequence
<220> FEATURE:
<223> OTHER INFORMATION: Antibody Sequence 181 ADI-30268 HCDR1-AbM

<400> SEQUENCE: 181

Gly Tyr Thr Phe Gly Ser Tyr Tyr Met Gly
1               5                   10

<210> SEQ ID NO 182
<211> LENGTH: 13
<212> TYPE: PRT
<213> ORGANISM: artificial sequence
<220> FEATURE:
<223> OTHER INFORMATION: Antibody Sequence 182 ADI-27238 HCDR3-Kabat

<400> SEQUENCE: 182

Ala Arg Tyr Pro Ser Ser Trp Pro Tyr Gly Met Asp Val
1               5                   10

<210> SEQ ID NO 183
<211> LENGTH: 13
<212> TYPE: PRT
<213> ORGANISM: artificial sequence
<220> FEATURE:
<223> OTHER INFORMATION: Antibody Sequence 183 ADI-30263 HCDR3-Kabat

<400> SEQUENCE: 183

Ala Arg Tyr Pro Ser Ser Trp Pro Tyr Gly Thr Asp Val
1               5                   10

<210> SEQ ID NO 184
<211> LENGTH: 13
<212> TYPE: PRT
<213> ORGANISM: artificial sequence
<220> FEATURE:
<223> OTHER INFORMATION: Antibody Sequence 184 ADI-30267 HCDR3-Kabat

<400> SEQUENCE: 184

Ala Arg Tyr Pro Glu Ser Trp Pro Tyr Gly Met Asp Val
1               5                   10

<210> SEQ ID NO 185
<211> LENGTH: 13
<212> TYPE: PRT
<213> ORGANISM: artificial sequence
<220> FEATURE:
<223> OTHER INFORMATION: Antibody Sequence 185 ADI-30268 HCDR3-Kabat

<400> SEQUENCE: 185

Ala Arg Thr Pro Ser Ser Trp Pro Tyr Gly Met Asp Val
1               5                   10

<210> SEQ ID NO 186
<211> LENGTH: 12
<212> TYPE: PRT
<213> ORGANISM: artificial sequence
<220> FEATURE:
<223> OTHER INFORMATION: Antibody Sequence 186 ADI-27243, ADI-30336
       HCDR1-AbM

<400> SEQUENCE: 186

Gly Gly Ser Ile Ser Ser Ser Arg Tyr Tyr Trp Gly
1               5                   10

<210> SEQ ID NO 187
<211> LENGTH: 12
<212> TYPE: PRT
<213> ORGANISM: artificial sequence
<220> FEATURE:
<223> OTHER INFORMATION: Antibody Sequence 187 ADI-30302 HCDR1-AbM

<400> SEQUENCE: 187

Gly Gly Ser Ile Gly Ser Ser Gln Tyr Tyr Trp Gly
1               5                   10

<210> SEQ ID NO 188
<211> LENGTH: 12
<212> TYPE: PRT
<213> ORGANISM: artificial sequence
<220> FEATURE:
<223> OTHER INFORMATION: Antibody Sequence 188 ADI-27243, ADI-30302,
       ADI-30336 HCDR3-Kabat

<400> SEQUENCE: 188

Asp Gly Leu Tyr His Thr Pro Glu Tyr Phe Gln His
1               5                   10

<210> SEQ ID NO 189
<211> LENGTH: 10
<212> TYPE: PRT
<213> ORGANISM: artificial sequence
<220> FEATURE:
<223> OTHER INFORMATION: Antibody Sequence 189 ADI-27278, ADI-30293
       HCDR1-AbM

<400> SEQUENCE: 189

Gly Phe Thr Phe Ser Ser Tyr Ser Met Asn

-continued

```
1               5                   10

<210> SEQ ID NO 190
<211> LENGTH: 10
<212> TYPE: PRT
<213> ORGANISM: artificial sequence
<220> FEATURE:
<223> OTHER INFORMATION: Antibody Sequence 190 ADI-30296 HCDR1-AbM

<400> SEQUENCE: 190

Gly Phe Thr Ile Gly Gly Tyr Ser Met Asn
1               5                   10

<210> SEQ ID NO 191
<211> LENGTH: 13
<212> TYPE: PRT
<213> ORGANISM: artificial sequence
<220> FEATURE:
<223> OTHER INFORMATION: Antibody Sequence 191 ADI-27278, ADI-30293
      HCDR3-Kabat

<400> SEQUENCE: 191

His Arg Ile Ala Asp Ser Pro Ser Arg Ala Phe Asp Ile
1               5                   10

<210> SEQ ID NO 192
<211> LENGTH: 13
<212> TYPE: PRT
<213> ORGANISM: artificial sequence
<220> FEATURE:
<223> OTHER INFORMATION: Antibody Sequence 192 ADI-30296 HCDR3-Kabat

<400> SEQUENCE: 192

His Arg Ile Gly Arg Ser Pro Ser Arg Ala Phe Asp Ile
1               5                   10

<210> SEQ ID NO 193
<211> LENGTH: 10
<212> TYPE: PRT
<213> ORGANISM: artificial sequence
<220> FEATURE:
<223> OTHER INFORMATION: Antibody Sequence 193 ADI-27291 HCDR1-AbM

<400> SEQUENCE: 193

Gly Phe Thr Phe Ser Ser Tyr Ala Met Ser
1               5                   10

<210> SEQ ID NO 194
<211> LENGTH: 10
<212> TYPE: PRT
<213> ORGANISM: artificial sequence
<220> FEATURE:
<223> OTHER INFORMATION: Antibody Sequence 194 ADI-30283 HCDR1-AbM

<400> SEQUENCE: 194

Gly Phe Thr Phe Ser Pro Tyr Gly Met Ser
1               5                   10

<210> SEQ ID NO 195
<211> LENGTH: 10
<212> TYPE: PRT
<213> ORGANISM: artificial sequence
<220> FEATURE:
<223> OTHER INFORMATION: Antibody Sequence 195 ADI-30286, ADI-30288
      HCDR1-AbM

<400> SEQUENCE: 195
```

```
Gly Phe Thr Phe Gly Pro Tyr Gly Met Ser
1               5                   10

<210> SEQ ID NO 196
<211> LENGTH: 15
<212> TYPE: PRT
<213> ORGANISM: artificial sequence
<220> FEATURE:
<223> OTHER INFORMATION: Antibody Sequence 196 ADI-27291, ADI-30283
      HCDR3-Kabat

<400> SEQUENCE: 196

Asp Pro Gly Thr Asp Ser Ser Gly Tyr Tyr Tyr Ile Trp Arg Tyr
1               5                   10                  15

<210> SEQ ID NO 197
<211> LENGTH: 15
<212> TYPE: PRT
<213> ORGANISM: artificial sequence
<220> FEATURE:
<223> OTHER INFORMATION: Antibody Sequence 197 ADI-30286 HCDR3-Kabat

<400> SEQUENCE: 197

Asp Pro Gly Thr His Tyr Ser Gly Tyr Tyr Tyr Ile Trp Arg Tyr
1               5                   10                  15

<210> SEQ ID NO 198
<211> LENGTH: 15
<212> TYPE: PRT
<213> ORGANISM: artificial sequence
<220> FEATURE:
<223> OTHER INFORMATION: Antibody Sequence 198 ADI-30288 HCDR3-Kabat

<400> SEQUENCE: 198

Asp Pro Gly Thr Asp Ser Thr Gly Tyr Tyr Tyr Ile Trp Arg Tyr
1               5                   10                  15

<210> SEQ ID NO 199
<211> LENGTH: 10
<212> TYPE: PRT
<213> ORGANISM: artificial sequence
<220> FEATURE:
<223> OTHER INFORMATION: Antibody Sequence 199 ADI-27297 HCDR1-AbM

<400> SEQUENCE: 199

Gly Tyr Thr Phe Thr Ser Tyr Tyr Met His
1               5                   10

<210> SEQ ID NO 200
<211> LENGTH: 10
<212> TYPE: PRT
<213> ORGANISM: artificial sequence
<220> FEATURE:
<223> OTHER INFORMATION: Antibody Sequence 200 ADI-30272, ADI-30278
      HCDR1-AbM

<400> SEQUENCE: 200

Gly Tyr Thr Phe Thr Glu Tyr Tyr Met His
1               5                   10

<210> SEQ ID NO 201
<211> LENGTH: 13
<212> TYPE: PRT
<213> ORGANISM: artificial sequence
<220> FEATURE:
<223> OTHER INFORMATION: Antibody Sequence 201 ADI-27297, ADI-30272
      HCDR3-Kabat
```

```
<400> SEQUENCE: 201

Asp His Asp Ile Ala Ala Ala Gly Arg Leu Ala Asp Tyr
1               5                   10

<210> SEQ ID NO 202
<211> LENGTH: 13
<212> TYPE: PRT
<213> ORGANISM: artificial sequence
<220> FEATURE:
<223> OTHER INFORMATION: Antibody Sequence 202 ADI-30278 HCDR3-Kabat

<400> SEQUENCE: 202

Asp His Asp Ile Arg Leu Ala Gly Arg Leu Ala Asp Tyr
1               5                   10

<210> SEQ ID NO 203
<211> LENGTH: 12
<212> TYPE: PRT
<213> ORGANISM: artificial sequence
<220> FEATURE:
<223> OTHER INFORMATION: Antibody Sequence 203 ADI-27301 HCDR1-AbM

<400> SEQUENCE: 203

Gly Gly Ser Ile Ser Ser Ser Ser Tyr Tyr Trp Gly
1               5                   10

<210> SEQ ID NO 204
<211> LENGTH: 12
<212> TYPE: PRT
<213> ORGANISM: artificial sequence
<220> FEATURE:
<223> OTHER INFORMATION: Antibody Sequence 204 ADI-30306 HCDR1-AbM

<400> SEQUENCE: 204

Gly Gly Ser Ile Ser Ser Ser Leu Tyr Tyr Trp Gly
1               5                   10

<210> SEQ ID NO 205
<211> LENGTH: 12
<212> TYPE: PRT
<213> ORGANISM: artificial sequence
<220> FEATURE:
<223> OTHER INFORMATION: Antibody Sequence 205 ADI-30311 HCDR1-AbM

<400> SEQUENCE: 205

Gly Gly Ser Ile Ala Ser Ser Val Tyr Tyr Trp Gly
1               5                   10

<210> SEQ ID NO 206
<211> LENGTH: 13
<212> TYPE: PRT
<213> ORGANISM: artificial sequence
<220> FEATURE:
<223> OTHER INFORMATION: Antibody Sequence 206 ADI-27301, ADI-30306
      HCDR3-Kabat

<400> SEQUENCE: 206

Glu Ala Gly Arg Gly Thr Thr Gly Leu Leu Phe Asp Tyr
1               5                   10

<210> SEQ ID NO 207
<211> LENGTH: 13
<212> TYPE: PRT
<213> ORGANISM: artificial sequence
<220> FEATURE:
<223> OTHER INFORMATION: Antibody Sequence 207 ADI-30311 HCDR3-Kabat
```

<400> SEQUENCE: 207

Glu Ala Gly Arg Thr Gly Thr Gly Leu Leu Phe Asp Tyr
1               5                   10

<210> SEQ ID NO 208
<211> LENGTH: 244
<212> TYPE: PRT
<213> ORGANISM: artificial sequence
<220> FEATURE:
<223> OTHER INFORMATION: Sequence 208 Human TIGIT sequence

<400> SEQUENCE: 208

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 209
<211> LENGTH: 107
<212> TYPE: PRT
<213> ORGANISM: artificial sequence
<220> FEATURE:
<223> OTHER INFORMATION: Antibody Sequence 209 Light chain constant
      region (? light chain)

<400> SEQUENCE: 209

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

```
Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

ANTI-TIGIT ANTIBODY AND USE THEREOF

TECHNICAL FIELD

The present invention relates to a novel antibody and an antibody fragment thereof that specifically bind to TIGIT and a composition comprising the antibody or the antibody fragment. In addition, the present invention relates to a nucleic acid encoding the antibody or the antibody fragment thereof, a host cell comprising the nucleic acid, and related use. Furthermore, the present invention relates to therapeutic and diagnostic use of the antibody and the antibody fragment.

BACKGROUND

TIGIT (a T-cell immune receptor comprising Ig and ITIM domains, also known as WUCAM, Vstm3, or Vsig9) is originally discovered as a member of the CD28 family by comparison in bioinformatics. TIGIT is a co-inhibitory receptor expressed on the membrane surface of various immune cells (natural killer cells/activated T cells/memory T cells/regulatory T cells/follicular T-helper cells, etc.) and is a member of the immunoglobulin superfamily. It is believed that TIGIT molecules may exert a regulating effect on the immune system through three mechanisms: 1) TIGIT competes with a co-stimulatory receptor CD226 for binding to the shared ligand CD155/CD112 expressed on the surface of dendritic or cancer cells, and transmits inhibitory signals to cells expressing TIGIT so as to inhibit activation of such cells; 2) TIGIT interacts directly with the co-stimulatory receptor CD226 to disrupt homodimerization of CD226 and block its activation signal transmitted downstream; 3) after TIGIT binds to CD155 expressed in dendritic cells, the intracellular ITIM sequence transmits inhibitory signals so as to express immunosuppressive cytokines to inhibit the activation of the immune system. TIGIT may play a role in a variety of cells in the tumor microenvironment. These cells may be tumor-infiltrating $CD8^+$ T cells, regulatory T cells, and NK cells as well. Overall, numerous studies suggest that the first mechanism is probably the most critical mechanism for TIGIT to exert its immunosuppressive effects.

An antibody binding to human TIGIT has been demonstrated to be useful for treating cancers. See, for example, WO 2006/124667. Antibody blockade of PD-L1 and TIGIT can increase the $CD8^+$ T cell-mediated tumor rejection in a synergistic manner in a mouse model. Grogan et al. (2014) *J. Immunol.* 192(1) Suppl. 203.15; Johnston et al. (2014) *Cancer Cell* 26:1-15. Similar results are obtained in an animal model of melanoma. Inozume et al. (2014) *J. Invest. Dermatol.* 134:S121-Abstract 693.

In view of its role in immune responses, TIGIT is considered an attractive cancer immunotherapy target. Accordingly, there is a need in the art to develop new TIGIT antibodies, particularly CD155/CD112 blocking antibodies targeting TIGIT, more particularly human anti-TIGIT antibodies, and combination therapies thereof, for disease treatments, particularly cancer treatments.

SUMMARY OF THE INVENTION

The present invention provides an anti-TIGIT antibody, a coding gene thereof, and use thereof. Through the genetic engineering and yeast display, the inventor screened a fully humanized anti-human-TIGIT antibody from a human antibody library displayed on the surface of yeasts, and further obtained an affinity-matured high-affinity anti-human TIGIT antibody. The fully humanized antibody molecule of the present invention can effectively block the binding of TIGIT to its ligand CD155, reduce or eliminate inhibitory signals transmitted to cells, increase the production of IL-2, and inhibit the tumor growth when administered in vivo, the tumor inhibition effect of which is particularly outstanding when administered in combination with an anti-PD-1 antibody. Therefore, the antibody of the present invention can be used for multiple purposes, including but not limited to enhancing immunization reactions, inhibiting tumor growths, resisting infections, and detecting TIGIT proteins.

The present invention provides a novel fully humanized antibody binding to human TIGIT, and an antigen-binding fragment thereof.

In some embodiments, the anti-TIGIT antibody of the present invention has one or more of the following properties:
(i) capacity of binding to human TIGIT with high affinity;
(ii) activity of cross-immunoreaction with monkey and/or murine TIGIT;
(iii) effectively binding to TIGIT on cell surface;
(iv) blocking the binding of TIGIT to its ligand CD155;
(v) relieving the inhibition effect of the binding of CD155 to TIGIT on an IL-2 signaling pathway downstream of TIGIT;
(vi) increasing IL-2 production in T cells;
(vii) anti-tumor activity, e.g., inhibiting tumor growth;
(viii) having better tumor inhibitory effect in combination with anti-PD-1 antibody, e.g., better inhibiting tumor growth.

In some embodiments, the present invention provides an antibody or antigen-binding fragment thereof that binds to TIGIT, comprising: HCDR1, HCDR2, and HCDR3 sequences of one of the heavy chain variable regions set forth in SEQ ID NOs: 84-103, and/or LCDR1, LCDR2, and LCDR3 sequences of the light chain variable regions set forth in SEQ ID NOs: 104-110, or a variant of a combination of the CDR sequences described above.

In some embodiments, the present invention also provides an anti-TIGIT antibody or an antigen-binding fragment thereof. The anti-TIGIT antibody and an exemplary antibody (e.g., an antibody having a combination of the antibody VH and VL sequences of listed in Table B) of the present invention bind to the same or an overlapping epitope and/or compete for binding to TIGIT, and/or the anti-TIGIT antibody inhibits (e.g., competitively inhibits) the exemplary antibody of the present invention.

In some embodiments, the present invention provides a nucleic acid encoding the antibody or the antigen-binding fragment thereof disclosed herein, a vector comprising the nucleic acid, and a host cell comprising the vector.

In some embodiments, the present invention provides a method for preparing the antibody or the antigen-binding fragment thereof disclosed herein.

In some embodiments, the present invention provides an immunoconjugate, a pharmaceutical composition, and a combination product comprising the antibody of the present invention.

The present invention also provides a method for blocking the binding of TIGIT to CD155 (e.g., CD155 expressed on the surface of a dendritic cell or a cancer cell) in a subject using the antibody of the present invention. In some embodiments, TIGIT-mediated inhibitory signaling is reduced or eliminated in cells (particularly T cells, natural killer cells) expressing TIGIT by the method, so as to stimulate the activation of T cells and NK cells. In some embodiments, the production of IL-2 in T cells is increased by the method. In some embodiments, CD155-mediated inhibitory signaling is reduced in cells (e.g., dendritic cells) expressing CD155 by the method, so as to reduce the expression of immunosuppressive cytokines. In some embodiments, the activation of the immune system is promoted by the method. Accordingly, the present invention also provides a method for preventing or treating a cancer or an infection using the antibody of the present invention.

The present invention also relates to a method for detecting TIGIT in a sample.

The present invention is further illustrated in the following drawings and specific embodiments. However, these drawings and specific embodiments should not be construed as limiting the scope of the invention, and modifications easily conceived by those skilled in the art will be included in the spirit of the present invention and the protection scope of the appended claims.

BRIEF DESCRIPTION OF THE DRAWINGS

FIG. 9 shows an exemplary human TIGIT sequence used in examples of the present invention.

DETAILED DESCRIPTION

Definitions

Figure 1A:
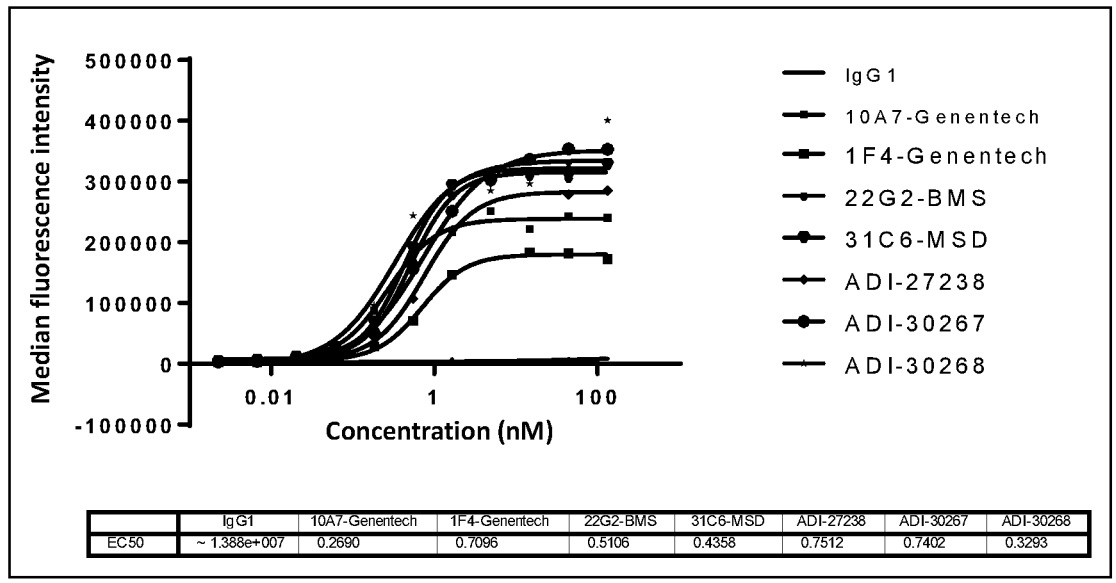
FIGS. 1A-F show the binding of antibodies expressed by yeasts to human TIGIT expressed on the surface of CHO cells before and after affinity maturation.
Figure 1B:
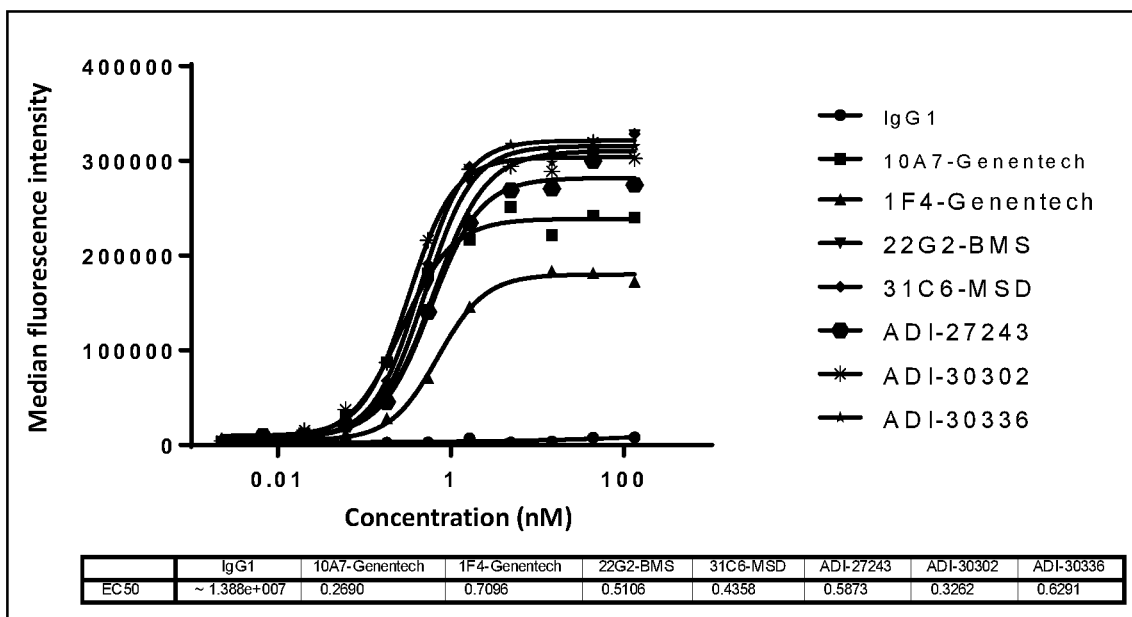
Figure 1C:
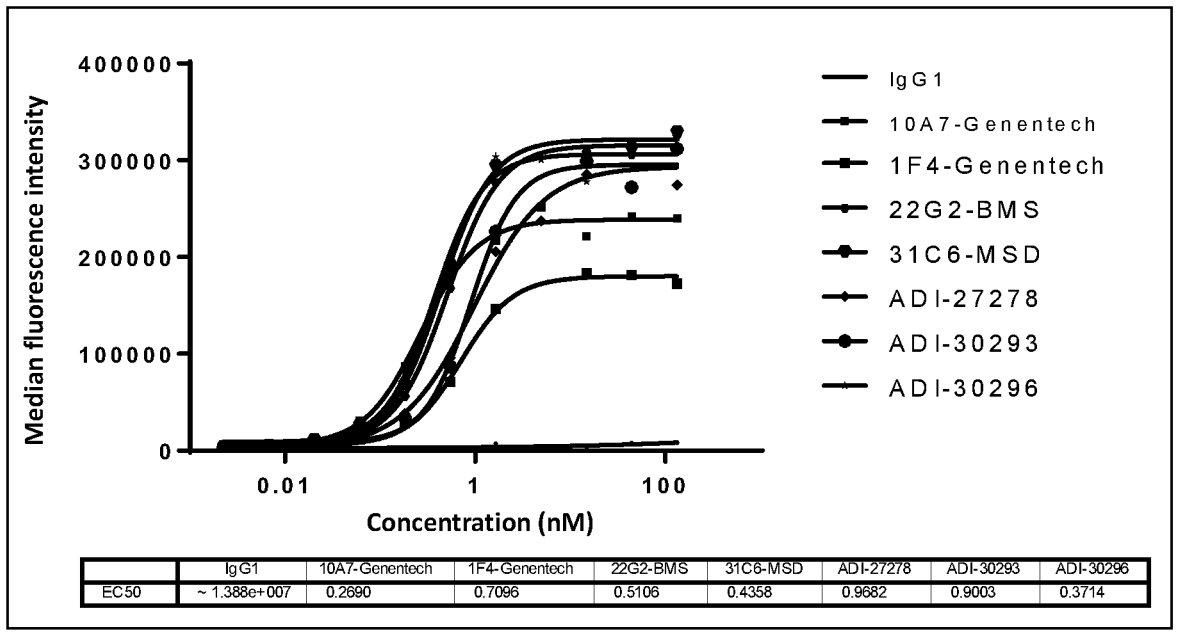
Figure 1D:
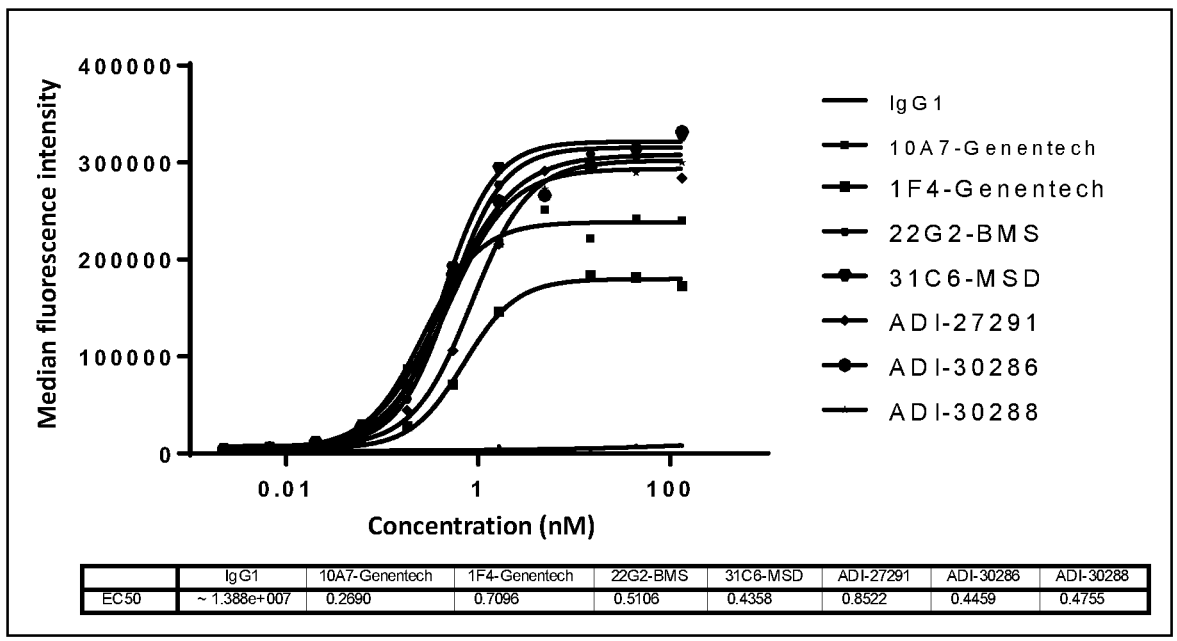
Figure 1E:
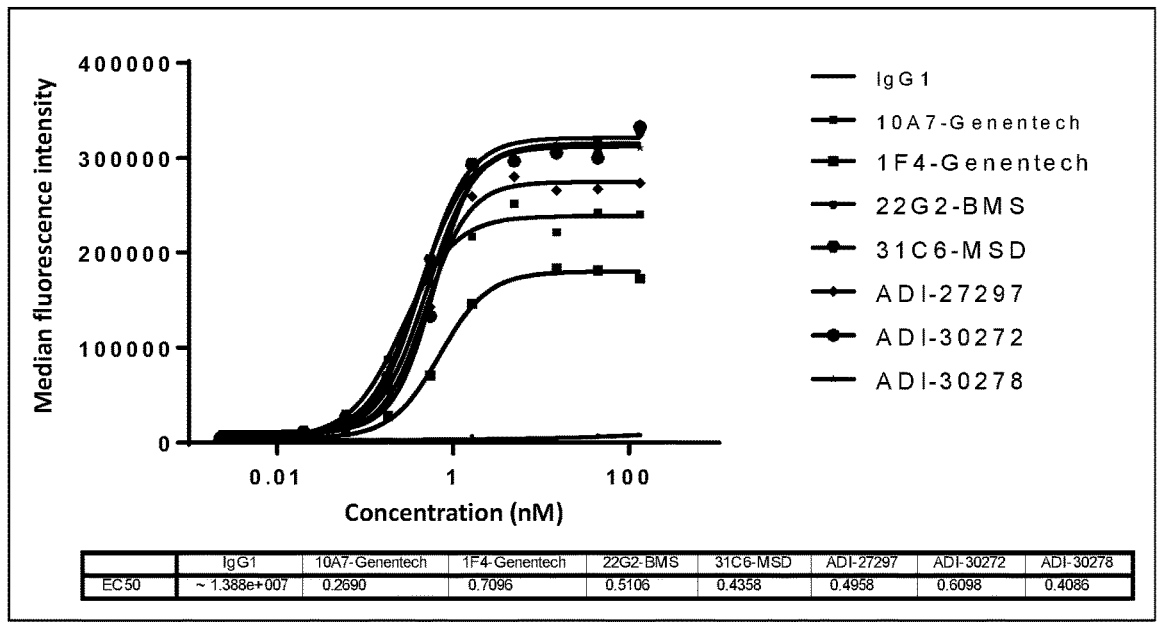
Figure 1F:
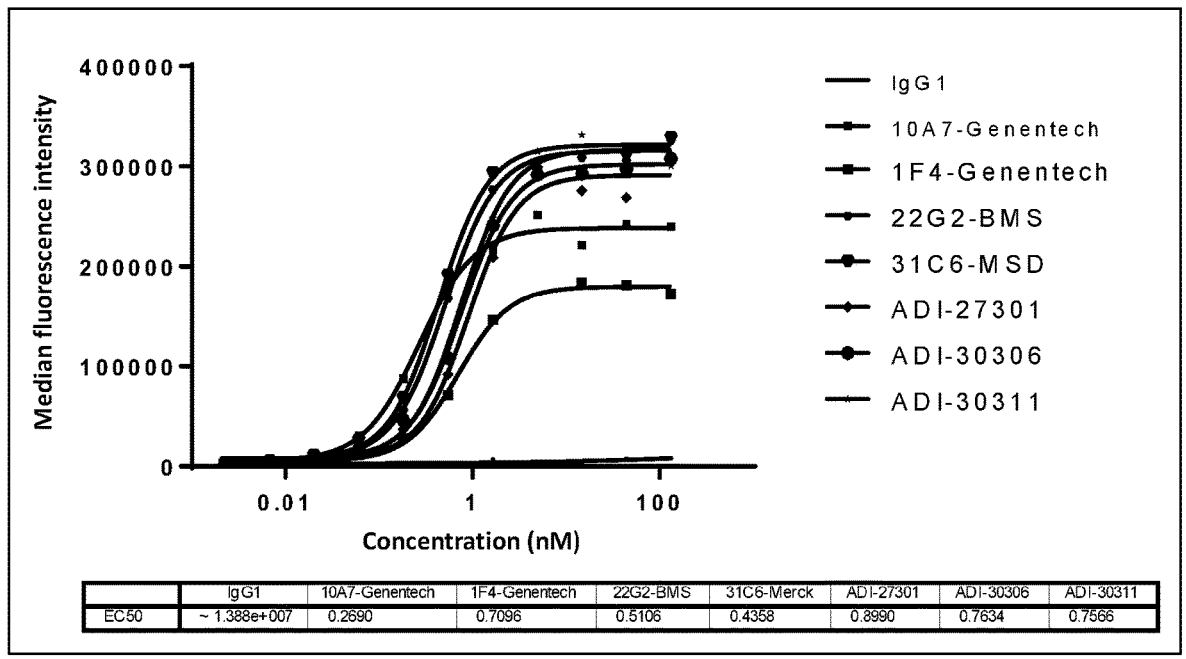

Unless otherwise defined, all technical and scientific terms used herein have the same meaning as those commonly understood by those of ordinary skill in the art. For the purposes of the present invention, the following terms are defined below.

The term "about" used in combination with a numerical value is intended to encompass the numerical values in a range from a lower limit less than the specified numerical value by 5% to an upper limit greater than the specified numerical value by 5%.

The term "and/or" should be understood to refer to any one of the options or any two or more of the options.

As used herein, the term "comprise" or "include" is intended to mean that the elements, integers or steps are included, but not to the exclusion of any other elements, integers or steps. As used herein, the term "comprise" or "include", unless indicated otherwise, also encompasses the situation where the entirety consists of the described elements, integers or steps. For example, when referring to "comprise" an antibody variable region of a particular sequence, it is also intended to encompass an antibody variable region consisting of the particular sequence.

As used herein, the term "antibody" refers to a polypeptide comprising at least an immunoglobulin light chain variable region or heavy chain variable region that specifically recognizes and binds to an antigen. The term "antibody" encompasses a variety of antibody structures, including but not limited to, monoclonal antibodies, polyclonal antibodies, single-chain or multi-chain antibodies, monospecific or multispecific antibodies (e.g., bispecific antibodies), fully human or chimeric or humanized antibodies, and full-length antibodies and antibody fragments, so long as they exhibit the desired antigen-binding activity.

It will be appreciated by those skilled in the art that a "whole antibody" (used interchangeably herein with "full-length antibody", "complete antibody" and "intact antibody") comprises at least two heavy chains (Hs) and two light chains (Ls). Each heavy chain consists of a heavy chain variable region (abbreviated herein as VH) and a heavy chain constant region. The heavy chain constant region consists of 3 domains CH1, CH2 and CH3. Each light chain consists of a light chain variable region (abbreviated herein as VL) and a light chain constant region. The light chain constant region consists of a domain CL. The variable regions are domains in the heavy chains or light chains of antibodies that participate in binding of the antibodies to the antigens thereof. The constant regions are not directly involved in binding of antibodies to antigens, but exhibit a variety of effector functions. The light chains of an antibody can be assigned to one of two types, kappa (κ) and lambda (λ), based on the amino acid sequence of a constant domain thereof. Depending on the amino acid sequence of the heavy chain constant region, the heavy chains of an antibody can be divided into 5 major types, i.e. IgA, IgD, IgE, IgG, and IgM, several of which can be further divided into subtypes, e.g. IgG1, IgG2, IgG3, IgG4, IgA1, and IgA2. The heavy chain constant regions corresponding to the 5 different antibody types are called α, δ, ε, γ, and μ respectively. The term "isotype" refers to an antibody type determined by the heavy chain constant region of the antibody. See, for example, *Fundamental Immunology*, Ch. 7 (Paul, w. Eds., 2nd edition, Raven Press, N.Y. (1989)) which is incorporated herein by reference in its entirety for all purposes.

The term "antigen-binding portion" (used interchangeably herein with "antibody fragment" and "antigen-binding fragment") of the antibody refers to an incomplete antibody molecule that comprises a portion of an intact antibody for binding to an antigen to which the intact antibody binds. It will be understood by those skilled in the art that the antigen-binding portion of an antibody generally comprises amino acid residues from a "complementarity determining region" or a "CDR". An antigen-binding fragment may be prepared by recombinant DNA techniques, or by enzymatic or chemical cleavage of an intact antibody. The antigen-binding fragment includes, but is not limited to, a Fab, an scFab, a Fab', an F(ab')$_2$, a Fab'-SH, an Fv, a single-chain Fv, a diabody, a triabody, a tetrabody, a minibody, and a single-domain antibody (sdAb). For more detailed descriptions of the antibody fragment, see: *Fundamental Immunology*, W. E. Paul eds., Raven Press, N.Y. (1993); Shao Rongguang et al. (eds.), *Antibody Drug Research and Application*, People's Medical Publishing House (2013); Hollinger et al., *PNAS* USA 90: 6444-6448 (1993); Hudson et al., *Nat. Med.* 9:129-134 (2003).

The terms "human antibody" and "fully humanized antibody" are used interchangeably herein and refer to an antibody comprising variable regions in which both framework regions and CDR regions are derived from human germline immunoglobulin sequences. Furthermore, if the antibody comprises constant regions, the constant regions are also derived from human germline immunoglobulin sequences. The human antibody disclosed herein may comprises amino acid sequences (e.g., mutations introduced by in vitro random or site-specific mutagenesis or in vivo somatic mutation) that are not encoded by human germline immunoglobulin sequences, for example, in CDRs, particularly in CDR3. However, as used herein, the term "human antibody" does not include antibodies in which CDR sequences derived from the germline of other mammalian species (e.g., mice) are grafted into human framework sequences.

As used herein, the term "recombinant human antibody" includes all human antibodies that are prepared, expressed, produced or isolated by recombinant means, for example, (a) antibodies isolated from transgenic or transchromosomal animals (e.g., mice) using human immunoglobulin genes or from hybridomas prepared from the human immunoglobulin genes; (b) antibodies isolated from host cells (e.g., transfectomas) that transform to express human antibodies; (c) antibodies isolated from recombinant and combinatorial human antibody libraries (e.g., yeast display libraries); and (d) antibodies prepared, expressed, produced or isolated in any other ways including splicing of human immunoglobulin genes to other DNA sequences. These recombinant human antibodies have variable regions in which both framework regions and CDR regions are derived from human germline immunoglobulin sequences. However, in certain embodiments, the recombinant human antibodies can be subjected to in vitro mutagenesis (or in vivo somatic mutagenesis in the case of transgenic animals using human Ig sequences), and the amino acid sequences of the VH and VL regions of the resulting recombinant antibodies, although derived from and related to human germline VH and VL sequences, do not naturally occur in a human antibody germline library.

The term "chimeric antibody" refers to an antibody in which the variable region sequences are derived from one species and the constant region sequences are derived from another species, e.g., an antibody in which the variable region sequences are derived from a mouse antibody and the constant region sequences are derived from a human antibody.

The term "humanized antibody" refers to an antibody in which CDR sequences derived from another mammalian species, such as mice, are linked to human framework sequences. Additional framework region modifications may be introduced in the human framework sequences.

An "isolated" antibody is an antibody which has been separated from components of its natural environment. In some embodiments, the antibody is purified to a purity greater than 95% or 99% as determined by, for example, electrophoresis (e.g., SDS-PAGE, isoelectric focusing (IEF), capillary electrophoresis), or chromatography (e.g., ion exchange or reverse-phase HPLC). For a review of methods for assessing antibody purity, see, e.g., Flatman, S. et al., *J. Chrom. B* 848 (2007) 79-87.

The term "epitope" is an antigen region to which an antibody binds. Epitopes can be formed by contiguous amino acids or noncontiguous amino acids juxtaposed by tertiary folding of a protein.

Herein, TIGIT refers to a "T-cell immune receptor comprising Ig and ITIM domains". The term also includes variants, isotypes, homologs and species homologs of TIGIT. The term "human TIGIT" refers to a human sequence TIGIT. One specific human TIGIT sequence is set forth in SEQ ID NO: 208. In some embodiments, the human TIGIT sequence has at least 95%, even at least 96%, 97%, 98%, or 99% amino acid sequence identity to the human TIGIT amino acid sequence set forth in SEQ ID NO: 208. TIGIT proteins may also include fragments of TIGIT, such as fragments comprising extracellular domains, e.g., fragments that retain the ability of binding to any of the antibodies disclosed herein. Herein, CD155, also known as PVR (poliovirus receptor), PVS, HVED, CD155, NECL5, TAGE4, and Necl-5, interacts with TIGIT to induce immunosuppressive signals. The term "specifically binds to" means that an antibody selectively or preferentially binds to an antigen. If an antibody binds to human TIGIT with a $K_D$ of about $5 \times 10^{-7}$ M or less, about $1 \times 10^{-7}$ M or less, about $5 \times 10^{-8}$ M or less, about $1 \times 10^{-8}$ M or less, about $5 \times 10^{-9}$ M or less measured by biological optical interferometry, the antibody is an antibody that "specifically binds to human TIGIT". However, the antibody that specifically binds to human TIGIT may have cross-reactivity with TIGIT proteins from other species. For example, an antibody specific to human TIGIT, in some embodiments, can cross-react with TIGIT proteins from non-human species. In other embodiments, an antibody specific to human TIGIT may be completely specific to human TIGIT without exhibiting cross-reactivity to other species, or exhibiting cross-reactivity only to TIGIT from certain species.

As used herein, the term "cross-reaction" refers to the ability of an antibody to bind to TIGIT from different species. For example, the antibody binding to human TIGIT described herein may also bind to TIGIT from other species (e.g., monkey and/or mouse TIGIT). A method for determining cross-reactivity includes the method described in examples, as well as standard assays known in the art, such as biological optical interferometry, or flow cytometry.

"Affinity" or "binding affinity" refers to inherent binding affinity that reflects interactions between members of a binding pair. The affinity of a molecule X for its partner Y can be generally represented by an equilibrium dissociation constant ($K_D$), which is the ratio of a dissociation rate constant ($k_{dis}$) to an association rate constant ($k_{on}$). Affinity can be measured by common methods known in the art. One specific method for measuring affinity is the ForteBio kinetic binding assay described herein.

For an IgG antibody, the term "high affinity" means that the antibody binds to a target antigen with a $K_D$ of $1 \times 10^{-7}$ M or less, preferably $5 \times 10^{-8}$ M or less, more preferably about $1 \times 10^{-8}$ M or less, most preferably about $5 \times 10^{-9}$ M or less. However, "high affinity" binding may vary with antibody isotypes. For example, for IgM isotypes, "high affinity" means that an antibody has a $K_D$ of $1 \times 10^{-6}$ M or less, preferably $1 \times 10^{-7}$ M or less, more preferably about $1 \times 10^{-8}$ M or less.

An "antibody that competes for binding" to antigen (e.g., TIGIT) with a reference antibody is an antibody that blocks the binding of the reference antibody to the antigen (e.g., TIGIT) by 50% or more in a competitive assay, and conversely, the reference antibody blocks the binding of the antibody to the antigen (e.g., TIGIT) by 50% or more in the competitive assay. Exemplary competitive assays are described in: "Antibodies", Harbor and Lane (Cold Spring Harbor Press, Cold Spring Harbor, N.Y.). The antibody that competes for binding and the reference antibody can bind to the same epitope region, e.g., the same epitope, adjacent epitopes or overlapping epitopes.

An antibody that inhibits (e.g., competitively inhibits) the binding of a reference antibody to its antigen refers to an antibody that inhibits 50%, 60%, 70%, 80%, 90%, or 95% or more of the binding of the reference antibody to its antigen. Conversely, the reference antibody inhibits 50%, 60%, 70%, 80%, 90%, or 95% or more of the binding of the antibody to its antigen. The binding of an antibody to its antigen can be measured by affinity (e.g., equilibrium dissociation constant). Methods for determining affinity are known in the art.

An antibody that shows the same or similar binding affinity and/or specificity as a reference antibody refers to an antibody that is capable of having at least 50%, 60%, 70%, 80%, 90%, or 95% or more of the binding affinity and/or specificity of the reference antibody. This can be determined by any method known in the art for determining binding affinity and/or specificity.

The term "Fc region" is used herein to define the C-terminus region of an immunoglobulin heavy chain comprising at least a portion of the constant region. The term includes an Fc-region of native sequence and a variant Fc-region. In one embodiment, a human IgG heavy chain Fc-region extends from Cys226 or from Pro230 of a heavy chain to a carboxyl terminus. However, the C-terminus lysine (Lys447) of the Fc region may or may not be present. Unless otherwise indicated herein, the numbering of amino acid residues in the Fc-region or constant region is based on the EU numbering system, also known as the EU index, as described in Kabat, E. A., et. al., *Sequences of Proteins of Immunological Interest*, 5th edition, Public Health Service, National Institutes of Health, Bethesda, Md. (1991), NIH Publication 91-3242.

The term "variant" related to an antibody herein refers to an antibody that comprises a target antibody region having amino acid alterations by virtue of at least one, for example, 1-30, 1-20 or 1-10, e.g., 1, 2, 3, 4 or 5 amino acid substitutions, deletions and/or insertions, when compared to the reference antibody, wherein the variant substantially retains at least one biological property (e.g., antigen binding capacity) of the antibody molecule prior to alteration. The target antibody region may be the full length of the antibody, or the heavy chain variable region or the light chain variable region or a combination thereof, or one or more heavy chain CDR regions or one or more light chain CDR regions or a combination thereof. Herein, an antibody region having amino acid alterations relative to a reference antibody region is also referred to as a "variant" of the reference antibody region.

Herein, the term "sequence identity" refers to the degree to which sequences are identical on a nucleotide-by-nucleotide or amino acid-by-amino acid basis in a comparison window. The "percent sequence identity" can be calculated by the following steps: comparing two optimally aligned sequences in a comparison window; determining the number of positions in which nucleic acid bases (e.g., A, T, C, G and I) or amino acid residues (e.g., Ala, Pro, Ser, Thr, Gly, Val, Leu, Ile, Phe, Tyr, Trp, Lys, Arg, His, Asp, Glu, Asn, Gln, Cys, and Met) are the same in the two sequences to yield the number of matched positions; dividing the number of matched positions by the total number of positions in the comparison window (i.e., the window size); and multiplying the result by 100 to yield a percent sequence identity. Optimal alignment for determining the percent sequence identity may be achieved in a variety of ways known in the art, for example, using publicly available computer software such as BLAST, BLAST-2, ALIGN, or Megalign (DNASTAR) software. Those skilled in the art can determine suitable parameters for alignment of the sequences, including any algorithm necessary to yield optimal alignment within a full-length sequence range or target sequence region being compared.

Herein, with respect to antibody sequences, the percent amino acid sequence identity is determined by optimally aligning a candidate antibody sequence with a reference antibody sequence, and in a preferred embodiment, optimal alignment is performed according to the Kabat numbering scheme. Herein, without specifying the comparison window (i.e. the target antibody region to be compared), it will be applicable to align over the full length of the reference antibody sequence. In some embodiments, with respect to antibodies, the sequence identity may be achieved throughout the heavy chain variable region and/or the light chain variable region, or the percent sequence identity may be limited to the framework regions only, while the sequences of corresponding CDR regions remain 100% identical.

Similarly, with respect to antibody sequences, a candidate antibody having amino acid alterations in the target antibody region relative to a reference antibody can be determined based on the alignment.

Herein, "conservative substitution" refers to an amino acid alteration that results in the replacement of an amino acid with a chemically similar amino acid Amino acid modifications such as substitutions can be introduced into the antibody of the invention by standard methods known in the art, such as site-directed mutagenesis and PCR-mediated mutagenesis.

Conservative replacement tables that provide functionally similar amino acids are well known in the art. In a preferred aspect, conservatively substituted residues are from the Table A of conservative substitutions below, preferably are the preferred conservatively substituted residues shown in Table A.

TABLE A

| Primitive residue | Exemplary substitution | Preferred conservative substitution |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Nle | Leu |
| Leu (L) | Nle; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Nle | Leu |

All aspects of the present invention are further detailed in the following sections.

I. Anti-TIGIT Antibody of the Present Invention

In one aspect, the present invention provides an antibody or an antigen-binding fragment thereof, particularly a fully humanized antibody or an antigen-binding fragment thereof, that specifically binds to TIGIT, preferably a human TIGIT protein (e.g., the human TIGIT sequence of SEQ ID NO: 208). In some embodiments, the antigen-binding fragment of the antibody disclosed herein is an antibody fragment selected from: a Fab, a Fab', a Fab'-SH, an Fv, a single-chain antibody such as an scFv, an (Fab')$_2$ fragment, a single-domain antibody, a diabody (dAbs), and a linear antibody.

Advantageous Biological Properties of Antibodies

In some embodiments, the anti-TIGIT antibody or the antigen-binding fragment thereof disclosed herein binds to human TIGIT with high affinity, e.g., with a dissociation equilibrium constant ($K_D$) of less than $100 \times 10^{-9}$ M, less than or equal to about $50 \times 10^{-9}$ M, preferably less than or equal to about $1\text{-}30 \times 10^{-9}$ M, more preferably about $1 \times 10^{-9}$ M, further preferably about $1\text{-}10 \times 10^{-10}$ M. Preferably, $K_D$ is determined by using biological optical interferometry (e.g., Fortebio affinity assay). In some embodiments, the $K_D$ is determined by measuring the monovalent affinity of a Fab (e.g., a Fab expressed by yeasts) of the antibody to human TIGIT. Preferably, the monovalent $K_D$ is $1\text{-}100 \times 10^{-10}$ M, more preferably $1\text{-}50 \times 10^{-10}$ M, further preferably $1\text{-}10 \times 10^{-10}$ M or $2\text{-}5 \times 10^{-10}$ M. In other embodiments, the $K_D$ is determined by measuring the monovalent affinity of an intact antibody (e.g., an intact antibody expressed by CHO cells) to human TIGIT. Preferably, the monovalent $K_D$ is $1\text{-}50 \times 10^{-10}$ M, more preferably $1\text{-}30 \times 10^{-10}$ M or $1\text{-}10 \times 10^{-10}$ M.

In some embodiments, the anti-TIGIT antibody or the antigen-binding fragment thereof disclosed herein have a cross-reaction with monkey TIGIT. In some embodiments, the antibody binds to monkey TIGIT with high affinity, wherein the $K_D$ (e.g., determined by measuring the monovalent affinity of an intact antibody to monkey TIGIT) is about $0.1\text{-}100 \times 10^{-9}$ M, more preferably $0.1\text{-}50 \times 10^{-9}$ M or $1\text{-}30 \times 10^{-10}$ M. In some embodiments, the antibody has a cross-reaction with mouse TIGIT, wherein the $K_D$ (e.g., determined by measuring the monovalent affinity of an intact antibody to mouse TIGIT) is about $1\text{-}100 \times 10^{-9}$ M, e.g., $1\text{-}10 \times 10^{-7}$ M or $1\text{-}10 \times 10^{-8}$ M, or $1\text{-}10 \times 10^{-9}$ M. In other embodiments, the anti-TIGIT antibody of the present invention does not have a cross-reaction with mouse TIGIT.

In some embodiments, the antibody or the antigen-binding fragment thereof disclosed herein binds to TIGIT expressed on the surface of cells with high affinity. In one embodiment, a cell expressing human TIGIT on the surface is a CHO cell. Preferably, the $EC_{50}$ of the antibody binding to a cell expressing human TIGIT is measured by flow cytometry (e.g., FACS). In some embodiments, the antibody is an intact antibody expressed by yeasts with an $EC_{50}$ of less than about 10 nM, e.g., 0.1-1 nM, preferably less than or equal to about 1 nM, more preferably about 0.2-0.9 nM, such as 0.9 nM, 0.6 M, or 0.4 nM. In other embodiments, the antibody is an intact antibody expressed by CHO cells with an $EC_{50}$ of less than about 10 nM, e.g., 0.1-1 nM, preferably about 0.1-0.3 nM, such as about 0.3 nM, 0.2 M or 0.1 nM.

In some embodiments, the antibody or the antigen-binding fragment thereof disclosed herein inhibits relevant activities of TIGIT. In some embodiments, the antibody or the antigen-binding fragment thereof disclosed herein blocks the binding of TIGIT to its ligand CD155. Preferably, the ability of the antibody to block the binding of human TIGIT (TIGIT expressed on cells) to human CD155 (e.g., $IC_{50}$) is measured by flow cytometry (e.g., FACS). In some embodiments, the antibody is an intact antibody expressed by yeasts with an $IC_{50}$ of less than about 10 nM, e.g., 0.1-2 nM, preferably about 0.1-1.0 nM, such as 0.8 nM, 0.6 M, 0.4 nM, or 0.2 nM. In other embodiments, the antibody is an intact antibody expressed by CHO cells with an $EC_{50}$ of less than about 1 nM, e.g., 0.1-0.5 nM, preferably about 0.3 nM, 0.2 M or 0.1 nM.

In some embodiments, the antibody or the antigen-binding fragment thereof disclosed herein reduces or eliminates the inhibitory signaling caused by the binding of TIGIT to CD155. In some embodiments, the antibody or fragment disclosed herein reduces or eliminates TIGIT-mediated inhibitory signaling in a cell (particularly a T cell) expressing TIGIT. In some embodiments, the antibody or the antigen-binding fragment thereof disclosed herein induces the expression of genes downstream of IL-2 promoters in T cells, and in some embodiments, increases the production of IL-2 in T cells. In some embodiments, the ability of the antibody to reduce or eliminate the inhibitory signaling caused by the binding of TIGIT to CD155 (e.g., $EC_{50}$) is detected using fluorescent reporter assay (e.g., the MOA assay of example 5). In some embodiments, the antibody is an intact antibody expressed by yeasts, with an $EC_{50}$ of preferably less than about 10 nM, e.g., 0.1-5 nM, more preferably about 0.1-3.0 nM, such as about 2.0 nM, 1.5 nM, 1.0 nM, or 0.5 nM. In other embodiments, the antibody is an intact antibody expressed by CHO cells, with an $EC_{50}$ of preferably less than 5 nM, e.g., about 0.1-3.0 nM, such as about 1.6 nM, 1.2 nM, 1.0 nM, or about 0.18-0.5 nM.

In some embodiments, the antibody or the antigen-binding fragment thereof disclosed herein inhibits the growth of a tumor that comprises infiltrating lymphocytes expressing human TIGIT. In one embodiment, the tumor is a gastrointestinal tumor, preferably colorectal cancer. For example, in an in vivo transplanted tumor model, such as in a MC38 mouse, the growth of colon cancer cells is inhibited. In some embodiments, the combination therapy of the antibody of the present invention with an anti-PD-1 antibody achieves a much better anti-tumor effect than either antibody used alone.

Preferably, the antibody or the antigen-binding fragment thereof disclosed herein exhibits at least one, preferably at least two, more preferably at least three, four, or five, even more preferably all of the above properties.

CDR Regions of Antibodies

"Complementarity determining region", "CDR region" or "CDR" (used interchangeably herein with a hypervariable region "HVR") is an amino acid region in the variable region of an antibody that is primarily responsible for binding to an epitope of an antigen. The CDRs of the heavy and light chains are generally referred to as CDR1, CDR2, and CDR3, which are numbered sequentially from N-terminus. The CDRs located in the heavy chain variable domain of the antibody are referred to as HCDR1, HCDR2 and HCDR3, whereas the CDRs located in the light chain variable domain of the antibody are referred to as LCDR1, LCDR2 and LCDR3.

Combinations of the VH and VL sequences of some exemplary antibodies disclosed herein are listed in Table B below:

| Antibody | VH, which comprises or consists of an amino acid sequence set forth in the following SEQ ID NOs | VL, which comprises or consists of an amino acid sequence set forth in the following SEQ ID NOs |
|---|---|---|
| 1 | SEQ ID NO:84 | SEQ ID NO:104 |
| 2 | SEQ ID NO:85 | SEQ ID NO:104 |
| 3 | SEQ ID NO:86 | SEQ ID NO:104 |
| 4 | SEQ ID NO:87 | SEQ ID NO:104 |
| 5 | SEQ ID NO:88 | SEQ ID NO:105 |
| 6 | SEQ ID NO:89 | SEQ ID NO:105 |
| 7 | SEQ ID NO:90 | SEQ ID NO:106 |
| 8 | SEQ ID NO:91 | SEQ ID NO:107 |
| 9 | SEQ ID NO:92 | SEQ ID NO:107 |
| 10 | SEQ ID NO:93 | SEQ ID NO:107 |
| 11 | SEQ ID NO:94 | SEQ ID NO:108 |
| 12 | SEQ ID NO:95 | SEQ ID NO:108 |
| 13 | SEQ ID NO:96 | SEQ ID NO:108 |
| 14 | SEQ ID NO:97 | SEQ ID NO:108 |
| 15 | SEQ ID NO:98 | SEQ ID NO:109 |
| 16 | SEQ ID NO:99 | SEQ ID NO:109 |
| 17 | SEQ ID NO:100 | SEQ ID NO:109 |
| 18 | SEQ ID NO:101 | SEQ ID NO:110 |
| 19 | SEQ ID NO:102 | SEQ ID NO:110 |
| 20 | SEQ ID NO:103 | SEQ ID NO:110 |

Various schemes for determining the CDR sequence of a given VH or VL amino acid sequence are known in the art. For example, Kabat complementarity determining regions (CDRs) are determined based on sequence variability and are the most commonly used (Kabat et al., *Sequences of Proteins of Immunological Interest*, 5th Ed. Public Health Service, National Institutes of Health, Bethesda, Md. (1991)). Chothia scheme is based on the positions of structural loops (Chothia and Lesk, *J. mol. biol.* 196:901-917 (1987)). AbM HVRs are a compromise between Kabat HVRs and Chothia structural loops and are used by Oxford Molecular's AbM antibody modeling software. The "Contact" HVRs are based on analysis of available complex crystal structures. According to different CDR determination schemes, the residue of each HVR/CDR among these HVRs is described as follows.

| CDR | Kabat scheme | AbM scheme | Chothia scheme | Contact scheme |
|---|---|---|---|---|
| LCDR1 | L24-L34 | L24-L34 | L26-L32 | L30-L36 |
| LCDR2 | L50-L56 | L50-L56 | L50-L52 | L46-L55 |
| LCDR3 | L89-L97 | L89-L97 | L91-L96 | L89-L96 |

| CDR | Kabat scheme | AbM scheme | Chothia scheme | Contact scheme |
|---|---|---|---|---|
| HCDR1 | H31-H35B | H26-H35B | H26-H32 | H30-H35B |
| | (Kabat numbering system) | | | |
| HCDR1 | H31-H35 | H26-H35 | H26-H32 | H30-H35 |
| | (Chothia numbering system) | | | |
| HCDR2 | H50-H65 | H50-H58 | H53-H55 | H47-H58 |
| HCDR3 | H95-H102 | H95-H102 | H96-H101 | H93-H101 |
| | (Kabat numbering system) | | | |

HVRs may also be HVR sequences located at following Kabat residue positions according to the Kabat numbering system: positions 24-36 or 24-34 (LCDR1), positions 46-56 or 50-56 (LCDR2), and positions 89-97 or 89-96 (LCDR3) in the VL; and positions 26-35 or 27-35B (HCDR1), positions 50-65 or 49-65 (HCDR2), and positions 93-102, 94-102, or 95-102 (HCDR3) in the VH.

In one embodiment, the HVRs of the antibody disclosed herein are HVR sequences located at the following Kabat residue positions according to the Kabat numbering system: positions 24-34 (LCDR1), 50-56 (LCDR2), and 89-97 (LCDR3) in the VL, and positions 27-35B (HCDR1), 50-65 (HCDR2), and 93-102 (HCDR3) in the VH.

In one embodiment, the HVRs of the antibody disclosed herein are HVR sequences located at the following Kabat residue positions according to the Kabat numbering system: positions 24-34 (LCDR1), 50-56 (LCDR2), and 89-97 (LCDR3) in the VL, and positions 26-35B (HCDR1), 50-65 (HCDR2), and 95-102 (HCDR3) in the VH.

HVRs may also be determined based on the same Kabat numbering positions of a reference CDR sequence (e.g., any one of the exemplary CDRs disclosed herein).

Unless otherwise stated, the term "CDR", "CDR sequence", "HVR", or "HVR sequence" used herein includes HVR or CDR sequences determined in any of the ways described above.

Unless otherwise stated, residue positions of an antibody variable region (including heavy chain variable region residues and light chain variable region residues) are numbered according to the Kabat numbering system (Kabat et al., *Sequences of Proteins of Immunological Interest*, 5th Ed. Public Health Service, National Institutes of Health, Bethesda, Md. (1991)) in the present invention. In one preferred embodiment, the CDR sequences disclosed herein are shown in Table 2, wherein the HCDR1 is a CDR sequence determined by the AbM scheme, and remaining CDRs are CDR sequences determined by the Kabat scheme.

In another preferred embodiment, the CDR sequences disclosed herein are shown in Table 1.

Combinations of some exemplary CDR sequences disclosed herein are listed in Table C below:

| Combinations | HCDR1, which comprises or consists of an amino acid sequence set forth in the following SEQ ID NOs | HCDR2, which comprises or consists of an amino acid sequence set forth in the following SEQ ID Nos | HCDR3, which comprises or consists of an amino acid sequence set forth in the following SEQ ID Nos | LCDR1, which comprises or consists of an amino acid sequence set forth in the following SEQ ID Nos | LCDR2, which comprises or consists of an amino acid sequence set forth in the following SEQ ID Nos | LCDR3, which comprises or consists of an amino acid sequence set forth in the following SEQ ID Nos |
|---|---|---|---|---|---|---|
| 1 | SEQ ID NO: 1 | SEQ ID NO: 6 | SEQ ID NO: 11 | SEQ ID NO: 16 | SEQ ID NO: 17 | SEQ ID NO: 18 |
| 2 | SEQ ID NO: 2 | SEQ ID NO: 7 | SEQ ID NO: 12 | SEQ ID NO: 16 | SEQ ID NO: 17 | SEQ ID NO: 18 |
| 3 | SEQ ID NO: 3 | SEQ ID NO: 8 | SEQ ID NO: 13 | SEQ ID NO: 16 | SEQ ID NO: 17 | SEQ ID NO: 18 |
| 4 | SEQ ID NO: 4 | SEQ ID NO: 9 | SEQ ID NO: 14 | SEQ ID NO: 16 | SEQ ID NO: 17 | SEQ ID NO: 18 |
| 5 | SEQ ID NO: 5 | SEQ ID NO: 10 | SEQ ID NO: 15 | SEQ ID NO: 16 | SEQ ID NO: 17 | SEQ ID NO: 18 |
| 6 | SEQ ID NO: 19 | SEQ ID NO: 22 | SEQ ID NO: 25 | SEQ ID NO: 26 | SEQ ID NO: 27 | SEQ ID NO: 28 |
| 7 | SEQ ID NO: 20 | SEQ ID NO: 23 | SEQ ID NO: 25 | SEQ ID NO: 26 | SEQ ID NO: 27 | SEQ ID NO: 28 |

-continued

| Combinations | HCDR1, which comprises or consists of an amino acid sequence set forth in the following SEQ ID NOs | HCDR2, which comprises or consists of an amino acid sequence set forth in the following SEQ ID Nos | HCDR3, which comprises or consists of an amino acid sequence set forth in the following SEQ ID Nos | LCDR1, which comprises or consists of an amino acid sequence set forth in the following SEQ ID Nos | LCDR2, which comprises or consists of an amino acid sequence set forth in the following SEQ ID Nos | LCDR3, which comprises or consists of an amino acid sequence set forth in the following SEQ ID Nos |
|---|---|---|---|---|---|---|
| 8 | SEQ ID NO: 19 | SEQ ID NO: 22 | SEQ ID NO: 25 | SEQ ID NO: 26 | SEQ ID NO: 27 | SEQ ID NO: 29 |
| 9 | SEQ ID NO: 21 | SEQ ID NO: 24 | SEQ ID NO: 25 | SEQ ID NO: 26 | SEQ ID NO: 27 | SEQ ID NO: 30 |
| 10 | SEQ ID NO: 31 | SEQ ID NO: 34 | SEQ ID NO: 38 | SEQ ID NO: 41 | SEQ ID NO: 42 | SEQ ID NO: 43 |
| 11 | SEQ ID NO: 31 | SEQ ID NO: 35 | SEQ ID NO: 38 | SEQ ID NO: 41 | SEQ ID NO: 42 | SEQ ID NO: 43 |
| 12 | SEQ ID NO: 32 | SEQ ID NO: 36 | SEQ ID NO: 39 | SEQ ID NO: 41 | SEQ ID NO: 42 | SEQ ID NO: 43 |
| 13 | SEQ ID NO: 33 | SEQ ID NO: 37 | SEQ ID NO: 40 | SEQ ID NO: 41 | SEQ ID NO: 42 | SEQ ID NO: 43 |
| 14 | SEQ ID NO: 44 | SEQ ID NO: 48 | SEQ ID NO: 53 | SEQ ID NO: 57 | SEQ ID NO: 58 | SEQ ID NO: 59 |
| 15 | SEQ ID NO: 45 | SEQ ID NO: 49 | SEQ ID NO: 53 | SEQ ID NO: 57 | SEQ ID NO: 58 | SEQ ID NO: 59 |
| 16 | SEQ ID NO: 46 | SEQ ID NO: 50 | SEQ ID NO: 54 | SEQ ID NO: 57 | SEQ ID NO: 58 | SEQ ID NO: 59 |
| 17 | SEQ ID NO: 46 | SEQ ID NO: 51 | SEQ ID NO: 55 | SEQ ID NO: 57 | SEQ ID NO: 58 | SEQ ID NO: 59 |
| 18 | SEQ ID NO: 47 | SEQ ID NO: 52 | SEQ ID NO: 56 | SEQ ID NO: 57 | SEQ ID NO: 58 | SEQ ID NO: 59 |
| 19 | SEQ ID NO: 60 | SEQ ID NO: 6 | SEQ ID NO: 66 | SEQ ID NO: 69 | SEQ ID NO: 17 | SEQ ID NO: 70 |
| 20 | SEQ ID NO: 61 | SEQ ID NO: 63 | SEQ ID NO: 66 | SEQ ID NO: 69 | SEQ ID NO: 17 | SEQ ID NO: 70 |
| 21 | SEQ ID NO: 61 | SEQ ID NO: 64 | SEQ ID NO: 67 | SEQ ID NO: 69 | SEQ ID NO: 17 | SEQ ID NO: 70 |
| 22 | SEQ ID NO: 62 | SEQ ID NO: 65 | SEQ ID NO: 68 | SEQ ID NO: 69 | SEQ ID NO: 17 | SEQ ID NO: 70 |
| 23 | SEQ ID NO: 71 | SEQ ID NO: 22 | SEQ ID NO: 78 | SEQ ID NO: 81 | SEQ ID NO: 82 | SEQ ID NO: 83 |
| 24 | SEQ ID NO: 72 | SEQ ID NO: 75 | SEQ ID NO: 78 | SEQ ID NO: 81 | SEQ ID NO: 82 | SEQ ID NO: 83 |
| 25 | SEQ ID NO: 73 | SEQ ID NO: 76 | SEQ ID NO: 79 | SEQ ID NO: 81 | SEQ ID NO: 82 | SEQ ID NO: 83 |
| 26 | SEQ ID NO: 74 | SEQ ID NO: 77 | SEQ ID NO: 80 | SEQ ID NO: 81 | SEQ ID NO: 82 | SEQ ID NO: 83 |

Combinations of other exemplary CDR sequences disclosed herein are listed in Table D below:

| Combinations | HCDR1, which comprises or consists of an amino acid sequence set forth in the following SEQ ID NOs | HCDR2, which comprises or consists of an amino acid sequence set forth in the following SEQ ID NOs | HCDR3, which comprises or consists of an amino acid sequence set forth in the following SEQ ID NOs | LCDR1, which comprises or consists of an amino acid sequence set forth in the following SEQ ID NOs | LCDR2, which comprises or consists of an amino acid sequence set forth in the following SEQ ID NOs | LCDR3, which comprises or consists of an amino acid sequence set forth in the following SEQ ID NOs |
|---|---|---|---|---|---|---|
| 1 | SEQ ID NO: 178 | SEQ ID NO: 6 | SEQ ID NO: 182 | SEQ ID NO: 16 | SEQ ID NO: 17 | SEQ ID NO: 18 |
| 2 | SEQ ID NO: 179 | SEQ ID NO: 7 | SEQ ID NO: 183 | SEQ ID NO: 16 | SEQ ID NO: 17 | SEQ ID NO: 18 |
| 3 | SEQ ID NO: 180 | SEQ ID NO: 8 | SEQ ID NO: 184 | SEQ ID NO: 16 | SEQ ID NO: 17 | SEQ ID NO: 18 |
| 4 | SEQ ID NO: 181 | SEQ ID NO: 9 | SEQ ID NO: 185 | SEQ ID NO: 16 | SEQ ID NO: 17 | SEQ ID NO: 18 |
| 5 | SEQ ID NO: 186 | SEQ ID NO: 22 | SEQ ID NO: 188 | SEQ ID NO: 26 | SEQ ID NO: 27 | SEQ ID NO: 28 |
| 6 | SEQ ID NO: 187 | SEQ ID NO: 23 | SEQ ID NO: 188 | SEQ ID NO: 26 | SEQ ID NO: 27 | SEQ ID NO: 28 |
| 7 | SEQ ID NO: 186 | SEQ ID NO: 22 | SEQ ID NO: 188 | SEQ ID NO: 26 | SEQ ID NO: 27 | SEQ ID NO: 29 |
| 8 | SEQ ID NO: 189 | SEQ ID NO: 34 | SEQ ID NO: 191 | SEQ ID NO: 41 | SEQ ID NO: 42 | SEQ ID NO: 43 |
| 9 | SEQ ID NO: 189 | SEQ ID NO: 35 | SEQ ID NO: 191 | SEQ ID NO: 41 | SEQ ID NO: 42 | SEQ ID NO: 43 |
| 10 | SEQ ID NO: 190 | SEQ ID NO: 36 | SEQ ID NO: 192 | SEQ ID NO: 41 | SEQ ID NO: 42 | SEQ ID NO: 43 |
| 11 | SEQ ID NO: 193 | SEQ ID NO: 48 | SEQ ID NO: 196 | SEQ ID NO: 57 | SEQ ID NO: 58 | SEQ ID NO: 59 |
| 12 | SEQ ID NO: 194 | SEQ ID NO: 49 | SEQ ID NO: 196 | SEQ ID NO: 57 | SEQ ID NO: 58 | SEQ ID NO: 59 |
| 13 | SEQ ID NO: 195 | SEQ ID NO: 50 | SEQ ID NO: 197 | SEQ ID NO: 57 | SEQ ID NO: 58 | SEQ ID NO: 59 |
| 14 | SEQ ID NO: 195 | SEQ ID NO: 51 | SEQ ID NO: 198 | SEQ ID NO: 57 | SEQ ID NO: 58 | SEQ ID NO: 59 |
| 15 | SEQ ID NO: 199 | SEQ ID NO: 6 | SEQ ID NO: 201 | SEQ ID NO: 69 | SEQ ID NO: 17 | SEQ ID NO: 70 |
| 16 | SEQ ID NO: 200 | SEQ ID NO: 63 | SEQ ID NO: 201 | SEQ ID NO: 69 | SEQ ID NO: 17 | SEQ ID NO: 70 |
| 17 | SEQ ID NO: 200 | SEQ ID NO: 64 | SEQ ID NO: 202 | SEQ ID NO: 69 | SEQ ID NO: 17 | SEQ ID NO: 70 |
| 18 | SEQ ID NO: 203 | SEQ ID NO: 22 | SEQ ID NO: 206 | SEQ ID NO: 81 | SEQ ID NO: 82 | SEQ ID NO: 83 |
| 19 | SEQ ID NO: 204 | SEQ ID NO: 75 | SEQ ID NO: 206 | SEQ ID NO: 81 | SEQ ID NO: 82 | SEQ ID NO: 83 |
| 20 | SEQ ID NO: 205 | SEQ ID NO: 76 | SEQ ID NO: 207 | SEQ ID NO: 81 | SEQ ID NO: 82 | SEQ ID NO: 83 |

Antibodies with different specificities (i.e., different binding sites for different antigens) have different CDRs. However, although CDRs differ from antibody to antibody, only a limited number of amino acid positions within the CDRs are directly involved in antigen binding. The smallest overlapping region can be determined using at least two of the Kabat, Chothia, AbM, and Contact schemes, thereby providing a "minimal binding unit" for antigen binding. The minimal binding unit may be a sub-portion of the CDR. As will be clear to those skilled in the art, residues of the rest CDR sequences can be determined via antibody structure and protein folding. Therefore, any variants of the CDRs given herein are also considered in the present invention. For example, in a CDR variant, the amino acid residues in the minimal binding unit may remain unchanged, while the other CDR residues defined by Kabat or Chothia may be substituted by conservative amino acid residues.

In some embodiments, the antibody of the present invention has at least one, two, three, four, five, or six CDRs that are identical to, or are variants of, corresponding CDRs in the variable region sequences of any of the antibodies listed in Table B. In some embodiments, the antibody of the present invention has at least one, two, or three HCDRs that are identical to, or are variants of, corresponding heavy chain CDRs in the variable region sequences of any of the antibodies listed in Table B. In some embodiments, the antibody of the present invention has at least one, two, or three LCDRs that are identical to, or are variants of, corresponding light chain CDRs in the variable region sequences of any of the antibodies listed in Table B. Herein, "corresponding CDRs" refer to CDRs that are located at positions in the amino acid sequences of a variable region of a candidate antibody that are most similar to where CDRs of a reference antibody locate at after optimal alignment. Herein, a CDR variant is a CDR that has been modified by at least one, for example, one or two or three amino acid substitutions, deletions, and/or insertions, wherein an antigen-binding molecule comprising the CDR variant substantially retains the biological properties of the antigen-binding molecule comprising the unmodified CDRs, e.g., retains at least 60%, 70%, 80%, 90%, or 100% of the biological activity (e.g., antigen-binding ability). It is understood that each CDR may be modified independently or in combination. Preferably, an amino acid modification is an amino acid substitution, in particular a conservative amino acid substitution, such as a preferred conservative amino acid replacement listed in Table A. In some embodiments, amino acid substitutions preferably occur at amino acid positions corresponding to X residues of the consensus CDR sequences (e.g., SEQ ID NOs: 5, 10, 15, 21, 24, 30, 33, 37, 40, 47, 52, 56, 62, 65, 68, 74, 77, and 80) provided herein.

In addition, it is known in the art that the CDR3 region, which is independent of the CDR1 and/or CDR2 regions, alone can determine the binding specificity of an antibody to an associated antigen. Furthermore, a variety of other antibodies having the same binding specificity can be generated based on the consensus CDR3 sequence. See, e.g., U.S. Pat. Nos. 6,951,646; 6,914,128; 6,090,382; 6,818,216; 6,156, 313; 6,827,925; 5,833,943; 5,762,905; and 5,760,185. All of these references are incorporated herein by reference.

Thus, in one embodiment, the antibody of the present invention comprises a CDR3 sequence from the heavy and/or light chain variable region sequence of any one of the antibodies shown in Table B, wherein the antibody is capable of specifically binding to human TIGIT. In yet another embodiment, the antibody may further comprise a CDR2 from the heavy and/or light chain variable region of the same antibody, or a CDR2 from the heavy and/or light chain variable region of different TIGIT antibodies. In yet another embodiment, the antibody may further comprise a CDR1 from the heavy and/or light chain variable region of the same antibody, or a CDR1 from the heavy and/or light chain variable region of different TIGIT antibodies. Activities of these antibodies, including an activity of binding to human TIGIT, an activity of blocking the binding of TIGIT to CD155 molecules, and/or an activity of inhibiting tumor growth, can be characterized by assays described herein.

In yet another aspect, given that the antigen-binding specificity is dependent primarily on the CDR1, CDR2, and CDR3 regions, in some embodiments, VH CDRs 1, 2, and 3 sequences and VL CDRs 1, 2, and 3 sequences can be "combined and paired" (i.e., CDRs from different antibodies that bind to the same TIGIT antigen can be combined and paired, and each antibody preferably comprises VH CDRs 1, 2, and 3 and VL CDRs 1, 2, and 3) to produce other molecules of the present invention that bind to TIGIT. The binding of such "combined and paired" antibodies to TIGIT can be tested by binding assays known in the art (e.g., ELISA, SET, and Biacore) and other assays described in the examples. When VH CDR sequences are combined and paired, CDR1, CDR2, and/or CDR3 sequences from a particular VH sequence are preferably substituted with structurally similar CDR sequences. Likewise, when VL CDR sequences are combined and paired, CDR1, CDR2, and/or CDR3 sequences from a particular VL sequence are preferably substituted with structurally similar CDR sequences. CDRs can be "combined and paired" among the antibodies shown in Table 3 of the present invention. In addition, it will be appreciated by those skilled in the art that other antibodies of the present invention may also be generated by substituting the structurally similar CDR sequences of the antibodies disclosed herein with one or more of VH CDR and/or VL CDR sequences from other different antibodies.

Thus, in some embodiments, the antibody or the antigen-binding fragment thereof disclosed herein comprises a heavy chain variable region comprising a heavy chain complementarity determining region 3 (HCDR3), the HCDR3:
(i) is identical to an HCDR3 of the heavy chain variable region of any one of the antibodies listed in Table B;
(ii) is identical to any of the HCDR3 sequences listed in Table C or D; or
(iii) comprises at least 1 (preferably 1-2, and more preferably 1) amino acid alteration (preferably substitution, and more preferably conservative substitution) relative to the HCDR3 of (i) or (ii).

In some embodiments, the antibody or the antigen-binding fragment thereof disclosed herein comprises a heavy chain variable region and a light chain variable region, and the heavy chain complementarity determining regions 3 (HCDR3) and light chain complementarity determining regions 3 (LCDR3) of the antibody:
(i) are identical to an HCDR3 and an LCDR3 of the heavy and light chain variable region sequences of any one of the antibodies listed in Table B;
(ii) are identical to the HCDR3 and LCDR3 sequences in any combination listed in Table C or D; or
(iii) comprise at least 1 (preferably 1-2, and more preferably 1) amino acid alteration (preferably substitution, and more preferably conservative substitution) in total relative to the HCDR3 and LCDR3 of (i) or (ii).

In one embodiment, the antibody or the antigen-binding fragment thereof disclosed herein comprises a heavy chain variable region (VH), wherein the VH comprises:
(i) HCDR1, HCDR2 and HCDR3 sequences contained in a VH sequence of any one of the antibodies listed in Table B;
(ii) HCDR1, HCDR2 and HCDR3 sequences in any combination listed in Table C or D; or
(iii) sequences having at least one and no more than 5, 4, 3, 2, or 1 amino acid alteration (preferably amino acid substitution, preferably conservative substitution) in the three CDRs in total relative to the sequences of (i) or (ii).

In another embodiment, the antibody or the antigen-binding fragment thereof disclosed herein comprises a light chain variable region (VL), wherein the VL comprises:
(i) LCDR1, LCDR2, and LCDR3 sequences contained in a VL sequence of any one of the antibodies listed in Table B;
(ii) LCDR1, LCDR2 and LCDR3 sequences in any combination listed in Table C or D; or
(iii) sequences having at least one and no more than 5, 4, 3, 2, or 1 amino acid alteration (preferably amino acid substitution, preferably conservative substitution) in the three CDRs in total relative to the sequences of (i) or (ii).

In another embodiment, the antibody or the antigen-binding fragment thereof disclosed herein comprises a heavy chain variable region and a light chain variable region, wherein the antibody comprises:
(i) six CDR sequences contained in VH and VL sequences of any one of the antibodies listed in Table B;
(ii) six CDR sequences in any combination listed in Table C or D; or
(iii) sequences having at least one and no more than 10, 5, 4, 3, 2, or 1 amino acid alteration (preferably amino acid substitution, preferably conservative substitution) in the six CDRs in total relative to the sequences of (i) or (ii).

In one embodiment, the antibody or antigen-binding fragment thereof disclosed herein comprises:
(i) HCDR1, HCDR2 and HCDR3 sequences of a heavy chain variable region set forth in SEQ ID NOs: 84, 85, 86, or 87, and LCDR1, LCDR2 and LCDR3 sequences of a light chain variable region set forth in SEQ ID NO: 104,
(ii) HCDR1, HCDR2 and HCDR3 sequences of a heavy chain variable region set forth in SEQ ID NOs: 88, 89, or 90, and LCDR1, LCDR2 and LCDR3 sequences of a light chain variable region set forth in SEQ ID NO: 105 or 106,
(iii) HCDR1, HCDR2 and HCDR3 sequences of a heavy chain variable region set forth in SEQ ID NOs: 91, 92, or 93, and LCDR1, LCDR2 and LCDR3 sequences of a light chain variable region set forth in SEQ ID NO: 107,
(iv) HCDR1, HCDR2 and HCDR3 sequences of a heavy chain variable region set forth in SEQ ID NOs: 94, 95, 96, or 97, and LCDR1, LCDR2 and LCDR3 sequences of a light chain variable region set forth in SEQ ID NO: 108,
(v) HCDR1, HCDR2 and HCDR3 sequences of a heavy chain variable region set forth in SEQ ID NOs: 98, 99, or 100, and LCDR1, LCDR2 and LCDR3 sequences of a light chain variable region set forth in SEQ ID NO: 109, or
(vi) HCDR1, HCDR2 and HCDR3 sequences of a heavy chain variable region set forth in SEQ ID NOs: 101, 102, or 103, and LCDR1, LCDR2 and LCDR3 sequences of a light chain variable region set forth in SEQ ID NO: 110.

In a preferred embodiment, the antibody or the antigen-binding fragment thereof disclosed herein comprises three complementarity determining regions of a heavy chain variable region (HCDRs), and three complementarity determining regions of a light chain variable region (LCDRs), wherein
(i) HCDR1 comprises or consists of an amino acid sequence selected from SEQ ID NOs: 1-5 or 178-181, HCDR2 comprises or consists of an amino acid sequence selected from SEQ ID NOs: 6-10, HCDR3 comprises or consists of an amino acid sequence selected from SEQ ID NOs: 11-15 or 182-185, LCDR1 comprises or consists of an amino acid sequence of SEQ ID NO: 16, LCDR2 comprises or consists of an amino acid sequence of SEQ ID NO: 17, and LCDR3 comprises or consists of an amino acid sequence of SEQ ID NO: 18;
(ii) HCDR1 comprises or consists of an amino acid sequence selected from SEQ ID NOs: 19-21 or 186-187, HCDR2 comprises or consists of an amino acid sequence selected from SEQ ID NOs: 22-24, HCDR3 comprises or consists of an amino acid sequence of SEQ ID NOs: 25 and 188, LCDR1 comprises or consists of an amino acid sequence of SEQ ID NO: 26, LCDR2 comprises or consists of an amino acid sequence of SEQ ID NO: 27, and LCDR3 comprises or consists of an amino acid sequence selected from SEQ ID NOs: 28-30;
(iii) HCDR1 comprises or consists of an amino acid sequence selected from SEQ ID NOs: 31-33 or 189-190, HCDR2 comprises or consists of an amino acid sequence selected from SEQ ID NOs: 34-37, HCDR3 comprises or consists of an amino acid sequence selected from SEQ ID NOs: 38-40 or 191-192, LCDR1 comprises or consists of an amino acid sequence of SEQ ID NO: 41, LCDR2 comprises or consists of an amino acid sequence of SEQ ID NO: 42, and LCDR3 comprises or consists of an amino acid sequence of SEQ ID NO: 43;
(iv) HCDR1 comprises or consists of an amino acid sequence selected from SEQ ID NOs: 44-47 or 193-195, HCDR2 comprises or consists of an amino acid sequence selected from SEQ ID NOs: 48-52, HCDR3 comprises or consists of an amino acid sequence selected from SEQ ID NOs: 53-56 or 196-198, LCDR1 comprises or consists of an amino acid sequence of SEQ ID NO: 57, LCDR2 comprises or consists of an amino acid sequence of SEQ ID NO: 58, and LCDR3 comprises or consists of an amino acid sequence of SEQ ID NO: 59;
(v) HCDR1 comprises or consists of an amino acid sequence selected from SEQ ID NOs: 60-62 or 199-200, HCDR2 comprises or consists of an amino acid sequence selected from SEQ ID NOs: 6 or 63-65, HCDR3 comprises or consists of an amino acid sequence selected from SEQ ID NOs: 66-68 or 201-202, LCDR1 comprises or consists of an amino acid sequence of SEQ ID NO: 69, LCDR2 comprises or consists of an amino acid sequence of SEQ ID NO: 17, and LCDR3 comprises or consists of an amino acid sequence of SEQ ID NO: 70; or
(vi) HCDR1 comprises or consists of an amino acid sequence selected from SEQ ID NOs: 71-74 or 203-205, HCDR2 comprises or consists of an amino acid sequence selected from SEQ ID NOs: 22 or 75-77, HCDR3 comprises or consists of an amino acid sequence selected from SEQ ID NOs: 78-80 or 206-207, LCDR1 comprises or consists of an amino acid sequence of SEQ ID NO: 81, LCDR2 comprises or consists of an amino acid sequence of SEQ ID NO: 82, and LCDR3 comprises or consists of an amino acid sequence of SEQ ID NO: 83.

In one preferred embodiment, the antibody or the antigen-binding fragment thereof disclosed herein comprises 6 CDR sequences of one of the combinations listed in Table C.

In another preferred embodiment, the antibody or the antigen-binding fragment thereof disclosed herein comprises 6 CDR sequences of one of the combinations listed in Table D.

Variable Regions of Antibodies

A "variable region" or "variable domain" is a domain in the heavy or light chain of an antibody that participates in binding of the antibody to the antigen thereof. A heavy chain variable region (VH) and a light chain variable region (VL) can be further subdivided into hypervariable regions (HVRs, also known as complementarity determining regions (CDRs)) with more conservative regions (i.e., framework regions (FRs)) inserted therebetween. Each VH or VL consists of three CDRs and four FRs, arranged from the N-terminus to C-terminus in the following order: FR1, CDR1, FR2, CDR2, FR3, CDR3, FR4. In some cases, a single VH or VL domain is sufficient to provide antigen-binding specificity. Furthermore, antibodies binding to particular antigens can be isolated by screening libraries of complementarity VL or VH domains by virtue of VH or VL domains from the antibodies binding to the antigens (see, e.g., Portolano, S. et al., *J. Immunol.* 150 (1993) 880-887; Clackson, T. et al., *Nature* 352 (1991) 624-628).

It is known in the art that one or more residues in one or both of the variable regions (i.e., VH and/or VL) can be modified, for example, one or more CDRs and/or one or more framework regions undergo residue modifications, particularly conservative residue substitutions, and the modified antibody still substantially retains at least one biological property (e.g., antigen-binding ability) of the antibody molecule prior to alteration. For example, residues in CDRs may be mutated to improve one or more binding properties (e.g., affinity) of the antibody. The antigen-binding properties or other functional properties of the mutated antibody can be assessed in an in vitro or in vivo assay. Preferably, conservative substitutions are introduced. Preferably, no more than 1, 2, 3, 4, or 5 residue modifications are introduced in the CDRs. Furthermore, residues in framework regions can be mutated, for example, to improve the properties of the antibody. For example, one or more residues in the framework regions may be "back mutated" to corresponding residues of a germline sequence.

CDR grafting is another modification method for antibody variable region known in the art. Since CDR sequences are responsible for most of the antibody-antigen interactions, a recombinant antibody variant that simulates the properties of known antibodies can be constructed. In the antibody variant, CDR sequences from the known antibodies are grafted onto framework regions of different antibodies having different properties. Accordingly, in one embodiment, the present invention relates to an anti-TIGIT antibody or an antigen-binding fragment thereof, wherein the antibody comprises CDR sequences of the heavy and light chain variable regions from one of the antibodies of Table B, and has different framework region sequences. A framework region sequence for substitution can be obtained from a public DNA database, including germline antibody gene sequences, or from published TIGIT antibody sequences. For example, germline DNAs encoding human heavy and light chain variable region genes can be obtained from GenBank database. Antibody protein sequences can be compared to protein sequences in the database using sequence similarity search tools, such as Gapped BLAST. Preferably, the framework region sequence for substitution is structurally similar to a framework sequence of the antibody of the present invention selected for alteration, e.g., a framework sequence having at least 80%, 85%, 90%, 95%, 96%, 97%, 98%, 99% or higher sequence identity.

In yet another embodiment, VH and VL sequences from an exemplary antibody of the present invention (one of the antibodies shown in Table B) and other different anti-TIGIT antibodies (preferably, another antibody shown in Table B) can be "combined and paired" to produce other antibodies of the present invention binding to TIGIT. When these chains are combined and paired, it is preferred that the VH sequence from a particular VH/VL pair is substituted with a structurally similar VH sequence. Likewise, the VL sequence from a particular VH/VL pair is preferably substituted with a structurally similar VL sequence. The binding of such "combined and paired" antibodies to TIGIT can be tested by binding assays known in the art (e.g., ELISA, and other assays described in the examples).

Thus, in one embodiment, the antibody of the present invention comprises or consists of a heavy chain variable region (VH) sequence of any one of the antibodies listed in Table B. In yet another embodiment, the antibody of the present invention comprises a variant of the VH sequence.

In another embodiment, the antibody of the present invention comprises or consists of a light chain variable region (VL) sequence of any one of the antibodies listed in Table B. In yet another embodiment, the antibody of the present invention comprises a variant of the VL sequence.

In yet another embodiment, the antibody of the present invention comprises:
(i) a VH sequence comprising an amino acid sequence set forth in SEQ ID NOs: 84, 85, 86, or 87 or a variant thereof, and/or a VL sequence comprising an amino acid sequence set forth in SEQ ID NO: 104 or a variant thereof,
(ii) a VH sequence comprising an amino acid sequence set forth in SEQ ID NOs: 88, 89, or 90 or a variant thereof, and/or a VL sequence comprising an amino acid sequence set forth in SEQ ID NOs: 105 or 106 or a variant thereof,
(iii) a VH sequence comprising an amino acid sequence set forth in SEQ ID NOs: 91, 92, or 93 or a variant thereof, and/or a VL sequence comprising an amino acid sequence set forth in SEQ ID NO: 107 or a variant thereof,
(iv) a VH sequence comprising an amino acid sequence set forth in SEQ ID NOs: 94, 95, 96, or 97 or a variant thereof, and/or a VL sequence comprising an amino acid sequence set forth in SEQ ID NO: 108 or a variant thereof,
(v) a VH sequence comprising an amino acid sequence set forth in SEQ ID NO: 98, 99, or 100 or a variant thereof, and/or a VL sequence comprising an amino acid sequence set forth in SEQ ID NO: 109 or a variant thereof, or
(vi) a VH sequence comprising an amino acid sequence set forth in SEQ ID NOs: 101, 102, or 103 or a variant thereof, and/or a VL sequence comprising an amino acid sequence set forth in SEQ ID NO: 110 or a variant thereof.

In one embodiment, with respect to amino acid sequence, a variant of the VH sequence has at least 80%, 85%, 90%, 92%, 95%, 97%, 98%, 99% or higher identity relative to the reference VH sequence (preferably, in terms of the full length, or the CDR1, CDR2 and CDR3). In one embodiment, with respect to amino acid sequence, a variant of the VH sequence comprises at least one and no more than 30, 10, 5, 4, 3, 2, 1, or 0 amino acid alteration (preferably amino acid substitution, and more preferably conservative substitution) relative to the reference VH sequence (preferably, in terms of the full length, or the CDR1, CDR2 and CDR3). Preferably, sequence differences do not occur in the CDRs.

In a preferred embodiment, with respect to amino acid sequence, a variant of the VL sequence has at least 80%, 85%, 90%, 92%, 95%, 97%, 98%, 99% or higher identity relative to the reference VL sequence (preferably, in terms of the full length, or the CDR1, CDR2 and CDR3). In a preferred embodiment, with respect to amino acid sequence, a variant of the VL sequence comprises at least one and no more than 30, 10, 5, 4, 3, 2, 1, or 0 amino acid alteration (preferably amino acid substitution, and more preferably conservative substitution) relative to the reference VH sequence (preferably, in terms of the full length, or the CDR1, CDR2 and CDR3). Preferably, sequence differences do not occur in the CDRs.

In a preferred embodiment, the antibody of the present invention comprises or consists of a VH/VL sequence pair of the heavy and light chain variable regions of any one of the antibodies listed in Table B. The present invention also provides a variant of the antibody, e.g., a variant having at least 95-99% identity or comprising no more than 10 amino acid alterations in terms of VH, VL, or VH and VL.

In any of the above embodiments, preferably, in terms of one or more CDRs (preferably all three CDRs), a heavy chain variable region of an antibody variant comprises no more than 10, preferably no more than 5 (e.g., 3, 2, 1, or 0), amino acid alterations (preferably amino acid substitutions, and more preferably conservative substitutions) relative to a reference antibody.

In any of the above embodiments, preferably, in terms of one or more CDRs (preferably all three CDRs), a light chain variable region (VL) of an antibody variant comprises no more than 10, preferably no more than 5 (e.g., 3, 2, 1, or 0), amino acid alterations (preferably amino acid substitutions, and more preferably conservative substitutions) relative to a reference antibody.

Heavy and Light Chains of Antibodies

In some embodiments, the antibody of the present invention comprises a heavy chain Fc region, e.g., an Fc region of the IgG1, IgG2, or IgG4 isotype. In one embodiment, the antibody of the present invention comprises an IgG4-Fc region having a serine-to-proline mutation (S228P) at amino acid residue position 228 (EU numbering). In yet another preferred embodiment, the antibody of the present invention comprises an IgG4-PAA Fc portion. The IgG4-PAA Fc portion has a serine-to-proline mutation (S228P) at position 228, a phenylalanine-to-alanine mutation at position 234 (EU numbering) and a leucine-to-alanine mutation at position 235 (EU numbering). The S228P mutation is a mutation in a hinge region of the tumor constant region that can reduce or eliminate the heterogeneity of an inter-heavy chain disulfide bridge. The F234A and L235A mutations can further reduce the effector function of the human IgG4 isotype (which already has a low effector function). In some embodiments, the antibody of the present invention comprises an IgG4-PAA Fc portion with the heavy chain C-terminus lysine (des-Lys) removed. In some embodiments, the antibody of the present invention comprises a κ light chain constant region, e.g., a human κ light chain constant region.

In yet another preferred embodiment, the Fc region comprises an amino acid sequence of SEQ ID NO: 177, or an amino acid sequence comprising at least one, two, or three but no more than 20, 10 or 5 amino acid alterations relative to the amino acid sequence of SEQ ID NO: 177, or a sequence having at least 95-99% identity to the amino acid sequence of SEQ ID NO: 177.

In a preferred embodiment, the antibody of the present invention comprises a light chain constant region. In a preferred embodiment, the light chain constant region is a human κ light chain constant region. In yet another preferred embodiment, the light chain constant region comprises an amino acid sequence of SEQ ID NO: 209, or an amino acid sequence having at least one, two, or three but no more than 20, 10, or 5 amino acid alterations relative to the amino acid sequence of SEQ ID NO: 209, or an amino acid sequence having at least 95-99% identity to the amino acid sequence of SEQ ID NO: 209.

In some preferred embodiments, the antibody of the present invention comprises a heavy chain comprising an amino acid sequence selected from SEQ ID NOs: 111-130, or an amino acid sequence having at least one, two, or three but no more than 20, 10, or 5 amino acid alterations relative thereto, or an amino acid sequence having at least 80%, 85%, 90%, 92%, 95%, 97%, 98%, 99%, or more identity thereto. Preferably, the amino acid alterations do not occur in the CDRs, and more preferably, the amino acid alterations do not occur in the variable regions.

In some preferred embodiments, the antibody of the present invention comprises a light chain comprising an amino acid sequence selected from SEQ ID NOs: 137-143, or an amino acid sequence having at least one, two, or three but no more than 20, 10 or 5 amino acid alterations relative thereto, or an amino acid sequence having at least 80%, 85%, 90%, 92%, 95%, 97%, 98%, 99%, or more identity thereto. Preferably, the amino acid alterations do not occur in the CDRs, and more preferably, the amino acid alterations do not occur in the variable regions.

In a preferred embodiment, the antibody of the present invention comprises a heavy chain sequence and/or a light chain sequence selected from:

(a) a heavy chain sequence comprising an amino acid sequence selected from SEQ ID NOs: 111-114 or a variant thereof, and/or a light chain sequence comprising an amino acid sequence of SEQ ID NO: 137 or a variant thereof;

(b) a heavy chain sequence comprising an amino acid sequence selected from SEQ ID NOs: 115-117 or a variant thereof, and/or a light chain sequence comprising an amino acid sequence of SEQ ID NO: 138 or 139, or a variant thereof;

(c) a heavy chain sequence comprising an amino acid sequence selected from SEQ ID NOs: 118-120 or a variant thereof, and/or a light chain sequence comprising an amino acid sequence of SEQ ID NO: 140 or a variant thereof;

(d) a heavy chain sequence comprising an amino acid sequence selected from SEQ ID NOs: 121-124 or a variant thereof, and/or a light chain sequence comprising an amino acid sequence of SEQ ID NO: 141 or a variant thereof;

(e) a heavy chain sequence comprising an amino acid sequence selected from SEQ ID NOs: 125-127 or a variant thereof, and/or a light chain sequence comprising an amino acid sequence of SEQ ID NO: 142 or a variant thereof; and (f) a heavy chain sequence comprising an amino acid sequence selected from SEQ ID NOs: 128-130 or a variant thereof, and/or a light chain sequence comprising an amino acid sequence of SEQ ID NO: 143 or a variant thereof, wherein the variant comprises an amino acid sequence comprising at least one, two, or three but no more than 20, 10, or 5 amino acid alterations, or having at least 80%, 85%, 90%, 92%, 95%, 97%, 98%, 99%, or more identity relative to the corresponding reference sequence. Preferably, the amino acid alterations do not occur in the CDRs, and more preferably, the amino acid alterations do not occur in the variable regions.

In one embodiment, residue modifications are made in the constant region of an antibody, for example, to alter the properties of the antibody, such as an effector function.

In some embodiments, the heavy and/or light chain of the anti-TIGIT antibody or the fragment thereof disclosed herein further comprises a signal peptide sequence, e.g., METDTLLLWVLLLWVPGSTG.

Exemplary Antibody Sequences

The present invention provides a fully humanized antibody specifically binding to TIGIT (e.g., human TIGIT) as isolated and characterized in the examples. The VH and VL sequences of variable regions of the exemplary antibodies disclosed herein are listed in Table 3 below. The exemplary CDR sequences of the antibodies are listed in Tables 1 and 2 below. The sequence listing shows the heavy and light chain amino acid sequences of the exemplary antibodies disclosed herein and the coding nucleotide sequences of the variable regions (VH and VL) of the exemplary antibodies disclosed herein.

Antibody Variants

In one aspect, the present invention provides any of the antibodies described herein, particularly variants of the exemplary antibodies listed in Table B. In one embodiment, the antibody variant retains at least 60%, 70%, 80%, 90% or 100% of the biological activity (e.g., antigen-binding ability) of the antibody prior to alteration. In some embodiments, the alteration does not result in loss of the binding ability of an antibody variant to an antigen, and optionally may impart properties such as increased antigen affinity and different effector functions.

It will be understood that the heavy or light chain variable regions, or all CDRs of the antibody may be altered independently or in combination. In some embodiments, there are no more than 1, 2, 3, 4, 5, 6, 7, 8, 9, or 10 amino acid alterations in one or more or all of the three heavy chain CDRs. Preferably, the amino acid alteration refers to an amino acid substitution, preferably a conservative substitution. In some embodiments, there are no more than 1, 2, 3, 4, 5, 6, 7, 8, 9 or 10 amino acid alterations in one or more or all of the three light chain CDRs. In some embodiments, there are no more than 1, 2, 3, 4, 5, 6, 7, 8, 9, or 10 amino acid alterations in one or more or all of the six CDRs. Preferably, the amino acid alteration refers to an amino acid substitution, preferably a conservative substitution. In some embodiments, an antibody variant has at least 80%, 85%, 90%, 95%, 99% or more amino acid identity to a reference antibody in terms of target antibody sequence region. For example, in one embodiment, the antibody of the present invention has at least 90%, 91%, 92%, 93%, 94%, 95%, 96%, 97%, 98%, 99%, or more identity to a reference antibody (e.g., one of the antibodies listed in Table 3) in terms of three heavy chain CDRs. In one embodiment, the antibody of the present invention has at least 90%, 91%, 92%, 93%, 94%, 95%, 96%, 97%, 98%, 99%, or more identity to a reference antibody (e.g., one of the antibodies listed in Table 3) in terms of three light chain CDRs. In another embodiment, the antibody of the present invention has at least 90%, 91%, 92%, 93%, 94%, 95%, 96%, 97%, 98%, 99%, or more identity to a reference antibody (e.g., one of the antibodies listed in Table 3) in terms of six CDRs. In yet another embodiment, the antibody of the present invention has at least 80%, 85%, 90%, 91%, 92%, 93%, 94%, 95%, 96%, 97%, 98%, 99%, or more identity to a reference antibody (e.g., one of the antibodies listed in Table 3) in terms of heavy chain variable region. In yet another embodiment, the antibody of the present invention has at least 80%, 85%, 90%, 91%, 92%, 93%, 94%, 95%, 96%, 97%, 98%, 99%, or more identity to a reference antibody (e.g., one of the antibodies listed in Table 3) in terms of light chain variable region. In yet another embodiment, the antibody of the present invention has at least 80%, 85%, 90%, 91%, 92%, 93%, 94%, 95%, 96%, 97%, 98%, 99%, or more identity to a reference antibody (e.g., one of the antibodies listed in Table 3) in terms of heavy and/or light chain variable regions.

In addition, alterations may be made to an Fc region of an antibody. The alterations to the Fc region may be made alone or in combination with the alterations to the framework regions and/or CDRs described above. The Fc region can be altered, for example, to alter one or more functions of the antibody, such as serum half-life, complement fixation, Fc receptor binding, and/or antigen-dependent cytotoxicity. In addition, the antibody of the present invention may be chemically modified (e.g., linked to PEG), or its glycosylation pattern may be altered.

In certain embodiments, the Fc region may comprise an Fc-region having one or more amino acid replacements that improve the ADCC activity, e.g., replacements at positions 298, 333 and/or 334 (EU numbering of residues) of the Fc-region. In some embodiments, the Fc-region can also be altered to result in altered (i.e., increased or decreased) C1q binding and/or complement dependent cytotoxicity (CDC) (see, e.g., U.S. Pat. No. 6,194,551, WO 99/51642 and Idusogie, E. E. et al., *J. Immunol.* 164 (2000) 4178-4184).

In other embodiments, the Fc region can be altered to increase or decrease its glycosylation degree and/or alter its glycosylation pattern. Addition or deletion of glycosylation sites of the Fc region can be conveniently achieved by producing or removing one or more glycosylation sites through amino acid sequence alteration. For example, one or more amino acid substitutions may be made to eliminate one or more glycosylation sites, thereby eliminating the glycosylation at the sites. Antibodies with altered types of glycosylation can be prepared, such as low-fucosylated or non-fucosylated antibodies with reduced amount of fucosyl residues or antibodies with increased bisecting GlcNac structures. Such altered glycosylation patterns have shown the ability to increase ADCC of antibodies. Herein, antibody variants having at least one galactose residue in the oligosaccharide linked to the Fc region are also considered. The antibody variants may have an increased CDC function.

In certain embodiments, the present invention also considers antibody variants having some but not all effector functions, which makes them a desirable candidate for some applications in which the half-life period of the antibody in vivo is important yet certain effector functions (such as complement and ADCC) are unnecessary or deleterious. For example, the Fc region may comprise a mutation that eliminates or reduces effector functions, such as the human IgG1 Fc region with mutations P329G and/or L234A and L235A, or the human IgG4 Fc region with mutations P329G and/or S228P and L235E.

In certain embodiments, antibodies modified by cysteine engineering may need to be produced, such as "sulfo-MAb", wherein one or more residues of the antibodies are substituted by cysteine residues. For example, the number of cysteine residues in the hinge region of an antibody can be altered, e.g., to facilitate assembly of the light and heavy chains or to increase or decrease the stability of the antibody. See, for example, U.S. Pat. No. 5,677,425.

In certain embodiments, the antibodies provided herein can be further modified to contain other non-protein portions. Suitable portions for antibody derivatization include, but are not limited to, water-soluble polymers. Non-limiting examples of water-soluble polymers include, but are not limited to, polyethylene glycol (PEG) to, e.g., increase the (e.g., serum) half-life of an antibody. Methods for protein PEGylation are known in the art and can be applied to the antibodies of the present invention. See, for example, EP 0154316 and EP 0401384.

II. Polynucleotides, Vectors, and Hosts

The present invention provides a nucleic acid encoding any of the above anti-TIGIT antibodies or fragments thereof, and also provides a vector comprising the nucleic acid. In one embodiment, the vector is an expression vector. In addition, a host cell comprising the nucleic acid or the vector is provided. In one embodiment, the host cell is eukaryotic. In another embodiment, the host cell is selected from a yeast cell, and a mammal cell (e.g., a CHO cell or a 293 cell). In another embodiment, the host cell is prokaryotic.

In one aspect, the present invention provides a nucleic acid encoding any of the above anti-TIGIT antibodies or fragments thereof. The nucleic acid can include a nucleic acid encoding an amino acid sequence of light chain variable regions and/or heavy chain variable regions of the antibodies, or a nucleic acid encoding an amino acid sequence of light chains and/or heavy chains of the antibodies. Exemplary nucleic acid sequences encoding heavy chain variable regions of the antibodies include nucleic acid sequences having at least 80%, 85%, 90%, 91%, 92%, 93%, 94%, 95%, 96%, 97%, 98%, or 99% identity to nucleic acid sequences selected from SEQ ID NOs: 150-169, or include nucleic acid sequences selected from SEQ ID NOs: 150-169. Exemplary nucleic acid sequences encoding light chain variable regions of the antibodies include nucleic acid sequences having at least 80%, 85%, 90%, 91%, 92%, 93%, 94%, 95%, 96%, 97%, 98%, or 99% identity to nucleic acid sequences selected from SEQ ID NOs: 170-176, or include nucleic acid sequences selected from SEQ ID NOs: 170-176. Polypeptides encoded by the polynucleotides can show antigen-binding (TIGIT-binding) ability when expressed in a suitable expression vector.

The present invention also provides a polynucleotide encoding at least one CDR and typically all three CDRs from a heavy chain (VH) sequence or a light chain (VL) sequence of the antibodies binding to TIGIT described above. In some further embodiments, the polynucleotide encodes a complete or substantially complete variable region sequence of heavy chains and/or light chains of the antibodies binding to TIGIT described above.

As will be appreciated by those skilled in the art, each antibody or polypeptide amino acid sequence can be encoded by a variety of nucleic acid sequences because of codon degeneracy.

In a preferred embodiment, the nucleic acid encoding the antibodies of the present invention further comprises a nucleotide sequence encoding a heavy chain Fc region, e.g., an Fc region sequence set forth in SEQ ID NO: 177 or a sequence substantially identical thereto.

In a preferred embodiment, the nucleic acid encoding the antibodies of the present invention further comprises a nucleotide sequence encoding a light chain constant region sequence, e.g., a sequence set forth in SEQ ID NO: 209 or a sequence substantially identical thereto.

By virtue of methods well known in the art, the polynucleotide sequences can be produced by de novo solid phase DNA synthesis or by PCR mutagenesis of existing sequences (e.g., a VH DNA sequence set forth in SEQ ID NOs: 150-169 and a VL DNA sequence set forth in SEQ ID NOs: 170-176) encoding antibodies binding to TIGIT or antigen-binding fragments thereof.

In one embodiment, one or more vectors comprising the nucleic acid of the present invention are provided. In one embodiment, the vector is an expression vector, such as a eukaryotic expression vector. The vector includes, but is not limited to, a virus, a plasmid, a cosmid, a lambda phage, or a yeast artificial chromosome (YAC). In a preferred embodiment, the expression vector of the present invention is a pTT5 expression vector.

In one embodiment, a host cell comprising the vector is provided. The suitable host cell for cloning or expressing the vector encoding the antibody includes a prokaryocyte or a eukaryocyte described herein. For example, antibodies may be produced in bacteria, particularly when glycosylation and Fc effector functions are not required. Expression of antibody fragments and polypeptides in bacteria is described in, for example, U.S. Pat. Nos. 5,648,237, 5,789,199 and 5,840,523, and also described in Charlton, *Methods in Molecular Biology*, Vol. 248 (B. K. C. Lo, ed., Humana Press, Totowa, N.J., 2003), pg. 245-254, which describes expression of antibody fragments in *E. coli*. After expression, antibodies in a soluble fraction can be isolated from bacterial cell paste and can be further purified.

In one embodiment, the host cell is eukaryotic. In another embodiment, the host cell is selected from a yeast cell, a mammalian cell and other cells suitable for preparing an antibody or an antigen-binding fragment thereof. For example, eukaryotic microorganisms, such as filamentous fungi or yeast, are suitable cloning or expression hosts for the vector encoding antibodies. For example, fungus and yeast strains in which a glycosylation pathway has been "humanized" result in the production of antibodies having a partial or complete human glycosylation pattern. See Gerngross, *Nat. Biotech.* 22: 1409-1414 (2004), and Li et al., *Nat. Biotech.* 24:210-215 (2006). Host cells suitable for expressing glycosylated antibodies may also be derived from multicellular organisms (invertebrates and vertebrates). Vertebrate cells may also be used as hosts. For example, a mammalian cell line engineered to be suitable for suspension growth may be used. Some examples of useful mammalian host cell lines are monkey kidney CV1 lines (COS-7) transformed with SV40, human embryonic kidney lines (293 HEK or 293 cells, as described in, e.g., Graham et al., *J. Gen Virol.* 36:59 (1977)) and the like. Other useful mammalian host cell lines include Chinese hamster ovary (CHO) cells including DHFR⁻ CHO cells (Urlaub et al., *Proc. Natl. Acad. Sci. USA* 77: 216 (1980)), and myeloma cell lines such as Y0, NS0, and Sp2/0. For reviews of certain mammalian host cell lines suitable for antibody production, see, e.g., Yazaki and Wu, *Methods in Molecular Biology*, Vol. 248 (B. K. C. Lo, ed., Humana Press, Totowa, N.J.), pg. 255-268 (2003).

III. Preparation of Antibodies

In one embodiment, a method for preparing an anti-TIGIT antibody is provided, wherein the method comprises culturing host cells comprising a nucleic acid encoding the antibody under conditions suitable for antibody expression, as provided above, and optionally isolating the antibody from the host cells (or host cell culture media). For recombinant production of the anti-TIGIT antibody, a nucleic acid encoding the antibody (e.g., the antibody described above) is isolated and inserted into one or more vectors for further cloning and/or expression in the host cells. Such a nucleic acid can be easily isolated and sequenced by using conventional procedures (e.g., by using oligonucleotide probes that are capable of specifically binding to genes encoding heavy and light chains of antibodies).

IV. Assay

The anti-TIGIT antibodies provided herein can be identified, screened, or characterized for physical/chemical properties and/or bioactivity thereof through a variety of assays known in the art.

In one aspect, the antibodies of the present invention are tested for antigen-binding activity. For example, the binding to human TIGIT can be determined by methods known in the art, such as ELISA, Western blot, and the like, or by the exemplary methods disclosed in the examples herein. For example, the assay can be performed using flow cytometry, wherein the antibodies react with a cell line expressing human TIGIT, e.g., CHO cells transfected to express human TIGIT on cell surfaces. Flow cytometry is also applicable to other cells, including T cells expressing natural TIGIT. Alternatively, binding of the antibodies, including binding kinetics (e.g., $K_D$), can be determined in a biological optical interferometry assay using recombinant TIGIT proteins. In some embodiments, for example, a Fortebio affinity assay is adopted.

In another aspect, a competition assay can be used to identify an antibody that competes for binding to TIGIT with any of the anti-TIGIT antibodies disclosed herein. In certain embodiments, such a competitive antibody binds to the same or an overlapping epitope (e.g., a linear or conformational epitope) as any of the anti-TIGIT antibodies disclosed herein. A detailed exemplary method for locating an epitope to which an antibody binds is described in Morris (1996) "Epitope Mapping Protocols", *Methods in Molecular Biology* vol. 66 (Humana Press, Totowa, N.J.).

The present invention also provides an assay for identifying anti-TIGIT antibodies having bioactivity. The bioactivity can include, for example, binding to TIGIT (e.g., human TIGIT), blocking binding of TIGIT (e.g., human TIGIT) to CD155 molecules, blocking TIGIT-mediated inhibitory signaling, increasing the production of IL2 in T cells, and/or inhibiting tumor growth. For example, the ability of antibodies in inhibiting tumor growth are tested in an in vivo tumor suppression model (see, e.g., Example 6). Antibodies having such bioactivity in vivo and/or in vitro are also provided herein.

It will be appreciated that any of the above assays can be performed using the immunoconjugates or multispecific antibodies of the present invention to replace or supplement anti-TIGIT antibodies.

V. Multispecific Antibodies

In a further aspect, the present invention provides a multispecific (including bispecific) antibody molecule that specifically binds to TIGIT, preferably human TIGIT. In one embodiment, among multispecific antibodies, the antibodies (or the antigen-binding fragments thereof) of the present invention have a first binding specificity for TIGIT. In yet another embodiment, the multispecific antibodies further have a second binding specificity, or, in yet another embodiment, have a second binding specificity and a third binding specificity. In yet another embodiment, the multispecific antibodies are bispecific antibodies.

In one embodiment, the binding specificity is dependent on a "binding site" or an "antigen-binding site" (a region of an antibody molecule that actually binds to an antigen) of the antibodies. In a preferred embodiment, the antigen-binding site is formed by a VH/VL pair consisting of a light chain variable domain (VL) and a heavy chain variable domain (VH) of the antibodies. Thus, in one embodiment, the "multispecific" antibodies have at least two antigen-binding sites, each of which can bind to a different epitope of the same antigen or to a different epitope of a different antigen.

For multispecific antibodies and preparation thereof, see, for example, the descriptions in WO 2009/080251, WO 2009/080252, WO 2009/080253, WO 2009/080254, WO 2010/112193, WO 2010/115589, WO 2010/136172, WO 2010/145792, and WO 2010/145793.

VI. Immunoconjugates

In yet another aspect, the present invention provides an immunoconjugate produced by conjugating the antibodies of the present invention to a heterologous molecule. In one embodiment, in the immunoconjugate, the antibodies (or the antigen-binding fragments thereof) of the present invention are conjugated to a therapeutic or diagnostic agent. In some embodiments, the antibodies of the present invention can be conjugated to a heterologous molecule in the form of full-length antibodies or antibody fragments. For example, the antibodies are conjugated in the form of Fab fragments, Fab' fragments, F(ab)'$_2$ fragments, single chain scFab antibodies, single chain scFvs, or other fragments.

In some embodiments, the antibodies of the present invention are conjugated to a therapeutic molecule. Linkers can be used to covalently link the antibodies to the therapeutic molecule. Suitable linkers include chemical linkers or peptide linkers.

In other embodiments, the antibodies of the present invention can be conjugated to a diagnostic or detectable agent. Such conjugates can be used as part of a clinical testing method (e.g., to determine the efficacy of a particular therapy) to monitor or predict the onset, formation, progression, and/or severity of a disease or disorder. Such diagnosis and detection can be achieved by coupling the antibodies to a detectable agent.

VII. Pharmaceutical Compositions and Pharmaceutical Preparations

The present invention also provides a composition (including a pharmaceutical composition or a pharmaceutical preparation) comprising the anti-TIGIT antibodies or immunoconjugates thereof or multispecific antibodies, and a composition comprising a polynucleotide encoding the anti-TIGIT antibodies or immunoconjugates thereof or multispecific antibodies. Such compositions can further optionally comprise suitable pharmaceutical adjuvants, such as a pharmaceutical carrier, a pharmaceutical excipient, and the like known in the art, including buffers.

In one embodiment, the composition further comprises a second therapeutic agent. The second therapeutic agent can be selected from a group including, but not limited to, such as anti-PD-1 antibodies and anti-PD-L1 antibodies. Preferably, the second therapeutic agent is a PD-1 antagonist, in particular an anti-PD-1 antibody.

The pharmaceutical carrier applicable to the present invention may be sterile liquid, such as water and oil, including those derived from petroleum, animals, plants or synthesis, such as peanut oil, soybean oil, mineral oil, sesame oil, etc. Water is a preferred carrier when the pharmaceutical composition is administered intravenously. Saline solutions, aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, etc. For use and application of excipients, see *Handbook of Pharmaceutical Excipients*, the fifth edition, R. C. Rowe, P. J. Seskey and S. C. Owen, Pharmaceutical Press, London, Chicago. The composition may further comprise a small quantity of wetting agents or emulsifiers, or pH buffer, if desired. The composition may take the form of a solution, a suspension, an emulsion, a tablet, a pill, a capsule, a powder, a sustained release preparation, and the like. Oral preparations may comprise a standard carrier, such as pharmaceutical grade mannitol, lactose, starch, magnesium stearate, and saccharin.

A pharmaceutical preparation comprising the present invention can be prepared by mixing the anti-TIGIT antibodies, immunoconjugates or multispecific antibodies of the present invention of a desired purity with one or more optional pharmaceutical adjuvants, preferably in the form of a lyophilized preparation or an aqueous solution (*Remington's Pharmaceutical Sciences*, 16 th edition, Osol, A. eds. (1980)).

An exemplary lyophilized antibody preparation is described in U.S. Pat. No. 6,267,958. The aqueous antibody preparation includes those described in U.S. Pat. No. 6,171, 586 and WO 2006/044908, and the latter preparation comprises a histidine-acetate buffer.

The pharmaceutical composition or preparation of the present invention can further comprise one or more other active ingredients which are required for a specific indication being treated, preferably active ingredients having complementary activities that do not adversely affect one another. For example, it may be desirable to further provide other anti-cancer active ingredients, such as PD-1 binding antagonists or PD-L1 binding antagonists, e.g., an anti-PD-1 antibody or an anti-PD-L1 antibody. The active ingredients are suitably combined in an amount effective for an intended purpose.

A sustained release preparation can be prepared. Suitable examples of the sustained release preparation include a semipermeable matrix of a solid hydrophobic polymer comprising an antibody. The matrix is in the form of a shaped article, such as a film or a microcapsule.

For other components of the pharmaceutical preparation, see also those disclosed in WO 2015/153513.

VIII. Combination Products

In one aspect, the present invention also provides a combination product comprising the antibodies or the antigen-binding fragments thereof, bispecific antibodies, or immunoconjugates of the present invention, and one or more other therapeutic agents (e.g., a chemotherapeutic agent, other antibodies, a cytotoxic agent, a vaccine, an anti-infection active agent). The combination product of the present invention can be used in a therapeutic method disclosed herein.

In some embodiments, the combination product is provided, wherein the other therapeutic agents refer to, for example, a therapeutic agent, such as an antibody, which is effective to stimulate an immune response and thus further enhance, stimulate, or upregulate the immune response in a subject. In some embodiments, the other antibodies refer to, e.g., an anti-PD-1 antibody or an anti-PD-L1 antibody.

In some embodiments, the combination product is used for preventing or treating a tumor. In some embodiments, the tumor is a cancer, e.g., a gastrointestinal cancer (such as a gastric cancer, a rectal cancer, a colon cancer, and a colorectal cancer), or a skin cancer (such as malignant melanoma). In some embodiments, the combination product is used for preventing or treating an infection, such as a bacterial infection, a viral infection, a fungal infection, a protozoan infection, and the like.

IX. Therapeutic Method and Use of Antibodies

Herein, the terms "individual" and "subject" can be used interchangeably and refer to a mammal. Mammals include, but are not limited to, domesticated animals (e.g., cows, sheep, cats, dogs, and horses), primates (e.g., human and non-human primates such as monkeys), rabbits and rodents (e.g., mice and rats). In particular, a subject is a human.

Herein, the term "treating" refers to a clinical intervention intending to alter the natural progress of a disease in an individual being treated. Desired therapeutic effects include, but are not limited to, preventing the occurrence or recurrence of diseases, alleviating symptoms, reducing any direct or indirect pathological outcomes of diseases, preventing metastasis, delaying disease progression, improving or alleviating conditions, and improving prognosis.

In one aspect, the present invention relates to a method for enhancing an immune response of the body of a subject, wherein the method comprises administering to the subject an effective amount of any of the anti-TIGIT antibodies fragments thereof described herein, an immunoconjugate or a multispecific antibody comprising the antibodies or fragments thereof, or a pharmaceutical composition. In some embodiments, the anti-TIGIT antibodies or antigen-binding fragments thereof of the present invention are administered to a subject carrying a tumor to stimulate an anti-tumor immune response. In other embodiments, the antibodies or the antigen-binding fragments thereof of the present invention are administered to a subject carrying an infection to stimulate an anti-infection immune response.

In another aspect, the present invention relates to a method for treating a tumor, e.g., a cancer, in a subject, wherein the method comprises administering to the subject an effective amount of any of the anti-TIGIT antibodies or fragments thereof described herein, an immunoconjugate or a multispecific antibody comprising the antibodies or fragments thereof, or a pharmaceutical composition. The cancer may be at an early, intermediate, or advanced stage or a metastatic cancer.

TIGIT has been demonstrated to be highly expressed on the surface of human tumor-infiltrating $CD8^+$ T cells. In some embodiments, the method of the present invention is used for treating a cancer, particularly a solid tumor infiltrated with tumor-infiltrating lymphocytes expressing TIGIT.

In one embodiment, the cancer is a gastrointestinal cancer, such as a colon cancer.

In some embodiments, the tumor or tumor cell can be selected from a colorectal neoplasm, an ovarian neoplasm, a pancreatic neoplasm, a lung neoplasm, a hepatic neoplasm, a breast neoplasm, a renal neoplasm, a prostate neoplasm, a gastrointestinal neoplasm, a melanoma, a cervical neoplasm, a bladder neoplasm, a glioblastoma, and a head and neck neoplasm. In some embodiments, the cancer can be selected from a colorectal cancer, an ovarian cancer, a pancreatic cancer, a lung cancer, a liver cancer, a breast cancer, a renal cancer, a prostate cancer, a gastrointestinal cancer, a melanoma, a cervical cancer, a bladder cancer, a glioblastoma, and a head and neck cancer.

In some embodiments, a method for treating a tumor (e.g., a cancer) is provided herein, wherein the method comprises administering to a subject the anti-TIGIT antibodies of the present invention and antagonistic anti-PD-1 antibodies. In some embodiments, the method is used for treating a tumor co-expressing TIGTI and PD-1, e.g., melanoma co-expressing TIGIT and PD-1 (Chauvin et al. (2015) *J. Clin. Invest.* 125:2046), a non-small cell lung cancer (NSCLC), and a renal cell carcinoma (RCC).

In another aspect, the present invention relates to a method for treating an infectious disease, e.g., a chronic infection, in a subject, wherein the method comprises administering to the subject an effective amount of any of the anti-TIGIT antibodies or fragments thereof described herein, an immunoconjugate or a multispecific antibody comprising the antibodies or fragments thereof, or a pharmaceutical composition. In one embodiment, the infection is a virus infection.

In one embodiment, the infectious disease results from a virus infection. Some examples of pathogenic viruses include hepatitis viruses (A, B, and C), influenza viruses (A, B, and C), HIV, herpes viruses (e.g., VZV, HSV-1, HAV-6, HSV-II, CMV, and Epstein Barr virus), adenoviruses, flaviviruses, echoviruses, rhinoviruses, coxsackieviruses, coronaviruses, respiratory syncytial viruses, mumps viruses, rotaviruses, measles viruses, rubella viruses, parvoviruses, vaccinia viruses, HTLV viruses, dengue viruses, papillary carcinomas, molluscum viruses, polioviruses, rabies viruses, JC viruses, and arthropod-borne encephalitis viruses.

In some embodiments, the method described herein further comprises administering to the subject one or more therapies in combination (e.g., therapeutic modality and/or other therapeutic agents). In some embodiments, the therapeutic modality includes a surgical treatment and/or a radiation therapy.

In some embodiments, a T cell response can be stimulated by a combination of the anti-TIGIT antibodies of the present invention and one or more therapeutic agents. In some embodiments, in addition to administering the antibodies of present the invention, the method of the present invention further comprises administering at least one additional immunostimulatory antibody, e.g., an anti-PD-1 antibody and an anti-PD-L1 antibody, which can be, e.g., fully humanized, chimeric, or humanized In other embodiments, other therapeutic agents that can be used in combination with the antibodies of the present invention are PD-1 binding antagonists and PD-L1 binding antagonists. Alternative names for "PD-1" include CD279 and SLEB2. Alternative names for "PD-L1" include B7-H1, B7-4, CD274, and B7-H. In some embodiments, PD-1 and PD-L1 are human PD-1 and human PD-L1, respectively. In some embodiments, the PD-1 binding antagonist is a molecule that inhibits the binding of PD-1 to a ligand/binding partner thereof. In a particular aspect, the PD-1 ligand/binding partner is PD-L1. In another embodiment, the PD-L1 binding antagonist is a molecule that inhibits the binding of PD-L1 to a binding partner thereof. In a particular aspect, the PD-L1 binding partner is PD-1. The antagonist may be an antibody, an antigen-binding fragment, an immunoadhesin, a fusion protein, or an oligopeptide. In some embodiments, the PD-1 binding antagonist is an anti-PD-1 antibody (e.g., a human antibody, a humanized antibody, or a chimeric antibody). In some embodiments, the anti-PD-1 antibody is selected from: IBI308 (Sintilimab monoclonal antibody, WO2017/025016A1), MDX-1106 (nivolumab, OPDIVO), Merck 3475 (MK-3475, pembrolizumab, KEYTRUDA) and CT-011 (pidilizumab). In some embodiments, the anti-PD-1 antibody is MDX-1106. In some embodiments, the anti-PD-1 antibody is nivolumab (CAS Registry Number: 946414-94-4). In a preferred embodiment, the anti-PD-1 antibody is the "Antibody C" as described herein.

In some further embodiments, the anti-TIGIT antibodies or fragments thereof, alone or in combination with the PD-1/PD-L1 binding antagonist, can also be administered in combination with one or more other therapies, e.g., therapeutic modalities and/or therapeutic agents. In some embodiments, the therapeutic modalities include a surgery (e.g., a tumor resection), a radiation therapy (e.g., an external beam therapy that involves a three-dimensional conformal radiation therapy in which an irradiation region is designed), a partial irradiation (e.g., an irradiation directed to a preselected target or an organ), a focused irradiations, and the like.

In some embodiments, the anti-TIGIT antibodies or antigen-binding fragments thereof of the present invention can be administered in combination with a chemotherapy or a chemotherapeutic agent. In some embodiments, the anti-TIGIT antibodies or antigen-binding fragments thereof of the present invention can be administered in combination with a radiation therapy or a radiotherapeutic agent. In some embodiments, the anti-TIGIT antibodies or antigen-binding fragments thereof of the present invention can be administered in combination with a targeted therapy or a targeted therapeutic agent. In some embodiments, the anti-TIGIT antibodies or antigen-binding fragments thereof of the present invention can be administered in combination with an immunotherapy or an immunotherapeutic agent, e.g., a monoclonal antibody.

The antibody of the present invention (the pharmaceutical composition or the immunoconjugate comprising the same, and any other therapeutic agents) can be administered by any suitable method, including parenteral administration, intrapulmonary administration, intranasal administration, and intralesional administration if required by local treatment. Parenteral infusion includes intramuscular, intravenous, intra-arterial, intraperitoneal, or subcutaneous administration. The medicaments may be administered by any suitable means, such as injection, e.g., intravenous or subcutaneous injection, to some extent depending on short-term or long-term treatment. Various administration schedules are encompassed herein, including, but not limited to, single administration or multiple administrations, bolus injections, and pulse infusions at multiple time points.

In order to prevent or treat diseases, the appropriate dosage of the antibody of the present invention (when used alone or in combination with one or more other additional therapeutic agents) will depend on types of diseases to be treated, types of antibodies, severity and progression of the disease, purpose of administration (prophylactic or therapeutic), previous treatments, clinical histories of patients, responses to the antibody, and the discretion of an attending physician. The antibody is suitably administered to a patient through a single treatment or through a series of treatments.

In the methods described above, the composition, multispecific antibody, or immunoconjugate of the present invention can be administered in place of the antibody or the antigen-binding fragment thereof disclosed herein. Alternatively, in the methods, the composition, multispecific antibody, or immunoconjugate of the present invention can be further administered after the antibody or the antigen-binding fragment thereof disclosed herein is administered.

In yet another aspect, the present invention provides a use of the anti-TIGIT antibody, composition, immunoconjugate, and multispecific antibody of the present invention in preparation of drugs used for the methods described above (e.g., used for treatment).

X. Methods and Compositions for Diagnosis and Detection

In yet another aspect, the present invention relates to a method and a kit for detecting TIGIT in a sample, wherein the method comprises: (a) contacting the sample with the antibody or the antigen-binding fragment thereof or the immunoconjugate disclosed herein; and (b) detecting the formation of a complex of the antibody or the antigen-binding fragment thereof or the immunoconjugate with a TIGIT protein. In some embodiments, the sample is from a cancer patient, e.g., a skin cancer patient. The detection may be in vitro or in vivo.

The term "detection" used herein includes quantitative or qualitative detection, and exemplary detections may involve immunohistochemistry, immunocytochemistry, flow cytometry (e.g., FACS), magnetic beads complexed with antibody molecules, ELISA, and PCR techniques (e.g., RT-PCR). In certain embodiments, the biological sample is blood, serum, or other liquid samples of biological origin. In certain embodiments, the biological sample includes cells or tissues. In some embodiments, the biological sample is derived from a proliferative or cancerous lesion. In certain embodiments, the TIGIT to be detected is human TIGIT.

In one embodiment, the anti-TIGIT antibody is used to select a subject suitable for treatment with the anti-TIGIT antibody, e.g., wherein TIGIT is a biomarker for selecting the subject. In one embodiment, the antibody of the present invention can be used to diagnose cancers or tumors, e.g., to assess (e.g., monitor) the treatment or progression, diagnosis and/or staging of a disease (e.g., the hyperproliferative or cancerous disease) described herein in a subject.

In certain embodiments, a labeled anti-TIGIT antibody is provided. The label includes, but is not limited to, a label or moiety (e.g., a fluorescent label, a chromophoric label, an electron-dense label, a chemiluminescent label, and a radioactive label) that is detected directly, as well as a moiety that is detected indirectly, such as an enzyme or a ligand, for example, by an enzymatic reaction or a molecular interaction. Exemplary labels include, but are not limited to, radioisotopes of $^{32}P$, $^{14}C$, $^{125}I$, $^{3}H$ and $^{131}I$, fluorophores (such as rare earth chelates or fluorescein) and derivatives thereof, rhodamine and derivatives thereof, dansyl, umbelliferone, luceriferase (such as firefly luciferase and bacterial luciferase (U.S. Pat. No. 4,737,456)), fluorescein, 2,3-dihydrophthalazinedione, horseradish peroxidase (HR), alkaline phosphatase, β-galactosidase, glucoamylase, lysozyme, carbohydrate oxidase (such as glucose oxidase, galactose oxidase and glucose-6-phosphate dehydrogenase), heterocyclic oxidase (such as uricase and xanthine oxidase), enzymes oxidizing dye precursors with hydrogen peroxide (such as HR, lactoperoxidase, or microperoxidase), biotin/avidin, spin labels, phage labels, stable free radicals, etc.

The following examples are described to assist in understanding the present invention. The examples are not intended and should not be interpreted in any way as limiting the protection scope of the present invention.

TABLE 1

CDR sequences of exemplary antibodies of the present invention

| Antibody Kabat numbering position | SEQ ID NO: HCDR1 H27-35B | HCDR1 | SEQ ID NO: HCDR2 H50-65 | HCDR2 | SEQ ID NO: HCDR3 H93-102 | HCDR3 | SEQ ID NO: LCDR1 L24-34 | LCDR1 | SEQ ID NO: LCDR2 L50-56 | LCDR2 | SEQ ID NO: LCDR3 L89-97 | LCDR3 |
|---|---|---|---|---|---|---|---|---|---|---|---|---|
| ADI-27238 | 1 | YTFTSYYMS | 1 | IINPSGGSTSYAQKFQG | 6 | ARARYPSSWPYGMDV | 11 | RASQSINSYLN | 16 | AASSLQS | 17 | QQSLLTPFT | 18 |
| ADI-30263 | 2 | YTFLSYYMN | 2 | IIDPSGGRTSYAQKFQG | 7 | ARARYPSSWPYGTDV | 12 | RASQSINSYLN | 16 | AASSLQS | 17 | QQSLLTPFT | 18 |
| ADI-30267 | 3 | YTFRSYYMS | 3 | IIDPSGGRTSFAQKFQG | 8 | ARARYPESWPYGMDV | 13 | RASQSINSYLN | 16 | AASSLQS | 17 | QQSLLTPFT | 18 |
| ADI-30268 | 4 | YTFGSYYMG | 4 | IIDPSGGRTSYARKFQG | 9 | ARARTPSSWPYGMDV | 14 | RASQSINSYLN | 16 | AASSLQS | 17 | QQSLLTPFT | 18 |
| Consensus sequence | 5 | YTFX$_1$SYYMX$_2$ (wherein X$_1$ is selected from T, L, R, G and a conservatively substituted residue thereof, and X$_2$ is selected from S, N, G and a conservatively substituted residue thereof) | 5 | IIX$_1$PSGGX$_2$TSX$_3$AX$_4$KFQG (wherein X$_1$ is selected from N, D and a conservatively substituted residue thereof, X$_2$ is selected from S, R and a conservatively substituted residue thereof, X$_3$ is selected from Y, F and a conservatively substituted residue thereof, and X$_4$ is selected from Q, R and a conservatively substituted residue thereof) | 10 | ARARX$_1$PSSWPYGX$_2$DV (wherein X$_1$ is selected from Y, T and a conservatively substituted residue thereof, and X$_2$ is selected from M, T and a conservatively substituted residue thereof) | 15 | RASQSINSYLN | | | | | |
| ADI-27243 | 19 | GSISSSRYYWG | 19 | SIYYSGSTYYNPSLKS | 22 | ARDGLYHTPEYFQH | 25 | RASQSVSSYLA | 26 | DASNRAT | 27 | QQRFAFPYT | 28 |
| ADI-30302 | 20 | GSIGSSQYYWG | 20 | SIYRSGGTYYNPSLKS | 23 | ARDGLYHTPEYFQH | 25 | RASQSVSSYLA | 26 | DASNRAT | 27 | QQRFAFPYT | 28 |
| ADI-30336 | 19 | GSISSSRYYWG | 19 | SIYYSGSTYYNPSLKS | 22 | ARDGLYHTPEYFQH | 25 | RASQSVSSYLA | 26 | DASNRAT | 27 | QQRFAHPYT | 29 |
| Consensus sequence | 21 | GSIX$_1$SSX$_2$YYWG (wherein X$_1$ is selected from S, G and a conservatively substituted residue thereof, and X$_2$ is selected from R, Q and a conservatively substituted residue thereof) | 21 | SIYX$_1$SGX$_2$TYYNPSLKS (wherein X$_1$ is selected from Y, R and a conservatively substituted residue thereof, and X$_2$ is selected from S, G and a conservatively substituted residue thereof) | 24 | ARDGLYHTPEYFQH | 25 | RASQSVSSYLA | 26 | DASNRAT | 27 | QQRFAX$_1$PYT (wherein X$_1$ is selected from F, H and a conservatively substituted residue thereof) | 30 |
| ADI-27278 | 31 | FTFSSYSMN | 31 | YISGSSSTIYYADSVKG | 34 | ARHRIADSPSRAFDI | 38 | KSSQSVLFSSNNK-NYLA | 41 | WASTRES | 42 | QQSYFFPT | 43 |
| ADI-30293 | 31 | FTFSSYSMN | 31 | YI-SSSGTINYADSVKG | 35 | ARHRIADSPSRAFDI | 38 | KSSQSVLFSSNNK-NYLA | 41 | WASTRES | 42 | QQSYFFPT | 43 |

TABLE 1-continued

CDR sequences of exemplary antibodies of the present invention

| Antibody Kabat numbering position | HCDR1 H27-35B | SEQ ID NO: | HCDR2 H50-65 | SEQ ID NO: | HCDR3 H93-102 | SEQ ID NO: | LCDR1 L24-34 | SEQ ID NO: | LCDR2 L50-56 | SEQ ID NO: | LCDR3 L89-97 | SEQ ID NO: |
|---|---|---|---|---|---|---|---|---|---|---|---|---|
| ADI-30296 | FTIGGYSMN | 32 | YI-SSSSTIHYADSVKG | | ARHRIGRSPSRAFDI | 36 | KSSQSVLFSSNNK-NYLA | 39 | WASTRES | 41 | QQSYFFPT | 43 |
| Consensus sequence | FTX₁X₂X₃YSMN (wherein X₁ is selected from F, I and a conservatively substituted residue thereof, X₂ is selected from G, S and a conservatively substituted residue thereof, and X₃ is selected from S, G and a conservatively substituted residue thereof) | | YIX₁X₂SSX₃TIX₄YADSVKG (wherein X₁ is selected from F, I and a conservatively substituted residue thereof, X₂ is selected from G, S and a conservatively substituted residue thereof, X₃ is selected from S, G and a conservatively substituted residue thereof, and X₄ is selected from Y, N, H and a conservatively substituted residue thereof) | | ARHRIX₁X₂SPSRAFDI (wherein X₁ is selected from A, G and a conservatively substituted residue thereof, and X₂ is selected from D, R or a conservatively substituted residue thereof) | 37 | KSSQSVLFSSNNK-NYLA | 40 | WASTRES | 42 | QQSYFFPT | 43 |
| ADI-27291 | FTFSSYAMS | 44 | AISGSGGSTYYADSVKG | | AKDPGTDSSGYYYIWRY | 48 | RASQSVSSNLA | 53 | SASTRAT | 57 | QQVPHPPFT | 59 |
| ADI-30283 | FTFSPYGMS | 45 | SISGSGGRTYYADSVKG | | AKDPGTDSSGYYYIWRY | 49 | RASQSVSSNLA | 53 | SASTRAT | 57 | QQVPHPPFT | 59 |
| ADI-30286 | FTFGPYGMS | 46 | AISGSGASTWYADSVKG | | AKDPGTHYSGYYYIWRY | 50 | RASQSVSSNLA | 54 | SASTRAT | 57 | QQVPHPPFT | 59 |
| ADI-30288 | FTFGPYGMS | 46 | AISGSGASTWHADSVKG | | AKDPGTDSTGYYYIWRY | 51 | RASQSVSSNLA | 55 | SASTRAT | 57 | QQVPHPPFT | 59 |
| Consensus sequence | FTFX₁X₂YX₃MS (wherein X₁ is selected from S, G and a conservatively substituted residue thereof, X₂ is selected from S, P and a conservatively substituted residue thereof, and X₃ is selected from A, G and a conservatively substituted residue thereof) | 47 | X₁ISGSGX₂X₃TX₄X₅ADSVKG (wherein X₁ is selected from A, S and a conservatively substituted residue thereof, X₂ iselected from G, A and a conservatively substituted residue thereof, X₃ is selected from S, R and a conservatively substituted residue thereof, X₄ is selected from Y, W and a conservatively substituted residue thereof, and X₅ is selected from Y, H and a conservatively substituted residue thereof) | | AKDPGTX₁X₂X₃GYYYIWRY (wherein X₁ is selected from D, H and a conservatively substituted residue thereof, X₂ is selected from S, Y and a conservatively substituted residue thereof, and X₃ is selected from S, T and a conservatively substituted residue thereof) | 52 | RASQSVSSNLA | 56 | SASTRAT | 57 | QQVPHPPFT | 59 |

TABLE 1-continued

CDR sequences of exemplary antibodies of the present invention

| Antibody | HCDR1 H27-35B | SEQ ID NO: H27-35B | HCDR2 H50-65 | SEQ ID NO: H50-65 | HCDR3 H93-102 | SEQ ID NO: H93-102 | LCDR1 L24-34 | SEQ ID NO: L24-34 | LCDR2 L50-56 | SEQ ID NO: L50-56 | LCDR3 L89-97 | SEQ ID NO: L89-97 |
|---|---|---|---|---|---|---|---|---|---|---|---|---|
| ADI-27297 | YTFTSYYMH | | IINPSGGSTSYAQKFQG | 60 | ARDHDIAAAGRLADY | 6 | RASQGISSWLA | 66 | AASSLQS | 69 | QQAVILPIT | 17 | 70 |
| ADI-30272 | YTFTEYYMH | | IISPSAGSTSYAQKFQG | 61 | ARDHDIAAAGRLADY | 63 | RASQGISSWLA | 66 | AASSLQS | 69 | QQAVILPIT | 17 | 70 |
| ADI-30278 | YTFTEYYMH | | IISPSAGSTKYAQKFQG | 61 | ARDHDIRLAGRLADY | 64 | RASQGISSWLA | 67 | AASSLQS | 69 | QQAVILPIT | 17 | 70 |
| Consensus sequence | YTFTX$_1$YYMH (wherein X$_1$ is selected from S, E and a conservatively substituted residue thereof) | | IIX$_1$PSX$_2$GSTX$_3$YAQKFQG (wherein X$_1$ is selected from N, S and a conservatively substituted residue thereof, X$_2$ is selected from G, A and a conservatively substituted residue thereof, and X$_3$ is selected from S, K and a conservatively substituted residue thereof) | | ARDHDIX$_1$X$_2$AGRLADY (wherein X$_1$ is selected from A, R and a conservatively substituted residue thereof, and X$_2$ is selected from A, L and a conservatively substituted residue thereof) | 65 | RASQGISSWLA | 68 | AASSLQS | 69 | QQAVILPIT | 17 | 70 |
| ADI-27301 | GSISSSSYYWG | | SIYYSGSTYYNPSLKS | 71 | AREAGRGTTGLLFDY | 22 | RASQSISSWLA | 78 | KASSLES | 81 | QQYGILPRT | 82 | 83 |
| ADI-30306 | GSISSLYYWG | | SIYYSGSTFYNPSFKS | 72 | AREAGRGTTGLLFDY | 75 | RASQSISSWLA | 78 | KASSLES | 81 | QQYGILPRT | 82 | 83 |
| ADI-30311 | GSIASSVYYWG | | SIYYSGSTWYNPSLKS | 73 | AREAGRTGTGLLFDY | 76 | RASQSISSWLA | 79 | KASSLES | 81 | QQYGILPRT | 82 | 83 |
| Consensus sequence | GSIX$_1$SSX$_2$YYWG (wherein X$_1$ is selected from A, S, Y, F, W and a conservatively substituted residue thereof, and X$_2$ is selected from S, L, V and a conservatively substituted residue thereof) | | SIYYSGSTX$_1$YNPSX$_2$KS (wherein X$_1$ is selected from Y, F, W and a conservatively substituted residue thereof, and X$_2$ is selected from L, F and a conservatively substituted residue thereof) | 74 | AREAGRX$_1$X$_2$TGLLFDY (wherein X$_1$ is selected from G, T and a conservatively substituted residue thereof, and X$_2$ is selected from T, G and a conservatively substituted residue thereof) | 77 | RASQSISSWLA | 80 | KASSLES | 81 | QQYGILPRT | 82 | 83 |

TABLE 2

CDR sequences of exemplary antibodies of the present invention

| Antibody | HCDR1-AbM | SEQ | HCDR2-Kabat | SEQ | HCDR3-Kabat | SEQ | LCDR1-Kabat | SEQ | LCDR2-Kabat | SEQ | LCDR3-Kabat | SEQ |
|---|---|---|---|---|---|---|---|---|---|---|---|---|
| ADI-27238 | GYTFTSYYMS | 178 | IINPSGGSTSYAQKFQG | 6 | ARYPSSWPYGMDV | 182 | RASQSINSYLN | 16 | AASSLQS | 17 | QQSLLTPFT | 18 |
| ADI-30263 | GYTFLSYYMN | 179 | IIDPSGGRTSYAQKFQG | 7 | ARYPSSWPYGTDV | 183 | RASQSINSYLN | 16 | AASSLQS | 17 | QQSLLTPFT | 18 |
| ADI-30267 | GYTFRSYYMS | 180 | IIDPSGGRTSFAQKFQG | 8 | ARYPESWPYGMDV | 184 | RASQSINSYLN | 16 | AASSLQS | 17 | QQSLLTPFT | 18 |
| ADI-30268 | GYTFGSYYMG | 181 | IIDPSGGRTSYARKFQG | 9 | ARTPSSWPYGMDV | 185 | RASQSINSYLN | 16 | AASSLQS | 17 | QQSLLTPFT | 18 |
| ADI-27243 | GGSISSSRYYWG | 186 | SIYYSGSTYYNPSLKS | 22 | DGLYHTPEYFQH | 188 | RASQSVSSYLA | 26 | DASNRAT | 27 | QQRFAFPYT | 28 |
| ADI-30302 | GGSIGSSQYYWG | 187 | SIYRSGGTYYNPSLKS | 23 | DGLYHTPEYFQH | 188 | RASQSVSSYLA | 26 | DASNRAT | 27 | QQRFAFPYT | 28 |
| ADI-30336 | GGSISSSRYYWG | 186 | SIYYSGSTYYNPSLKS | 22 | DGLYHTPEYFQH | 188 | RASQSVSSYLA | 26 | DASNRAT | 27 | QQRFAHPYT | 29 |
| ADI-27278 | GFTFSSYSMN | 189 | YISGSSSTIYYADSVKG | 34 | HRIADSPSRAFDI | 191 | KSSQSVLFSSNNKNYLA | 41 | WASTRES | 42 | QQSYFFPT | 43 |
| ADI-30293 | GFTFSSYSMN | 189 | YI-SSSGTINYADSVKG | 35 | HRIADSPSRAFDI | 191 | KSSQSVLFSSNNKNYLA | 41 | WASTRES | 42 | QQSYFFPT | 43 |
| ADI-30296 | GFTIGGYSMN | 190 | YI-SSSTIHYADSVKG | 36 | HRIGRSPSRAFDI | 192 | KSSQSVLFSSNNKNYLA | 41 | WASTRES | 42 | QQSYFFPT | 43 |
| ADI-27291 | GFTFSSYAMS | 193 | AISGSGGSTYYADSVKG | 48 | DPGTDSSGYYYIWRY | 196 | RASQSVSSNLA | 57 | SASTRAT | 58 | QQYVPHPPFT | 59 |
| ADI-30283 | GFTFSPYGMS | 194 | SISGSGGRTYYADSVKG | 49 | DPGTDSSGYYYIWRY | 196 | RASQSVSSNLA | 57 | SASTRAT | 58 | QQYVPHPPFT | 59 |
| ADI-30286 | GFTFGPYGMS | 195 | AISGSGASTWYADSVKG | 50 | DPGTHYSGYYYIWRY | 197 | RASQSVSSNLA | 57 | SASTRAT | 58 | QQYVPHPPFT | 59 |
| ADI-30288 | GFTFGPYGMS | 195 | AISGSGASTWHADSVKG | 51 | DPGTDSTGYYYIWRY | 198 | RASQSVSSNLA | 57 | SASTRAT | 58 | QQYVPHPPFT | 59 |
| ADI-27297 | GYTFTSYYMH | 199 | IINPSGGSTSYAQKFQG | 6 | DHDIAAAGRLADY | 201 | RASQGISSWLA | 69 | AASSLQS | 17 | QQAVILPIT | 70 |
| ADI-30272 | GYTFTEYYMH | 200 | IISPSAGSTSYAQKFQG | 63 | DHDIAAAGRLADY | 201 | RASQGISSWLA | 69 | AASSLQS | 17 | QQAVILPIT | 70 |
| ADI-30278 | GYTFTEYYMH | 200 | IISPSAGSTKYAQKFQG | 64 | DHDIRLAGRLADY | 202 | RASQGISSWLA | 69 | AASSLQS | 17 | QQAVILPIT | 70 |
| ADI-27301 | GGSISSSSYYWG | 203 | SIYYSGSTYYNPSLKS | 22 | EAGRGTTGLLFDY | 206 | RASQSISSWLA | 81 | KASSLES | 82 | QQYGILPRT | 83 |
| ADI-30306 | GGSISSSLYYWG | 204 | SIYYSGSTFYNPSFKS | 75 | EAGRGTTGLLFDY | 206 | RASQSISSWLA | 81 | KASSLES | 82 | QQYGILPRT | 83 |
| ADI-30311 | GGSIASSVYYWG | 205 | SIYYSGSTWYNPSLKS | 76 | EAGRTGTGLLFDY | 207 | RASQSISSWLA | 81 | KASSLES | 82 | QQYGILPRT | 83 |

TABLE 3

VH and VL sequences of variable regions of exemplary antibodies of the present invention VH sequences of exemplary antibodies

| Antibody | VH | SEQ ID NO: |
|---|---|---|
| ADI-27238 | QVQLVQSGAEVKKPGASVKVSCKASGYTFTSYYMSWVRQAPGQGLEWMGIINPSGGSTSYAQKFQGRVTMTRDTSTSTVYMELSSLRSEDTAVYYCARARYPSSWPYGMDVWGQGTTVTVSS | 84 |

TABLE 3-continued

| Antibody | | SEQ ID NO: |
|---|---|---|
| ADI-30263 | QVQLVQSGAEVKKPGASVKVSCKASGYTFLSYYMNWVRQAPGQGLEWMGIIDPSGGRTSYA QKFQGRVTMTRDTSTSTVYMELSSLRSEDTAVYYCARARYPSSWPYGTDVWGQGTTVTVSS | 85 |
| ADI-30267 | QVQLVQSGAEVKKPGASVKVSCKASGYTFRSYYMSWVRQAPGQGLEWMGIIDPSGGRTSFA QKFQGRVTMTRDTSTSTVYMELSSLRSEDTAVYYCARARYPESWPYGMDVWGQGTTVTVSS | 86 |
| ADI-30268 | QVQLVQSGAEVKKPGASVKVSCKASGYTFGSYYMGWVRQAPGQGLEWMGIIDPSGGRTSYA RKFQGRVTMTRDTSTSTVYMELSSLRSEDTAVYYCARARTPSSWPYGMDVWGQGTTVTVSS | 87 |
| ADI-27243 | QLQLQESGPGLVKPSETLSLTCTVSGGSISSSRYYWGWIRQPPGKGLEWIGSIYYSGSTYY NPSLKSRVTISVDTSKNQFSLKLSSVTAADTAVYYCARDGLYHTPEYFQHWGQGTLVTVSS | 88 |
| ADI-30302 | QLQLQESGPGLVKPSETLSLTCTVSGGSIGSSQYYWGWIRQPPGKGLEWIGSIYRSGGTYY NPSLKSRVTISVDTSKNQFSLKLSSVTAADTAVYYCARDGLYHTPEYFQHWGQGTLVTVSS | 89 |
| ADI-30336 | QLQLQESGPGLVKPSETLSLTCTVSGGSISSSRYYWGWIRQPPGKGLEWIGSIYYSGSTYY NPSLKSRVTISVDTSKNQFSLKLSSVTAADTAVYYCARDGLYHTPEYFQHWGQGTLVTVSS | 90 |
| ADI-27278 | EVQLVESGGGLVQPGGSLRLSCAASGFTFSSYSMNWVRQAPGKGLEWVSYISGSSSTIYYA DSVKGRFTISRDNAKNSLYLQMNSLRAEDTAVYYCARHRIADSPSRAFDIWGQGTMVTVSS | 91 |
| ADI-30293 | EVQLVESGGGLVQPGGSLRLSCAASGFTFSSYSMNWVRQAPGKGLEWVSYISSSGTINYAD SVKGRFTISRDNAKNSLYLQMNSLRAEDTAVYYCARHRIADSPSRAFDIWGQGTMVTVSS | 92 |
| ADI-30296 | EVQLVESGGGLVQPGGSLRLSCAASGFTIGGYSMNWVRQAPGKGLEWVSYISSSSTIHYAD SVKGRFTISRDNAKNSLYLQMNSLRAEDTAVYYCARHRIGRSPSRAFDIWGQGTMVTVSS | 93 |
| ADI-27291 | EVQLLESGGGLVQPGGSLRLSCAASGFTFSSYAMSWVRQAPGKGLEWVSAISGSGGSTYYAD SVKGRFTISRDNSKNTLYLQMNSLRAEDTAVYYCAKDPGTDSSGYYYIWRYWGQGTLVTVSS | 94 |
| ADI-30283 | EVQLLESGGGLVQPGGSLRLSCAASGFTFSPYGMSWVRQAPGKGLEWVSSISGSGGRTYYAD SVKGRFTISRDNSKNTLYLQMNSLRAEDTAVYYCAKDPGTDSSGYYYIWRYWGQGTLVTVSS | 95 |
| ADI-30286 | EVQLLESGGGLVQPGGSLRLSCAASGFTFGPYGMSWVRQAPGKGLEWVSAISGSGASTWYAD SVKGRFTISRDNSKNTLYLQMNSLRAEDTAVYYCAKDPGTHYSGYYYIWRYWGQGTLVTVSS | 96 |
| ADI-30288 | EVQLLESGGGLVQPGGSLRLSCAASGFTFGPYGMSWVRQAPGKGLEWVSAISGSGASTWHAD SVKGRFTISRDNSKNTLYLQMNSLRAEDTAVYYCAKDPGTDSTGYYYIWRYWGQGTLVTVSS | 97 |
| ADI-27297 | QVQLVQSGAEVKKPGASVKVSCKASGYTFTSYYMHWVRQAPGQGLEWMGIINPSGGSTSYAQ KFQGRVTMTRDTSTSTVYMELSSLRSEDTAVYYCARDHDIAAAGRLADYWGQGTLVTVSS | 98 |
| ADI-30272 | QVQLVQSGAEVKKPGASVKVSCKASGYTFTEYYMHWVRQAPGQGLEWMGIISPSAGSTSYAQ KFQGRVTMTRDTSTSTVYMELSSLRSEDTAVYYCARDHDIAAAGRLADYWGQGTLVTVSS | 99 |
| ADI-30278 | QVQLVQSGAEVKKPGASVKVSCKASGYTFTEYYMHWVRQAPGQGLEWMGIISPSAGSTKYAQ KFQGRVTMTRDTSTSTVYMELSSLRSEDTAVYYCARDHDIRLAGRLADYWGQGTLVTVSS | 100 |
| ADI-27301 | QLQLQESGPGLVKPSETLSLTCTVSGGSISSSSYYWGWIRQPPGKGLEWIGSIYYSGSTYYN PSLKSRVTISVDTSKNQFSLKLSSVTAADTAVYYCAREAGRGTTGLLFDYWGQGTLVTVSS | 101 |
| ADI-30306 | QLQLQESGPGLVKPSETLSLTCTVSGGSISSSLYYWGWIRQPPGKGLEWIGSIYYSGSTFYN PSFKSRVTISVDTSKNQFSLKLSSVTAADTAVYYCAREAGRGTTGLLFDYWGQGTLVTVSS | 102 |
| ADI-30311 | QLQLQESGPGLVKPSETLSLTCTVSGGSIASSVYYWGWIRQPPGKGLEWIGSIYYSGSTWYN PSLKSRVTISVDTSKNQFSLKLSSVTAADTAVYYCAREAGRTGTGLLFDYWGQGTLVTVSS | 103 |

| Antibody | VL sequences of exemplary antibodies<br>VL | SEQ ID NO: |
|---|---|---|
| ADI-27238 | DIQMTQSPSSLSASVGDRVTITCRASQSINSYLNWYQQKPGKAPKLLIYAASSLQSGVPSRF SGSGSGTDFTLTISSLQPEDFATYYCQQSLLTPFTFGGGTKVEIK | 104 |
| ADI-30263 | DIQMTQSPSSLSASVGDRVTITCRASQSINSYLNWYQQKPGKAPKLLIYAASSLQSGVPSRF SGSGSGTDFTLTISSLQPEDFATYYCQQSLLTPFTFGGGTKVEIK | 104 |
| ADI-30267 | DIQMTQSPSSLSASVGDRVTITCRASQSINSYLNWYQQKPGKAPKLLIYAASSLQSGVPSRF SGSGSGTDFTLTISSLQPEDFATYYCQQSLLTPFTFGGGTKVEIK | 104 |
| ADI-30268 | DIQMTQSPSSLSASVGDRVTITCRASQSINSYLNWYQQKPGKAPKLLIYAASSLQSGVPSRF SGSGSGTDFTLTISSLQPEDFATYYCQQSLLTPFTFGGGTKVEIK | 104 |
| ADI-27243 | EIVLTQSPATLSLSPGERATLSCRASQSVSSYLAWYQQKPGQAPRLLIYDASNRATGIPARF SGSGSGTDFTLTISSLEPEDFAVYYCQQRFAFPYTFGGGTKVEIK | 105 |
| ADI-30302 | EIVLTQSPATLSLSPGERATLSCRASQSVSSYLAWYQQKPGQAPRLLIYDASNRATGIPARF SGSGSGTDFTLTISSLEPEDFAVYYCQQRFAFPYTFGGGTKVEIK | 105 |

TABLE 3-continued

| | | |
|---|---|---|
| ADI-30336 | EIVLTQSPATLSLSPGERATLSCRASQSVSSYLAWYQQKPGQAPRLLIYDASNRATGIPARF SGSGSGTDFTLTISSLEPEDFAVYYCQQRFAHPYTFGGGTKVEIK | 106 |
| ADI-27278 | DIVMTQSPDSLAVSLGERATINCKSSQSVLFSSNNKNYLAWYQQKPGQPPKLLIYWASTRES GVPDRFSGSGSGTDFTLTISSLQAEDVAVYYCQQSYFFPTFGGGTKVEIK | 107 |
| ADI-30293 | DIVMTQSPDSLAVSLGERATINCKSSQSVLFSSNNKNYLAWYQQKPGQPPKLLIYWASTRES GVPDRFSGSGSGTDFTLTISSLQAEDVAVYYCQQSYFFPTFGGGTKVEIK | 107 |
| ADI-30296 | DIVMTQSPDSLAVSLGERATINCKSSQSVLFSSNNKNYLAWYQQKPGQPPKLLIYWASTRES GVPDRFSGSGSGTDFTLTISSLQAEDVAVYYCQQSYFFPTFGGGTKVEIK | 107 |
| ADI-27291 | EIVMTQSPATLSVSPGERATLSCRASQSVSSNLAWYQQKPGQAPRLLIYSASTRATGIPARF SGSGSGTEFTLTISSLQSEDFAVYYCQQYVPHPPFTFGGGTKVEIK | 108 |
| ADI-30283 | EIVMTQSPATLSVSPGERATLSCRASQSVSSNLAWYQQKPGQAPRLLIYSASTRATGIPARF SGSGSGTEFTLTISSLQSEDFAVYYCQQYVPHPPFTFGGGTKVEIK | 108 |
| ADI-30286 | EIVMTQSPATLSVSPGERATLSCRASQSVSSNLAWYQQKPGQAPRLLIYSASTRATGIPARF SGSGSGTEFTLTISSLQSEDFAVYYCQQYVPHPPFTFGGGTKVEIK | 108 |
| ADI-30288 | EIVMTQSPATLSVSPGERATLSCRASQSVSSNLAWYQQKPGQAPRLLIYSASTRATGIPARF SGSGSGTEFTLTISSLQSEDFAVYYCQQYVPHPPFTFGGGTKVEIK | 108 |
| ADI-27297 | DIQMTQSPSSVSASVGDRVTITCRASQGISSWLAWYQQKPGKAPKLLISAASSLQSGVPSRF SGSGSGTDFTLTISSLQPEDFATYYCQQAVILPITFGGGTKVEIK | 109 |
| ADI-30272 | DIQMTQSPSSVSASVGDRVTITCRASQGISSWLAWYQQKPGKAPKLLISAASSLQSGVPSRF SGSGSGTDFTLTISSLQPEDFATYYCQQAVILPITFGGGTKVEIK | 109 |
| ADI-30278 | DIQMTQSPSSVSASVGDRVTITCRASQGISSWLAWYQQKPGKAPKLLISAASSLQSGVPSRF SGSGSGTDFTLTISSLQPEDFATYYCQQAVILPITFGGGTKVEIK | 109 |
| ADI-27301 | DIQMTQSPSTLSASVGDRVTITCRASQSISSWLAWYQQKPGKAPKLLIYKASSLESGVPSRF SGSGSGTEFTLTISSLQPDDFATYYCQQYGILPRTFGGGTKVEIK | 110 |
| ADI-30306 | DIQMTQSPSTLSASVGDRVTITCRASQSISSWLAWYQQKPGKAPKLLIYKASSLESGVPSRF SGSGSGTEFTLTISSLQPDDFATYYCQQYGILPRTFGGGTKVEIK | 110 |
| ADI-30311 | DIQMTQSPSTLSASVGDRVTITCRASQSISSWLAWYQQKPGKAPKLLIYKASSLESGVPSRF SGSGSGTEFTLTISSLQPDDFATYYCQQYGILPRTFGGGTKVEIK | 110 |

TABLE 4

SEQ ID numbers of related sequences of all antibodies involved in the present invention

| Antibody | HCDR1 | HCDR2 | HCDR3 | VH | HC | VH DNA | LCDR1 | LCDR2 | LCDR3 | VL | LC | VL DNA |
|---|---|---|---|---|---|---|---|---|---|---|---|---|
| ADI-27238 | 1 | 6 | 11 | 84 | 111 | 150 | 16 | 17 | 18 | 104 | 137 | 170 |
| ADI-30263 | 2 | 7 | 12 | 85 | 112 | 151 | 16 | 17 | 18 | 104 | 137 | 170 |
| ADI-30267 | 3 | 8 | 13 | 86 | 113 | 152 | 16 | 17 | 18 | 104 | 137 | 170 |
| ADI-30268 | 4 | 9 | 14 | 87 | 114 | 153 | 16 | 17 | 18 | 104 | 137 | 170 |
| Consensus sequence | 5 | 10 | 15 | | | | | | | | | |
| ADI-27243 | 19 | 22 | 25 | 88 | 115 | 154 | 26 | 27 | 28 | 105 | 138 | 171 |
| ADI-30302 | 20 | 23 | 25 | 89 | 116 | 155 | 26 | 27 | 28 | 105 | 138 | 171 |
| ADI-30336 | 19 | 22 | 25 | 90 | 117 | 156 | 26 | 27 | 29 | 106 | 139 | 172 |
| Consensus sequence | 21 | 24 | 25 | | | | | | 30 | | | |
| ADI-27278 | 31 | 34 | 38 | 91 | 118 | 157 | 41 | 42 | 43 | 107 | 140 | 173 |
| ADI-30293 | 31 | 35 | 38 | 92 | 119 | 158 | 41 | 42 | 43 | 107 | 140 | 173 |
| ADI-30296 | 32 | 36 | 39 | 93 | 120 | 159 | 41 | 42 | 43 | 107 | 140 | 173 |
| Consensus sequence | 33 | 37 | 40 | | | | | | | | | |
| ADI-27291 | 44 | 48 | 53 | 94 | 121 | 160 | 57 | 58 | 59 | 108 | 141 | 174 |
| ADI-30283 | 45 | 49 | 53 | 95 | 122 | 161 | 57 | 58 | 59 | 108 | 141 | 174 |
| ADI-30286 | 46 | 50 | 54 | 96 | 123 | 162 | 57 | 58 | 59 | 108 | 141 | 174 |
| ADI-30288 | 46 | 51 | 55 | 97 | 124 | 163 | 57 | 58 | 59 | 108 | 141 | 174 |
| Consensus sequence | 47 | 52 | 56 | | | | | | | | | |
| ADI-27297 | 60 | 6 | 66 | 98 | 125 | 164 | 69 | 17 | 70 | 109 | 142 | 175 |
| ADI-30272 | 61 | 63 | 66 | 99 | 126 | 165 | 69 | 17 | 70 | 109 | 142 | 175 |
| ADI-30278 | 61 | 64 | 67 | 100 | 127 | 166 | 69 | 17 | 70 | 109 | 142 | 175 |
| Consensus sequence | 62 | 65 | 68 | | | | | | | | | |

TABLE 4-continued

SEQ ID numbers of related sequences of all antibodies involved in the present invention

| Antibody | HCDR1 | HCDR2 | HCDR3 | VH | HC | VH DNA | LCDR1 | LCDR2 | LCDR3 | VL | LC | VL DNA |
|---|---|---|---|---|---|---|---|---|---|---|---|---|
| ADI-27301 | 71 | 22 | 78 | 101 | 128 | 167 | 81 | 82 | 83 | 110 | 143 | 176 |
| ADI-30306 | 72 | 75 | 78 | 102 | 129 | 168 | 81 | 82 | 83 | 110 | 143 | 176 |
| ADI-30311 | 73 | 76 | 79 | 103 | 130 | 169 | 81 | 82 | 83 | 110 | 143 | 176 |
| Consensus sequence | 74 | 77 | 80 | | | | | | | | | |

Note:
HC was formed by fusing a VH sequence to a IgG4 PAA portion of SEQ ID NO: 177; and LC was formed by fusing a VL sequence to a Ck chain of SEQ ID NO: 209.

The 20 exemplary antibodies (ADI-27238, ADI-30263, ADI-30267, ADI-30268, ADI-27243, ADI-30302, ADI-30336, ADI-27278, ADI-30293, ADI-30296, ADI-27291, ADI-30283, ADI-30286, ADI-30288, ADI-27297, ADI-30272, ADI-30278, ADI-27301, ADI-30306, and ADI-30311) involved in the examples of the present invention described below, the amino acid sequences of the CDRs, the light and heavy chain variable regions, and the light and heavy chains of these antibodies, as well as the corresponding nucleotide sequences, are listed in Tables 1-3 and sequence listing of the present application. The corresponding sequence numbers are summarized in Table 4.

EXAMPLES

Example 1: Preparation of Antibodies

Screening for Anti-TIGIT Fully Humanized Antibodies by Yeast Display

Yeast-based antibody presentation libraries (Adimab) were amplified according to prior art (described in WO 2009036379, WO 2010105256, and WO 2012009568), with a diversity of $1\times10^9$ in each library. Briefly, the first two rounds of screening employed magnetic bead cell sorting using the MACS system available from Miltenyi. First, yeast cells (about $1\times10^{10}$ cells/library) from the libraries were incubated in FACS buffer (phosphate buffer, containing 0.1% bovine serum albumin and 100 nM biotin-labeled human TIGIT antigens (Acro Biosystems, TIT-H52H3)) for 15 min at room temperature. The cells were washed once with 50 mL of pre-cooled FACS buffer and resuspended with 40 mL of the same buffer, followed by addition of 500 µL of streptavidin microbeads (Miltenyi LS) and incubation at 4° C. for 15 min. The mixture was centrifuged at 1000 rpm for 5 min. After discarding the supernatant, the cells were resuspended with 5 mL of FACS buffer. The resulting cell suspension was loaded on a Miltenyi LS column. After loading, the column was washed three times, with 3 mL of FACS buffer each time. The Miltenyi LS column was removed from the magnetic field and eluted with 5 mL of growth medium. The eluted yeast cells were collected and incubated overnight at 37° C.

The next round of sorting was performed using a flow cytometer, wherein approximately $1\times10^8$ yeast cells screened by the MACS system were washed three times with FACS buffer and co-incubated with TIGIT antigens labeled by a low concentration of biotin (100-1 nM) at room temperature. The supernatant was discarded. The cells were washed twice with FACS buffer and mixed with LC-FITC (FITC-labeled anti-human immunoglobulin kappa light chain antibody, Southern Biotech) (1:100 dilution) and SA-633 (streptavidin-633, Molecular Probes) (1:500 dilution) or SA-PE (streptavidin-PE, Sigma) (1:50 dilution) reagents, and the mixture was incubated at 4° C. for 15 min. The cells were eluted twice with pre-cooled FACS buffer, resuspended in 0.4 mL of buffer and transferred into a separator tube with a filter. The cells were sorted using FACS ARIA (BD Biosciences).

The yeast cells expressing the anti-TIGIT antibody obtained by screening were induced by shaking at 30° C. for 48 h to express the anti-TIGIT antibody. After the induction, the yeast cells were removed by centrifugation at 1300 rpm for 10 min, and the supernatant was collected. The anti-TIGIT antibodies in the supernatant were purified using Protein A and eluted using acetic acid buffer at pH 2.0 prior to harvest. The purity of the antibodies was more than 95%. The antibodies were digested by papin and purified by KappaSelect (GE Healthcare) to produce the corresponding Fab fragments. The anti-TIGIT antibodies (ADI-27301, ADI-27238, ADI-27278, ADI-27243, ADI-27297, and ADI-27291) were obtained from this screening.

Affinity Optimization for Anti-Human TIGIT Antibodies

To obtain anti-human TIGIT antibodies with higher affinity, antibodies (ADI-27301, ADI-27238, ADI-27278, ADI-27243, ADI-27297, and ADI-27291) were optimized by the following methods.

VHmut Screening

This method was to introduce mutations into antibody heavy chain regions by conventional mismatch PCR. In the PCR process, the probability of base pair mismatch raised to about 0.01 bp by adding 1 µM highly mutated base analogs dPTP and 8-oxo-dGTP.

The resulting mismatch PCR products were constructed into a vector containing the heavy chain constant region by homologous recombination. By this method, a secondary library with the capacity of $1\times10^7$ was obtained under screening pressure including TIGIT antigen titers, unlabeled antigen competition, and competition with the parent antibodies. Three rounds of screening were successfully performed by FACS.

CDRH1/CDRH2 Screening

CDRH3 genes of progeny antibodies obtained by VHmut were constructed into a CDRH1/CDRH2 gene pool with the diversity of $1\times10^8$, and 3 rounds of screening were carried out for the genes. The first round of screening adopted MACS, while the second and third rounds adopted FACS. Antibody-antigen conjugates were subjected to pressurized screening for screening out antibodies with the highest affinity.

Through the above affinity maturation process of 6 parent antibodies, 14 anti-human TIGIT monoclonal antibodies ADI-30263/ADI-30267/ADI-30268 (ADI-27238 progeny), ADI-30302/ADI-30336 (ADI-27243 progeny), ADI-30293/ADI-30296 (ADI-27278 progeny), ADI-30283/ADI-30286/ADI-30288 (ADI-27291 progeny), ADI-30272/ADI-30278 (ADI-27297 progeny), and ADI-30306/ADI-30311 (ADI-27301 progeny) with improved affinity were obtained.

The yeast cells expressing the anti-TIGIT antibody obtained by screening were induced by shaking at 30° C. for 48 h to express the anti-TIGIT antibody. After the induction, the yeast cells were removed by centrifugation at 1300 rpm for 10 min, and the supernatant was collected. The anti-TIGIT antibodies in the supernatant were purified using Protein A and eluted using acetic acid buffer at pH 2.0 prior to harvest. The purity of the antibodies was more than 95%. The antibodies were digested by papin and purified by KappaSelect (GE Healthcare) to produce the corresponding Fab fragments.

Expression and Purification of Antibodies

The sequence information and numbers of the anti-human TIGIT antibodies involved in the present invention are shown in Tables 1-9, wherein the parent antibodies and the affinity-matured progeny antibodies were all expressed and purified by yeasts with the method described above.

The following reference antibodies used in examples were expressed and purified in HEK293 cells: 22G2 is an anti-human TIGIT antibody from BMS that was transiently expressed in HEK293 cells, with the light and heavy chain variable region sequences identical to those of antibody "22G2" in Patent Application No. WO 2016/106302A1; 31C6 is an anti-human TIGIT antibody from Merck that was transiently expressed in HEK293 cells, with the light and heavy chain variable region sequences identical to those of antibody "31C6" in Patent Application No. WO 2016/028656A1; both 10A7 and 1F4 were anti-human TIGIT antibodies from Genentech that were transiently expressed in HEK293 cells, with light and heavy chain variable region sequences identical to those of antibodies "10A7" and "1F4" in Patent Application No. WO2015009856A2, respectively. The constant regions of the 4 reference antibodies all adopted wild-type IgG4 sequences.

For a transient expression of an antibody in HEK293 cells, the vector pTT5 was used. The heavy and light chains of the antibody were first cloned into separate pTT5 vectors. The pTT5 vectors carrying the heavy and light chains of the antibody molecule were transferred into the HEK293 cells by a chemical transfection method. The cultivated HEK293 cells were transiently transfected using a chemical transfection reagent PEI (purchased from Polysciences) according to a scheme provided by the manufacturer. Plasmid DNAs and transfection reagent were prepared in a laminar flow hood, and then F17 medium (Gibco) (the volume was ⅕ of transfection volume) was aliquoted into two 50-mL centrifuge tubes. The filtered plasmids (130 µg/100 mL) were added to one tube, and the filtered PEI (1 g/L, Polysciences) (mass ratio (plasmid:PEI)=1:3) was added to another. The two mixtures were each mixed well for 5 min, and then the two were mixed well and gently together for 20 times, followed by letting stand for 15-30 min (no more than 30 min). The DNA/PEI mixture was gently poured into the HEK293 cells and mixed well. The cells were cultivated at 37° C., 8% $CO_2$ for 7 days, with fresh medium fed every 48 h. Seven days later, or when the cells were continuously cultivated to cell viability was <60%, the mixture was centrifuged at 13000 rpm for 20 min. The supernatant was taken and purified with Protein A to achieve an antibody purity of greater than 95%.

Furthermore, the intact antibodies (ADI-30268, ADI-30278, ADI-30286, ADI-30288, ADI-30293, ADI-30306, and ADI-30336) were expressed and purified in CHO cells.

Expression and purification in CHO cells: CHO cell lines expressing the antibodies were produced using HD-BIOP1 (GS Null CHO-K1) from Horizon according to the manufacturer's instructions. The DNA sequences of the heavy and light chains of the antibody molecule were first inserted into pD2531 plasmids from ATUM. The constructed plasmids were then transferred into CHO cell lines by electrotransfection, and the antibody production was detected by ForteBio to determine the transfection efficiency after transfection for 24 h. The transfected cells were subjected to pressurized screening to obtain a cell pool of highly-expressed antibodies. The cell pool was then amplified to express large quantities of antibodies. The cell supernatant was collected and purified by Protein A and gel filtration to achieve an antibody purity of more than 95%.

Example 2. Affinity Assay of Antibodies

The equilibrium dissociation constant ($K_D$) for binding of the above 20 exemplary antibodies of the present invention to human TIGIT was measured by biological optical interferometry (ForteBio).

An ForteBio affinity assay was performed according to the prior art (Estep, P, et al., High throughput solution based measurement of antibody-antigen affinity and epitope binning MAbs, 2013.5(2): p. 270-8).

Measurement of monovalent affinity of the candidate antibody Fab to TIGIT-FC: a sensor was equilibrated off-line in an assay buffer for 20 min, followed by detecting online for 120 s to establish a baseline. Human TIGIT-FC was loaded on an AHQ sensor (ForteBio) for ForteBio affinity assay. The sensor with the loaded antigens was exposed to a solution containing 100 nM Fab until to a plateau, and then transferred to an assay buffer for dissociation for at least 2 min to measure the dissociation rate. Kinetic analysis was performed using a 1:1 binding model.

Measurement of monovalent affinity of intact candidate antibodies to human (ACRO, TIT-H52H3), mouse (ACRO, TIT-M52E6), and monkey TIGIT-his (ACRO, TIT-05223): the sensor was equilibrated off-line in an assay buffer for 20 min, followed by detecting online for 120 s to establish a baseline. The purified antibodies were loaded on an AHQ sensor (ForteBio) to a thickness of 1 nanometer for ForteBio affinity assay. The sensor with loaded antibodies was exposed to 100 nM TIGIT-his antigens until to a plateau, and then transferred to an assay buffer for dissociation for at least 2 min to measure the dissociation rate. Kinetic analysis was performed using a 1:1 binding model.

In experiments performed as described in the above assays, the $K_D$ values of 20 yeast-expressed candidate antibodies (Fab) are shown in Table 5.

TABLE 5

Monovalent $K_D$ values of 20 yeast-expressed candidate antibodies (Fab) to human TIGIT-FC

| Parent | Progeny | | |
|---|---|---|---|
| ADI-27238 | ADI-30263 | ADI-30267 | ADI-30268 |
| 1.38E−08 | 7.95E−10 | 1.66E−09 | 5.71E−10 |
| ADI-27243 | ADI-30302 | ADI-30336 | |
| 9.47E−09 | 3.29E−10 | 5.66E−10 | |
| ADI-27278 | ADI-30293 | ADI-30296 | |
| 1.09E−08 | 3.49E−09 | 2.43E−09 | |
| ADI-27291 | ADI-30283 | ADI-30286 | ADI-30288 |
| 6.48E−09 | 5.53E−10 | 4.36E−10 | 5.47E−10 |
| ADI-27297 | ADI-30272 | ADI-30278 | |
| 3.21E−08 | 1.19E−09 | 2.43E−10 | |
| ADI-27301 | ADI-30306 | ADI-30311 | |
| 8.01E−09 | 7.29E−10 | 8.07E−10 | |

In experiments performed as described in the above assays, the monovalent $K_D$ values of 7 intact candidate antibodies expressed by CHO cells to human, mouse and monkey TIGIT are shown in Table 6.

TABLE 6

Monovalent $K_D$ values of 7 candidate antibodies expressed by CHO cells and reference antibodies to human, mouse and monkey TIGIT

| No. | KD (human) | KD (monkey) | KD (mouse) |
|---|---|---|---|
| ADI-30268 | 3.29E−09 | 6.23E−08 | 4.64E−08 |
| ADI-30278 | 1.75E−09 | 4.53E−09 | N.B. |
| ADI-30286 | 1.76E−09 | 1.06E−08 | 1.34E−07 |
| ADI-30288 | 1.31E−09 | 7.19E−09 | 5.70E−09 |

TABLE 6-continued

Monovalent $K_D$ values of 7 candidate antibodies expressed by CHO cells and reference antibodies to human, mouse and monkey TIGIT

| No. | KD (human) | KD (monkey) | KD (mouse) |
|---|---|---|---|
| ADI-30293 | 7.89E−10 | 3.49E−08 | 1.30E−08 |
| ADI-30306 | 2.70E−09 | 3.44E−09 | N.B. |
| ADI-30336 | 1.46E−09 | 5.56E−10 | N.B. |
| 22G2(BMS) | 3.50E−09 | 4.20E−09 | N.B. |
| 31C6(MSD) | 2.34E−09 | 4.72E−10 | N.B. |

It can be seen from the above Tables that: (1) after affinity maturation, each progeny antibody has significantly improved affinity to human TIGIT compared with its parent antibody; (2) after affinity maturation, the affinity of the selected 7 antibodies expressed by CHO cells to human TIGIT was similar to or higher than that of the reference antibodies; all of the 7 candidate antibodies can cross-react with monkey TIGIT; and 4 (ADI-30268/ADI-30286/ADI-30288/ADI-30293) of the 7 candidate antibodies can cross-react with mice.

Example 3. Binding of Anti-TIGIT Antibodies to Human TIGIT Expressed on Cells The binding ability of the above 20 exemplary antibodies of the present invention to human TIGIT expressed on the surface of CHO cells was measured in a flow cytometry-based assay. The binding ability of the different antibodies was determined by comparing the binding curves thereof to human TIGIT expressed on the surface of CHO cells.

Specifically, after affinity maturation, yeasts were used to express both parent and progeny antibodies. After harvest (with the antibody purity of about 70%), the binding experiments of these antibodies to human TIGIT expressed on the surface of CHO cells were performed. The specific experimental process was as follows: (1) CHOS cells were transfected with human TIGIT plasmids constructed in pCHO1.0, and then screened for a stable cell pool using methotrexate and puromycin. (2) Candidate antibodies at different concentrations were incubated with the stable cell pool at 4° C. for 30 min. After three washes with PBS, the cells were incubated with PE-labeled mouse anti-human secondary antibodies for 30 min at 4° C. After three more washes with PBS, the cells were resuspended with 100 μL of PBS. (3) Flow cytometry was used to determine median fluorescence values in two channels for the cells. The $EC_{50}$ and the peak values of the curves were compared by plotting the base-10 logs of the antibody concentrations on the abscissa and the median fluorescence values in two channels on the ordinate. The results are shown in the following table and in FIG. 1 ($EC_{50}$: nM).

TIGIT expressed on the surface of CHO cells compared to its parent antibody (as indicated by a higher plateau in the binding curve); (2) The binding ability of the affinity matured progeny antibodies to human TIGIT expressed on the surface of CHO cells is superior than that of the two molecules 10A7 and 1F4 from Genetech, and is comparable to that of the molecule 22G2 from BMS and the molecule 31C6 from Merck.

Figure 2:
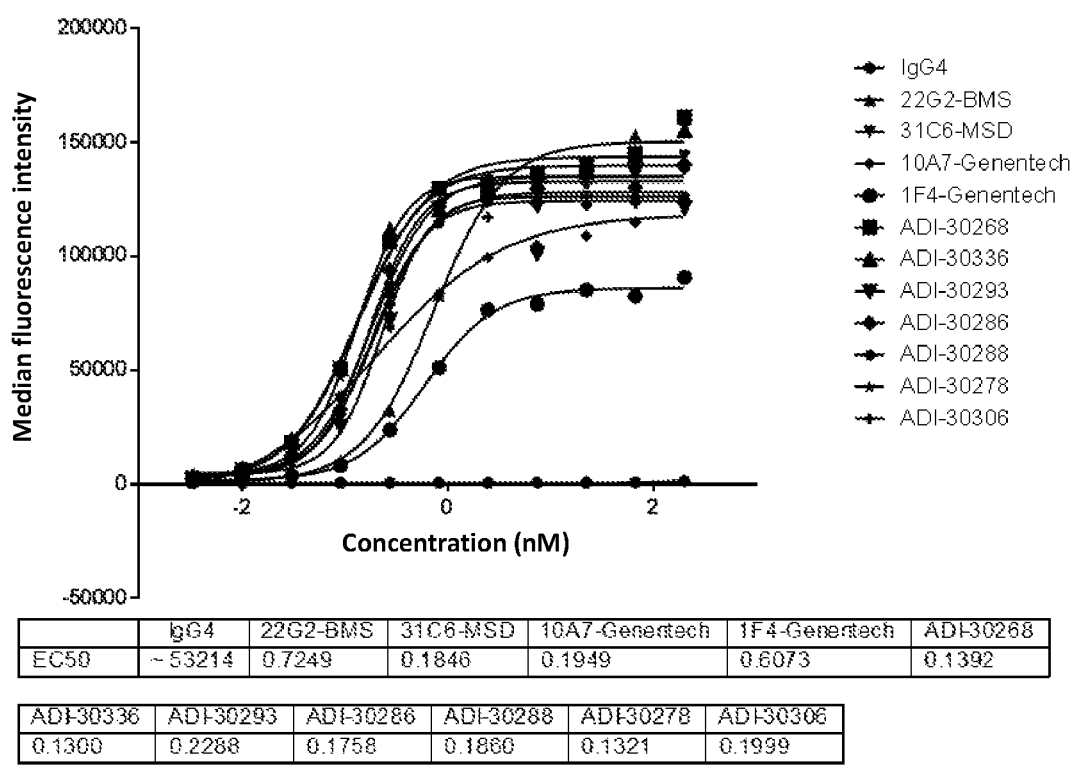
FIG. 2 shows the binding of 7 candidate antibodies expressed by CHO cells to human TIGIT expressed on the surface of CHO cells.
Figure 3A:
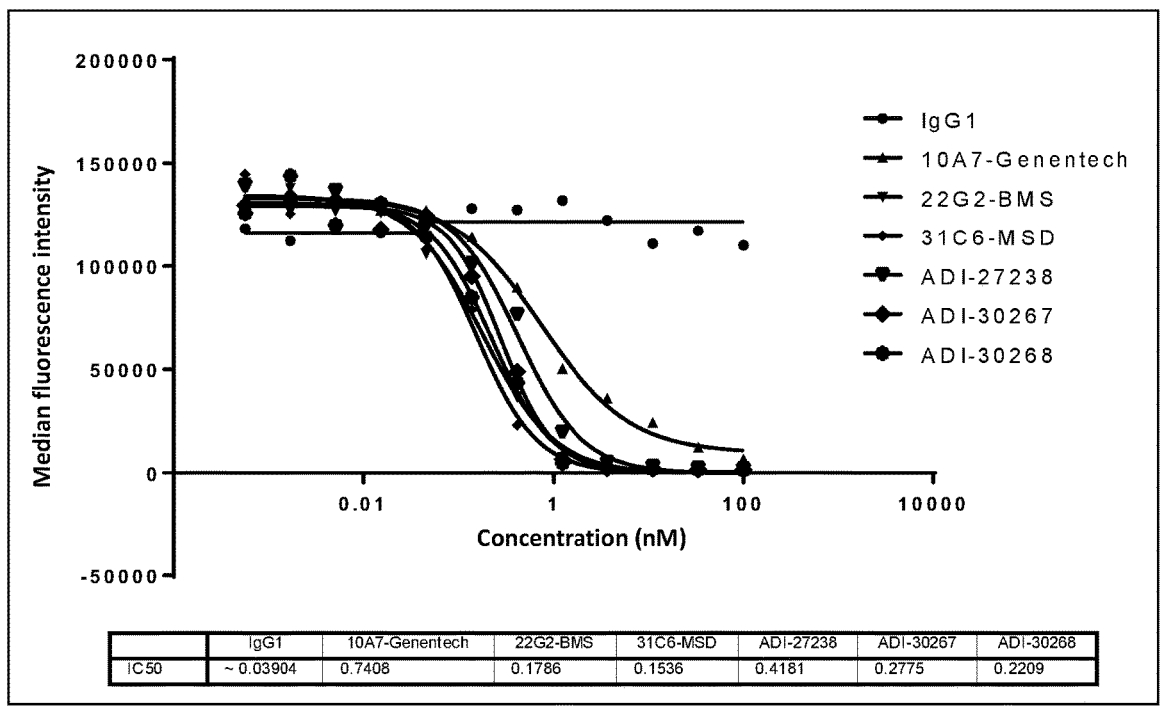
FIGS. 3A-F show the blocking ability of antibodies expressed by yeasts to CD155 before and after affinity maturation.
Figure 3B:
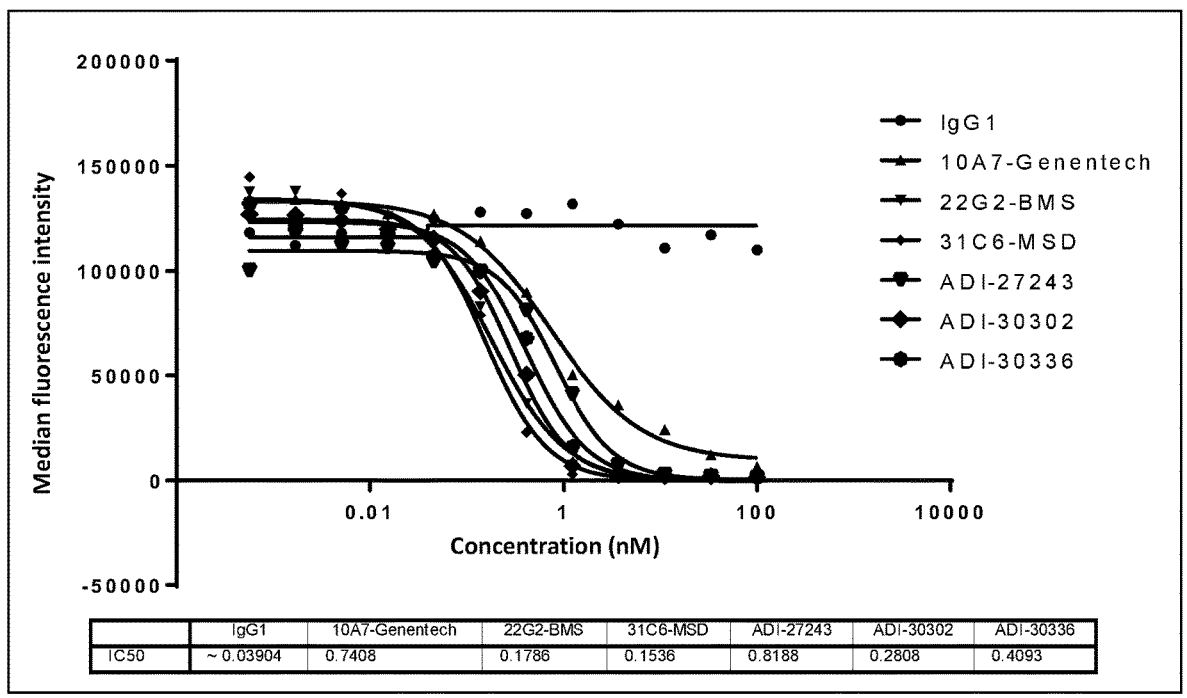
Figure 3C:
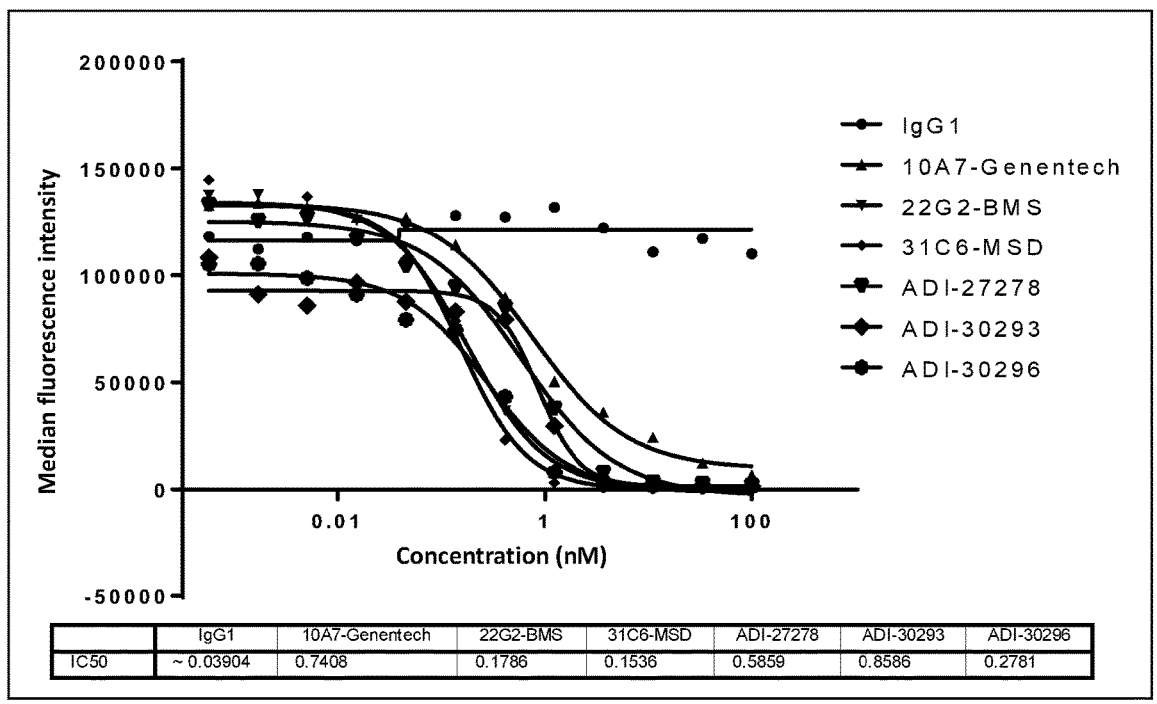
Figure 3D:
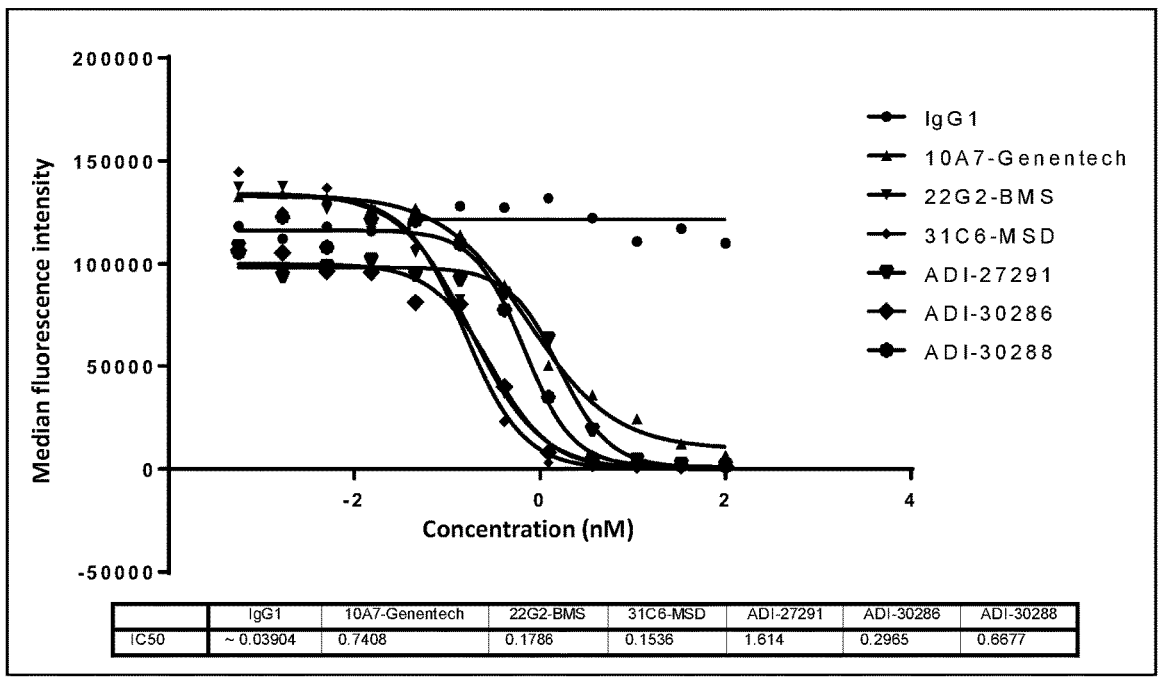
Figure 3E:
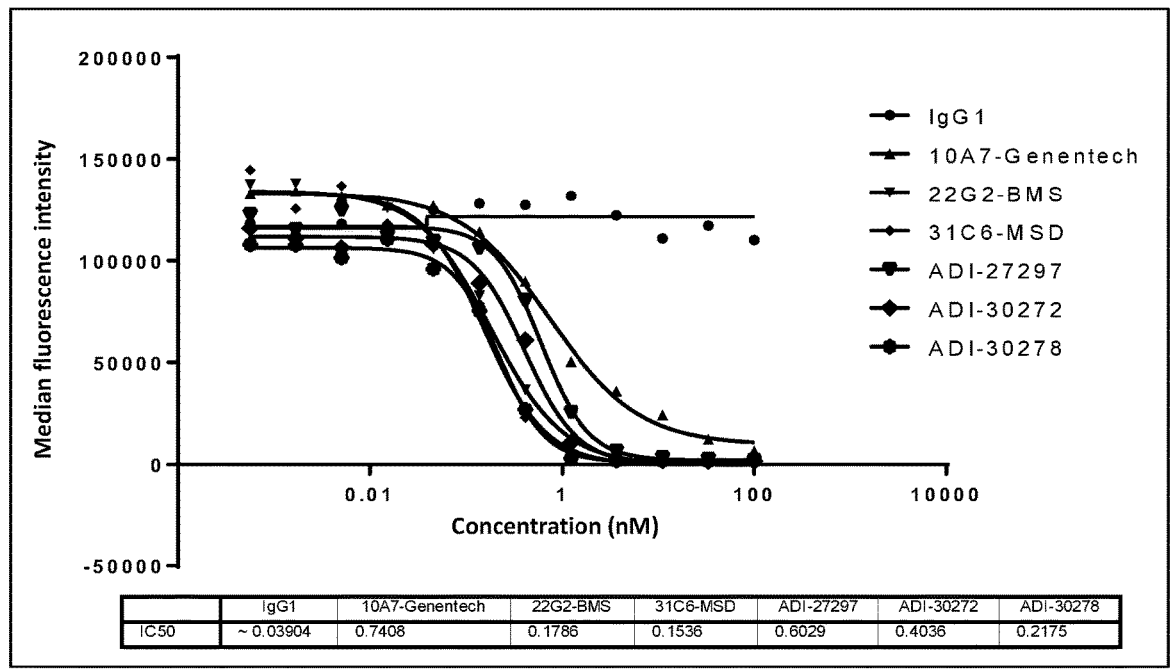
Figure 3F:
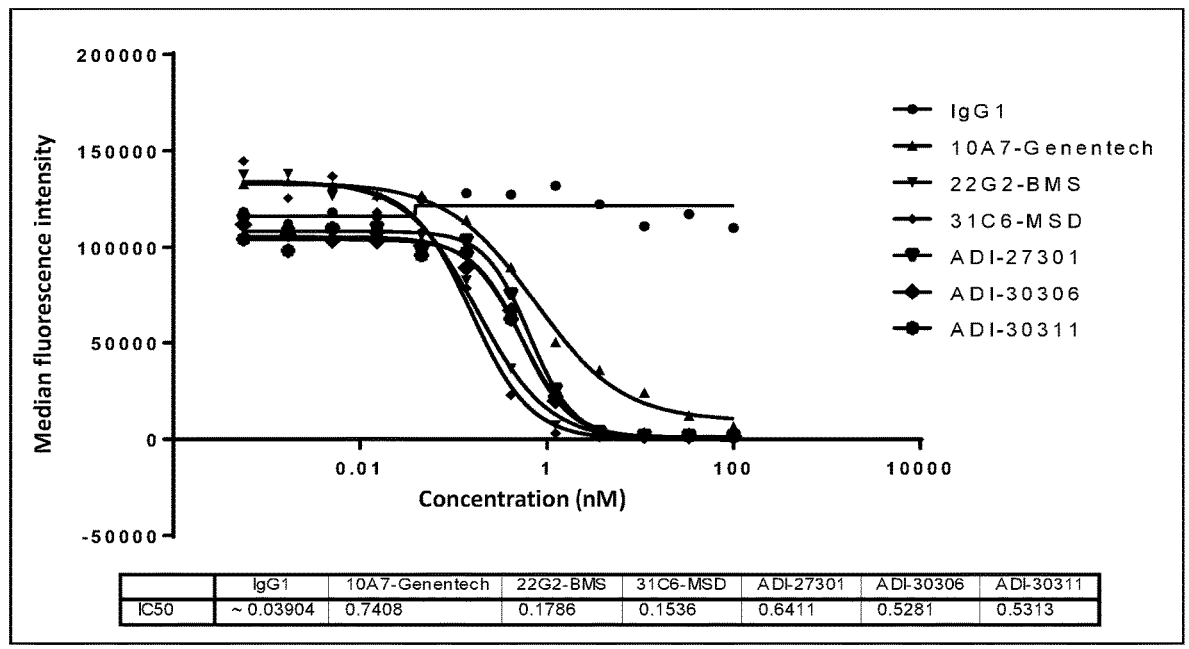

Furthermore, after affinity maturation, the selected 7 molecules were expressed and purified using a CHO system to obtain antibodies with high purity. The binding experiment of the antibodies with high purity to human TIGIT expressed on the surface of CHO cells was performed. In experiments performed as described in the above assays, ADI-30268, ADI-30336, ADI-30293, ADI-30286, ADI-30288, ADI-30278, and ADI-30306 bind to human TIGIT overexpressed on CHO cells with $EC_{50}$ values of 0.1392 nM, 0.1300 nM, 0.2288 nM, 0.1758 nM, 0.1860 nM, 0.1321 nM and 0.1999 nM, respectively, and the binding ability thereof is superior to that of reference antibodies 22G2 and 1F4 ($EC_{50}$ values of 0.7249 nM and 0.6073 nM, respectively) to human TIGIT overexpressed on CHO cells, and similar to that (an $EC_{50}$ value of 0.1846 nM) of reference antibody 31C6 to human TIGIT overexpressed on CHO cells. Although the reference antibody 10A7 has an $EC_{50}$ value (0.1949 nM) similar to that of the 7 candidate antibodies, it can be revealed from the binding curve of this antibody that the plateau of the curve thereof is lower than that of the 7 candidate antibodies. This is generally believed to be attributed to its faster dissociation characteristics (see FIG. 2). Therefore, the binding ability of 7 candidate antibodies to human TIGIT expressed on the surface of CHO cells is considered to be superior to that of 10A7.

Example 4. Blocking of Anti-TIGIT Antibody to its Ligand CD155

The ability of the candidate antibodies to block the ligands was determined by flow cytometry. The method is specifically as follows: a CHOS cell pool stably overexpressing human TIGIT was constructed, and 50 nM human CD155 protein (ACRO, TIT-H5253-1MG) with a mouse IgG2aFC fragment and antibodies at different concentrations were incubated with the cells for 30 min at 4° C. After three washes with PBS, ligands CD155 remaining on the cells were strained using goat anti-mouse FC (at a concentration of 1%) and secondary antibodies labeled with APC fluorescein (Biolegend, 405308). After three more washes with PBS, the median fluorescence values in a corresponding channel (C6, channel 4) were measured by a flow cytometer. The base-10 logs of the antibody concentrations (nM) were plotted on the abscissa and the median fluorescence value corresponding to each antibody concentration

| Antibody | IgG1 | 10A7 | 1F4 | 22G2 | 31C6 | |
|---|---|---|---|---|---|---|
| EC50 | ~1.388e+007 | 0.2690 | 0.7096 | 0.5106 | 0.4358 | |
| Antibody | ADI-27238 | ADI-30267 | ADI-30268 | ADI-27243 | ADI-30302 | ADI-30336 |
| EC50 | 0.7512 | 0.7402 | 0.3293 | 0.5873 | 0.3262 | 0.6291 |
| Antibody | ADI-27278 | ADI-30293 | ADI-30296 | ADI-27291 | ADI-30286 | ADI-30288 |
| EC50 | 0.9682 | 0.9003 | 0.3714 | 0.8522 | 0.4459 | 0.4755 |
| Antibody | ADI-27297 | ADI-30272 | ADI-30278 | ADI-27301 | ADI-30306 | ADI-30311 |
| EC50 | 0.4958 | 0.6098 | 0.4086 | 0.8990 | 0.7634 | 0.7566 |

From the above experimental results, the following conclusions can be drawn: (1) after affinity maturation, each progeny antibody has enhanced binding ability to human point was plotted on the ordinate. The blocking ability of different antibodies to CD155 was distinguished by analyzing the $IC_{50}$ values of the curves.

IgG1 was used as a negative control, and 10A7, 22G2, and 31C6 were used as positive controls to test the blocking ability of candidate molecules to CD155 before and after affinity maturation. FIG. 3 and the following table show the blocking ability of yeast-expressed antibodies to CD155 ($IC_{50}$: nM) before and after affinity maturation.

| Antibody | IgG1 | 10A7 | 22G2 | 31C6 | | |
|---|---|---|---|---|---|---|
| IC50 | ~0.03904 | 0.7408 | 0.1786 | 0.1536 | | |
| Antibody | ADI-27238 | ADI-30267 | ADI-30268 | ADI-27243 | ADI-30302 | ADI-30336 |
| IC50 | 0.4181 | 0.2775 | 0.2209 | 0.8188 | 0.2808 | 0.4093 |
| Antibody | ADI-27278 | ADI-30293 | ADI-30296 | ADI-27291 | ADI-30286 | ADI-30288 |
| IC50 | 0.5859 | 0.8586 | 0.2781 | 1.614 | 0.2965 | 0.6677 |
| Antibody | ADI-27297 | ADI-30272 | ADI-30278 | ADI-27301 | ADI-30306 | ADI-30311 |
| IC50 | 0.6029 | 0.4036 | 0.2175 | 0.6411 | 0.5281 | 0.5313 |

It can be concluded from the experimental results that most of the affinity matured progeny antibodies have improved blocking abilities to CD155 as compared to parent antibodies thereof, similar to the blocking abilities of reference antibodies 22G2 and 31C6 and stronger than that of reference antibody 10A7.

Figure 4:
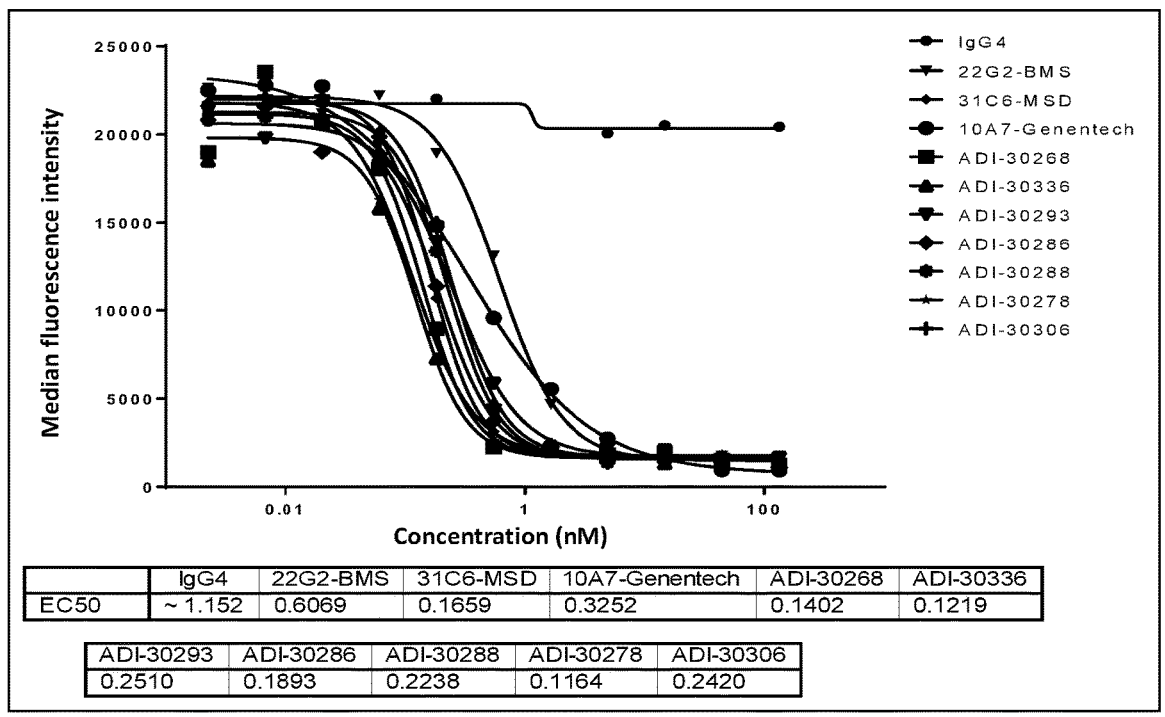
FIG. 4 shows the blocking ability of 7 candidate antibodies expressed by CHO cells to CD155.
Figure 5A:
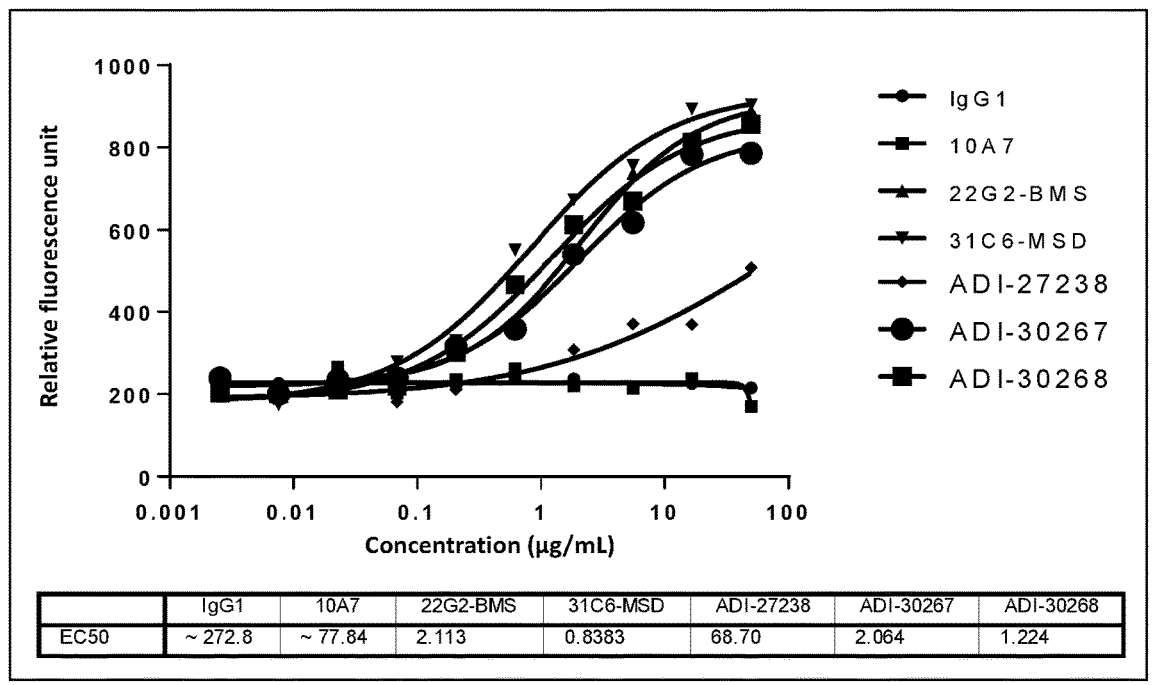
FIGS. 5A-E show MOA biological activity assays for antibodies expressed by yeasts before and after affinity maturation.
Figure 5B:
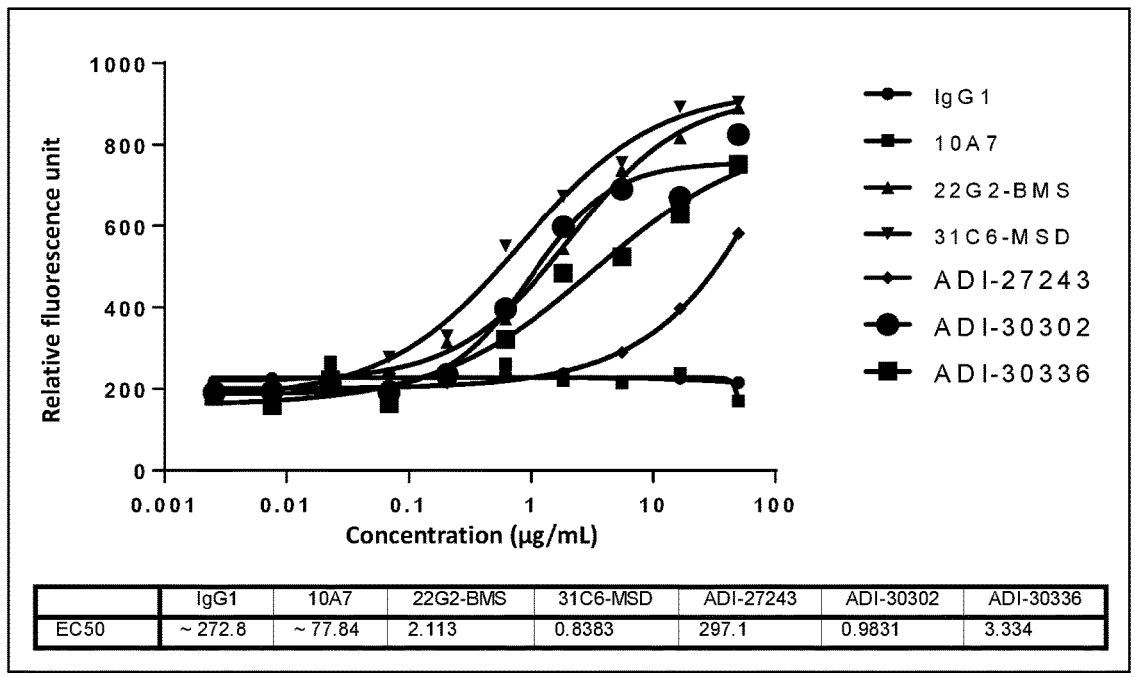
Figure 5C:
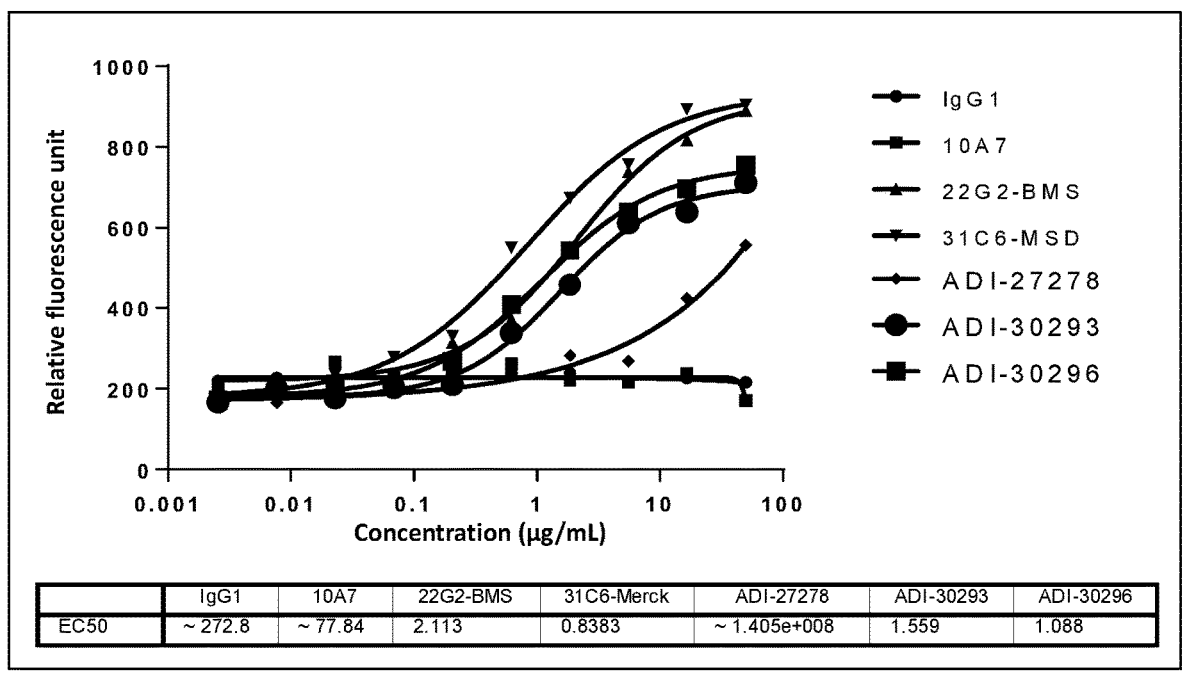
Figure 5D:
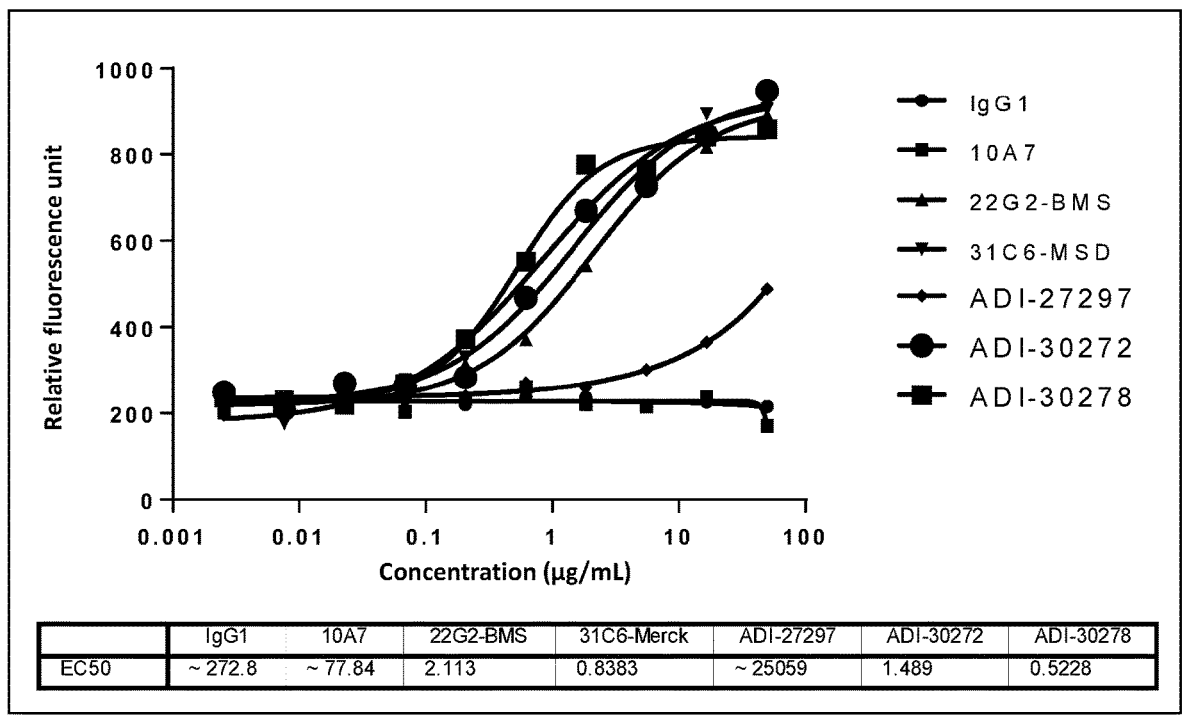
Figure 5E:
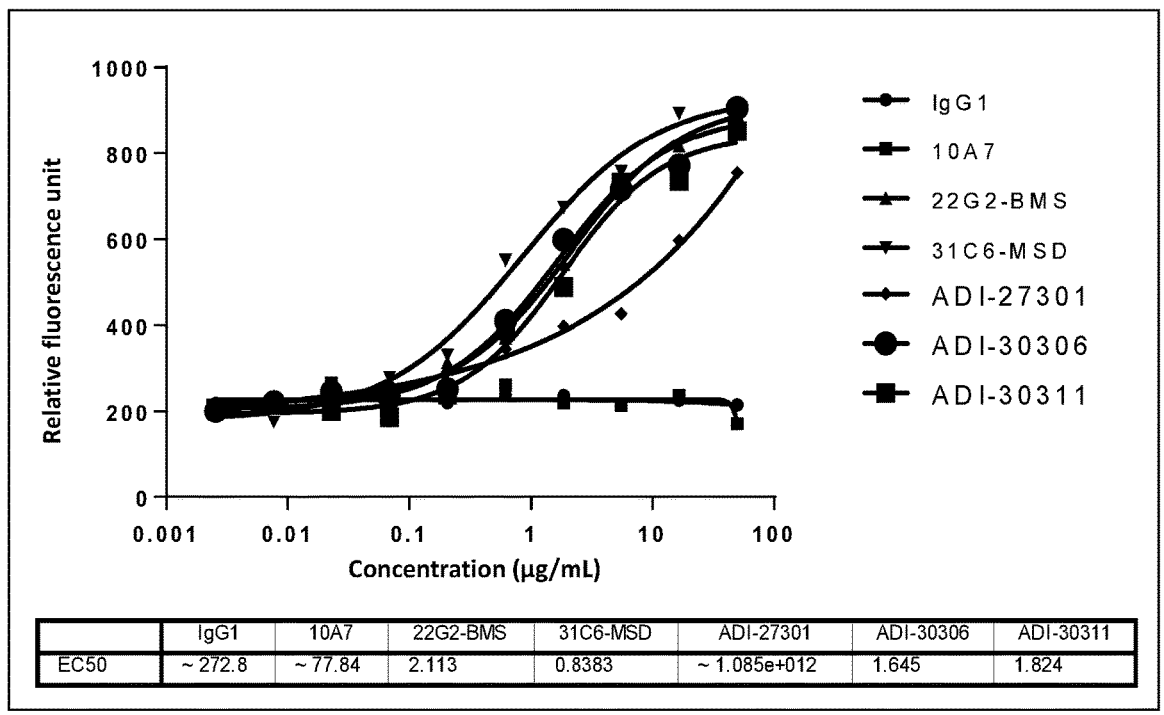

7 high-purity antibodies expressed by CHO cells were adopted for blocking the binding of CD155 to TIGIT. In the experiments performed as described in the above assays, IgG4 was used as a negative control, and 22G2, 31C6, and 10A7 were used as positive controls. It can be concluded from the experimental results that $IC_{50}$ of antibodies ADI-30268, ADI-30336, and ADI-30278 are 0.1402 nM, 0.1219 nM and 0.1164 nM, respectively, which are lower than those of reference antibodies 22G2 (0.6069 nM), 31C6 (0.1659 nM) and 10A7 (0.3252 nM), indicating that the three antibodies have stronger ligand (CD155) blocking ability than the reference antibodies; the other 4 candidate antibodies (ADI-30293, ADI-30286, ADI-30288, and ADI-30306) have $IC_{50}$ of 0.2510 nM, 0.1893 nM, 0.2238 nM, and 0.2420 nM, respectively, which are all lower than those of reference antibodies 22G2 and 10A7 but greater than that of reference antibody 31C6, indicating that these four antibodies have stronger ligand (CD155) blocking ability than reference antibodies 22G2 and 10A7 but weaker ligand (CD155) blocking ability than 31C6. The results are shown in the following table and in FIG. 4 ($IC_{50}$: nM).

| Antibody | IgG1 | 22G2 | 31C6 | 10A7 |
|---|---|---|---|---|
| IC50 | ~1.152 | 0.6069 | 0.1659 | 0.3252 |
| Antibody | ADI-30268 | ADI-30336 | ADI-30293 | ADI-30286 |
| IC50 | 0.1402 | 0.1219 | 0.2510 | 0.1893 |
| Antibody | ADI-30288 | ADI-30278 | ADI-30306 | |
| IC50 | 0.2238 | 0.1164 | 0.2420 | |

Example 5. MOA-Based Biological Activity Assay of Candidate Antibodies

Anti-TIGIT antibodies can relieve the inhibitory effect of CD155 on the downstream IL2 signaling pathway by blocking the binding of TIGIT to CD155. In this example, MOA-based assay cell lines (J2201) provided by Promega were used to detect the expression of fluorescent reporter genes and reflect the activation of IL2 signaling, thereby detecting the inhibitory effect of the antibodies on binding of TIGIT to CD155. The assay was performed in accordance with standard methods of Promega. The procedures were as follows: Jurkat cells stably expressing human TIGIT and luciferase reporter genes under the control of IL2 promoters, CHO-K1 cells stably expressing human CD155 and T cell activating elements, and anti-human TIGIT antibodies with different concentration gradients were co-incubated in a carbon dioxide incubator at 37° C. for 6 h, and then fluorescence signals were detected.

The experimental results showed that the affinity-matured progeny molecules (directly expressed by yeast, with the purity of about 70%) have significantly improved in vitro biological activity as compared to their parent molecules, and mostly reached the level similar to the two reference antibodies 22G2 and 31C6. The results are shown in the following table and in FIG. 5 ($EC_{50}$: nM).

| Antibody | IgG1 | 10A7 | 22G2 | 31C6 |
|---|---|---|---|---|
| EC50 | ~272.8 | ~77.84 | 2.113 | 0.8383 |
| Antibody | ADI-27238 | ADI-30267 | ADI-30268 | |
| EC50 | 68.70 | 2.064 | 1.224 | |
| Antibody | ADI-27243 | ADI-30302 | ADI-30336 | |
| EC50 | 297.1 | 0.9831 | 3.334 | |
| Antibody | ADI-27278 | ADI-30293 | ADI-30296 | |
| EC50 | ~1.405e+008 | 1.559 | 1.088 | |
| Antibody | ADI-27297 | ADI-30272 | ADI-30278 | |
| EC50 | ~25059 | 1.489 | 0.5228 | |
| Antibody | ADI-27301 | ADI-30306 | ADI-30311 | |
| EC50 | ~1.085e+012 | 1.645 | 1.824 | |

Figure 6:
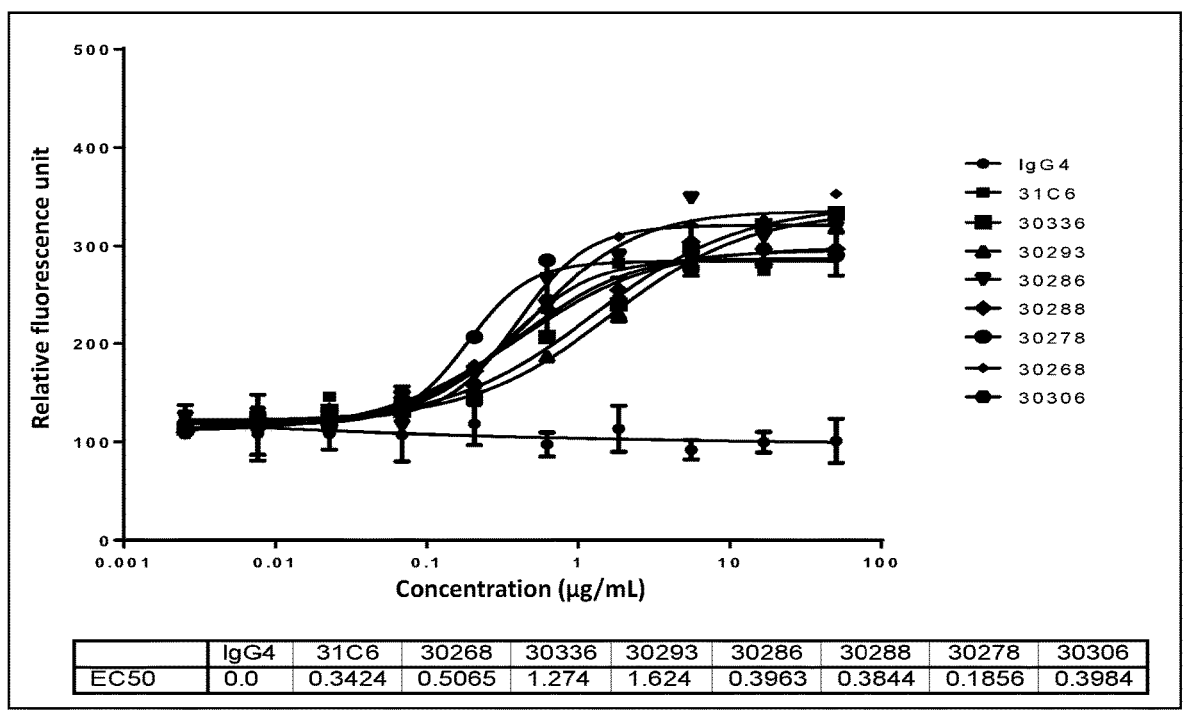
FIG. 6 shows MOA biological activity assays of 7 candidate antibodies expressed by CHO cells.

MOA-based biological activity assay were performed using 7 high-purity antibodies expressed by CHO cells. In the assay described above, IgG4 were used as negative controls, and 31C6 were used as positive controls. It can be concluded from the experimental results that the candidate antibody ADI-30278 have an $EC_{50}$ of 0.1856 nM in the experiments, which was lower than those of other candidate antibodies and the reference antibody 31C6 (0.3424 nM), showing stronger in vitro biological activity; antibodies ADI-30268, ADI-30286, ADI-30288, and ADI-30306 have $EC_{50}$ of 0.5065 nM, 0.3963 nM, 0.3844 nM, and 0.3984 nM, respectively, showing similar biological activity to reference antibody 31C6; and antibodies ADI-30336 and ADI-30293 have $EC_{50}$ of 1.274 nM and 1.624 nM, respectively, showing weaker biological activity. The results are shown in the following table and in FIG. 6 ($EC_{50}$: nM).

| Antibody | IgG4 | 31C6 | ADI-30268 |
|---|---|---|---|
| EC50 | 0.0 | 0.3424 | 0.5065 |
| Antibody | ADI-30336 | ADI-30293 | ADI-30286 |
| EC50 | 1.274 | 1.624 | 0.3963 |
| Antibody | ADI-30288 | ADI-30278 | ADI-30306 |
| EC50 | 0.3844 | 0.1856 | 0.3984 |

Example 6. In Vivo Efficacy Assay in Animals

In this assay, the anti-tumor activity of the anti-TIGIT antibodies was investigated in a human TIGIT knock-in MC38 mouse tumor model.

The pharmacodynamics of candidate molecules ADI-30293 and ADI-30278 administered alone (10 mg/kg) to a human TIGIT knock-in MC38 mouse model were investigated. Mouse colon cancer MC38 cells (OBiO Technology (Shanghai) Co., Ltd., HYC0116) were grafted into female TIGIT transgenic mice (Biocytogen Beijing Co., Ltd.). Mice of each group were injected with antibodies subcutaneously on days 6, 10, 13 and 17 after grafting. Tumor volume was measured on days 6, 10, 13, 17, 21 and 25 after grafting, after which the mice were euthanized. The results are shown in FIG. 7.

Figure 7:
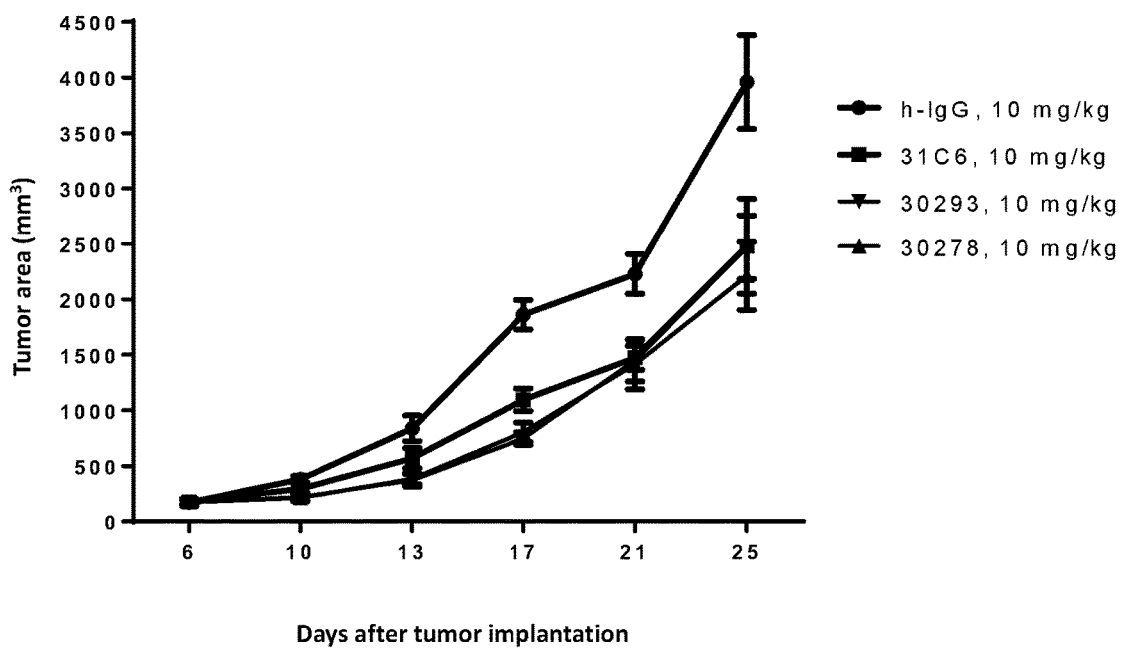
FIG. 7 shows pharmacodynamic studies of candidate molecules ADI-30293 and ADI-30278 administered alone (10 mg/kg) in a human TIGIT knock-in MC38 mouse model.

It can be seen from the results in FIG. 7 that the anti-TIGIT monoclonal antibodies ADI-30293 and ADI-30278 of the present invention have a certain inhibitory effect on the growth of tumor when used alone, compared to the negative control Ig4. The tumor inhibitory effect of the two candidate antibodies used alone was not significantly different from that of the positive control 31C6.

The pharmacodynamics of candidate molecules ADI-30293 and ADI-30278 administered (10+1 mg/kg) in combination with an anti-PD1 antibody (antibody C, WO2017133540A1) to the human TIGIT knock-in MC38 mouse model was further studied.

Mouse colon cancer cells MC38 (OBiO Technology (Shanghai) Co., Ltd., HYC0116) were cultivated in a DMEM medium. $1\times10^6$ MC38 cells in 0.2 mL of DMEM basal medium suspension were grafted to the right side of female TIGIT transgenic mice (SHANGHAI MODEL ORGANISMS). Tumor volume and body weight were measured twice a week throughout the study. Tumor length and width were measured using a vernier caliper on day 8 after tumor cell transplantation. The tumor volume was calculated according to the following formula: $\text{width}^2\times\text{length}/2$ ($\text{mm}^3$). Mice with an average tumor volume of about 71 $\text{mm}^3$ were randomly grouped with 6 mice per group and were euthanized when the tumor volume reached the detection endpoint or when the mice lost more than 20% of body weight. Mice of each group were injected subcutaneously with h-IgG (10 mg/kg), antibody C (1 mg/kg), and anti-TIGIT antibodies or isotype antibodies thereof (10 mg/kg), respectively, on days 8, 12, 15 and 19 after cell transplantation. The mean tumor volume at the endpoint was determined on day 29 after cell transplantation, after which the mice were euthanized. The results are shown in FIG. 8.

Figure 8A:
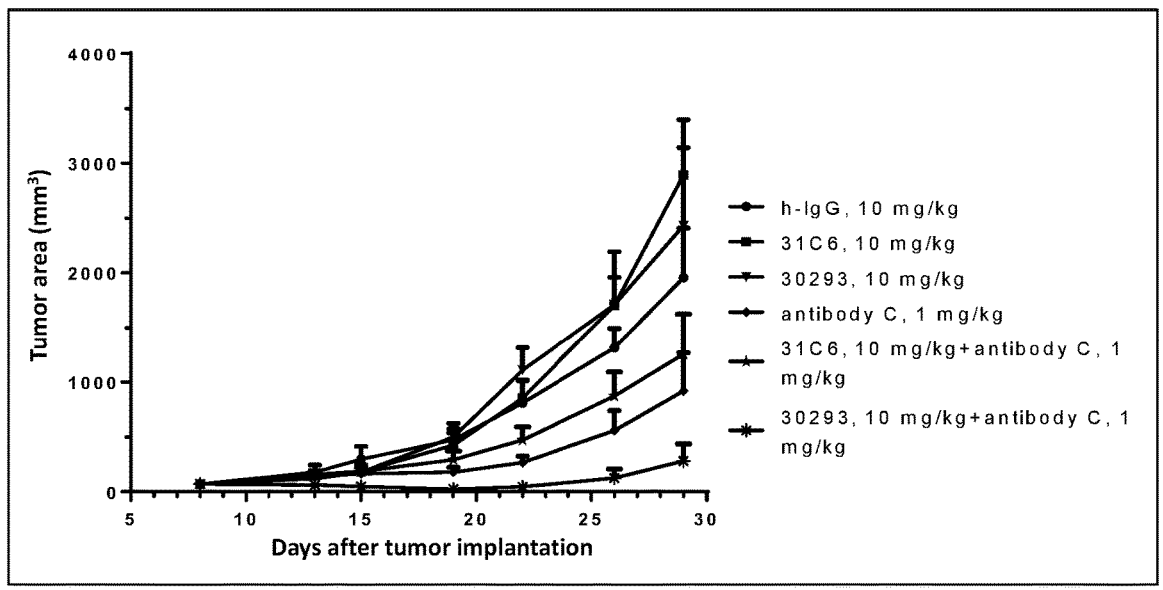
FIGS. 8A-B show pharmacodynamic studies of candidate molecules ADI-30293 and ADI-30278 administered (10+1 mg/kg) in combination with an anti-PD1 antibody (antibody C, WO 2017133540A1) in a human TIGIT knock-in MC38 mouse model.
Figure 8B:
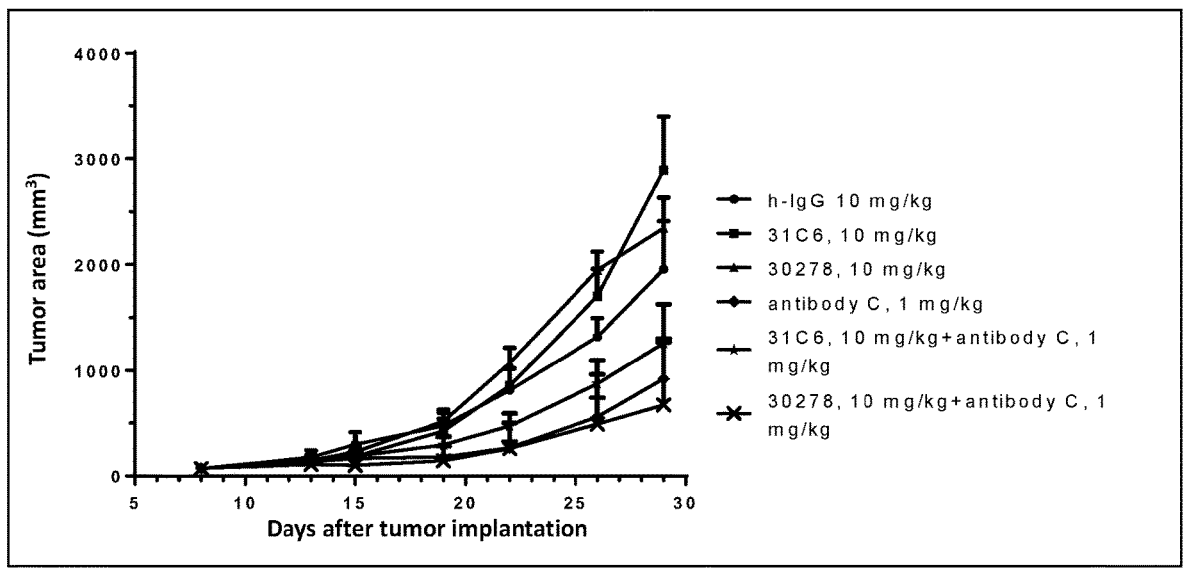

It can be seen from the results in FIG. 8 that the anti-TIGIT antibody (ADI-30293) used in combination with the anti-PD1 antibody (antibody C) shows a stronger tumor inhibitory effect than either of them used alone; and the combined effect of the ADI-30293 and the anti-PD1 antibody is better than that of the 31C6 and the anti-PD1 antibody. Likewise, the combined effect of the ADI-30278 and the anti-PD1 antibody was better than that of 31C6 and the anti-PD1 antibody (antibody C).

In this study, there was no significant change in body weight for mice of all groups on day 29 after grafting.

The invention claimed is:

1. An antibody or an antigen-binding fragment thereof that binds to TIGIT, comprising three heavy chain complementarity determining regions (HCDRs) and three light chain complementarity determining regions (LCDRs), wherein
   (a) HCDR1 comprises an amino acid sequence set forth in SEQ ID NOs: 1, 2, 3, 4, or 5, HCDR2 comprises an amino acid sequence set forth in SEQ ID NOs: 6, 7, 8, 9, or 10, HCDR3 comprises an amino acid sequence set forth in SEQ ID NOs: 11, 12, 13, 14, or 15, LCDR1 comprises an amino acid sequence set forth in SEQ ID NO: 16, LCDR2 comprises an amino acid sequence set forth in SEQ ID NO: 17, and LCDR3 comprises an amino acid sequence set forth in SEQ ID NO: 18;
   (b) HCDR1 comprises an amino acid sequence set forth in SEQ ID NOs: 19, 20, or 21, HCDR2 comprises an amino acid sequence set forth in SEQ ID NOs: 22, 23, or 24, HCDR3 comprises an amino acid sequence set forth in SEQ ID NO: 25, LCDR1 comprises an amino acid sequence set forth in SEQ ID NO: 26, LCDR2 comprises an amino acid sequence set forth in SEQ ID NO: 27, and LCDR3 comprises an amino acid sequence set forth in SEQ ID NOs: 28, 29, or 30;
   (c) HCDR1 comprises an amino acid sequence set forth in SEQ ID NOs: 31, 32, or 33, HCDR2 comprises an amino acid sequence set forth in SEQ ID NOs: 34, 35, 36, or 37, HCDR3 comprises an amino acid sequence set forth in SEQ ID NOs: 38, 39, or 40, LCDR1 comprises an amino acid sequence set forth in SEQ ID NO: 41, LCDR2 comprises an amino acid sequence set forth in SEQ ID NO: 42, and LCDR3 comprises an amino acid sequence set forth in SEQ ID NO: 43;
   (d) HCDR1 comprises an amino acid sequence set forth in SEQ ID NOs: 44, 45, 46, or 47, HCDR2 comprises an amino acid sequence set forth in SEQ ID NOs: 48, 49, 50, 51, or 52, HCDR3 comprises an amino acid sequence set forth in SEQ ID NOs: 53, 54, 55, or 56, LCDR1 comprises an amino acid sequence set forth in SEQ ID NO: 57, LCDR2 comprises an amino acid sequence set forth in SEQ ID NO: 58, and LCDR3 comprises an amino acid sequence set forth in SEQ ID NO: 59;
   (e) HCDR1 comprises an amino acid sequence set forth in SEQ ID NOs: 60, 61, or 62, HCDR2 comprises an amino acid sequence set forth in SEQ ID NOs: 6, 63, 64, or 65, HCDR3 comprises an amino acid sequence set forth in SEQ ID NOs: 66, 67, or 68, LCDR1 comprises an amino acid sequence set forth in SEQ ID NO: 69, LCDR2 comprises an amino acid sequence set forth in SEQ ID NO: 17, and LCDR3 comprises an amino acid sequence set forth in SEQ ID NO: 70;
   (f) HCDR1 comprises an amino acid sequence set forth in SEQ ID NOs: 71, 72, 73, or 74, HCDR2 comprises an amino acid sequence set forth in SEQ ID NOs: 22, 75, 76, or 77, HCDR3 comprises an amino acid sequence set forth in SEQ ID NOs: 78, 79, or 80, LCDR1 comprises an amino acid sequence set forth in SEQ ID NO: 81, LCDR2 comprises an amino acid sequence set forth in SEQ ID NO: 82, and LCDR3 comprises an amino acid sequence set forth in SEQ ID NO: 83;
   (g) HCDR1 comprises an amino acid sequence set forth in SEQ ID NOs: 178, 179, 180, or 181, HCDR2 comprises an amino acid sequence set forth in SEQ ID NOs: 6, 7, 8, or 9, HCDR3 comprises an amino acid sequence set forth in SEQ ID NOs: 182, 183, 184, or 185, LCDR1 comprises an amino acid sequence set forth in SEQ ID NO: 16, LCDR2 comprises an amino acid sequence set forth in SEQ ID NO: 17, and LCDR3 comprises an amino acid sequence set forth in SEQ ID NO: 18;
   (h) HCDR1 comprises an amino acid sequence set forth in SEQ ID NOs: 186 or 187, HCDR2 comprises an amino acid sequence set forth in SEQ ID NOs: 22 or 23, HCDR3 comprises an amino acid sequence set forth in SEQ ID NO: 188, LCDR1 comprises an amino acid sequence set forth in SEQ ID NO: 26, LCDR2 comprises an amino acid sequence set forth in SEQ ID NO: 27, and LCDR3 comprises an amino acid sequence set forth in SEQ ID NOs: 28 or 29;
   (i) HCDR1 comprises an amino acid sequence set forth in SEQ ID NOs: 189 or 190, HCDR2 comprises an amino acid sequence set forth in SEQ ID NOs: 34, 35 or 36, HCDR3 comprises an amino acid sequence set forth in SEQ ID NOs: 191 or 192, LCDR1 comprises an amino acid sequence set forth in SEQ ID NO: 41, LCDR2 comprises an amino acid sequence set forth in SEQ ID NO: 42, and LCDR3 comprises an amino acid sequence set forth in SEQ ID NO: 43;
   (j) HCDR1 comprises an amino acid sequence set forth in SEQ ID NOs: 193, 194, or 195, HCDR2 comprises an amino acid sequence set forth in SEQ ID NOs: 48, 49, 50, or 51, HCDR3 comprises an amino acid sequence set forth in SEQ ID NOs: 196, 197, or 198, LCDR1 comprises an amino acid sequence set forth in SEQ ID NO: 57, LCDR2 comprises an amino acid sequence set forth in SEQ ID NO: 58, and LCDR3 comprises an amino acid sequence set forth in SEQ ID NO: 59; (k) HCDR1 comprises an amino acid sequence set forth in SEQ ID NOs: 199 or 200, HCDR2 comprises an amino acid sequence set forth in SEQ ID NOs: 6, 63 or 64, HCDR3 comprises an amino acid sequence set forth in SEQ ID NOs: 201 or 202, LCDR1 comprises an amino acid sequence set forth in SEQ ID NO: 69, LCDR2 comprises an amino acid sequence set forth in SEQ ID NO: 17, and LCDR3 comprises an amino acid sequence set forth in SEQ ID NO: 70; or (1) HCDR1 comprises an amino acid sequence set forth in SEQ ID NOs: 203, 204, or 205, HCDR2 comprises an amino acid sequence set forth in SEQ ID NOs: 22, 75, or 76, HCDR3 comprises an amino acid sequence set forth in SEQ ID NOs: 206 or 207, LCDR1 comprises an amino acid sequence set forth in SEQ ID NO: 81, LCDR2 comprises an amino acid sequence set forth in SEQ ID NO: 82, and LCDR3 comprises an amino acid sequence set forth in SEQ ID NO: 83.

2. The antibody or the antigen-binding fragment thereof according to claim 1, comprising
(i) a heavy chain variable region comprising an amino acid sequence having at least 80%, 85%, or 90% sequence identity to an amino acid sequence set forth in SEQ ID NO: 84, 85, 86, or 87, and/or a light chain variable region comprising an amino acid sequence having at least 80%, 85%, or 90% sequence identity to an amino acid sequence set forth in SEQ ID NO: 104,
(ii) a heavy chain variable region comprising an amino acid sequence having at least 80%, 85%, or 90% sequence identity to an amino acid sequence set forth in SEQ ID NOs: 88, 89, or 90, and/or a light chain variable region comprising an amino acid sequence having at least 80%, 85%, or 90% sequence identity to an amino acid sequence set forth in SEQ ID NOs: 105 or 106,
(iii) a heavy chain variable region comprising an amino acid sequence having at least 80%, 85%, or 90% sequence identity to an amino acid sequence set forth in SEQ ID NOs: 91, 92, or 93, and/or a light chain variable region comprising an amino acid sequence having at least 80%, 85%, or 90% sequence identity to an amino acid sequence set forth in SEQ ID NO: 107,
(iv) a heavy chain variable region comprising an amino acid sequence having at least 80%, 85%, or 90% sequence identity to an amino acid sequence set forth in SEQ ID NOs: 94, 95, 96, or 97, and/or a light chain variable region comprising an amino acid sequence having at least 80%, 85%, or 90% sequence identity to an amino acid sequence set forth in SEQ ID NO: 108,
(v) a heavy chain variable region comprising an amino acid sequence having at least 80%, 85%, or 90% sequence identity to an amino acid sequence set forth in SEQ ID NOs: 98, 99, or 100, and/or a light chain variable region comprising an amino acid sequence having at least 80%, 85%, or 90% sequence identity to an amino acid sequence set forth in SEQ ID NO: 109, or
(vi) a heavy chain variable region comprising an amino acid sequence having at least 80%, 85%, or 90% sequence identity to an amino acid sequence set forth in SEQ ID NOs: 101, 102, or 103, and/or a light chain variable region comprising an amino acid sequence having at least 80%, 85%, or 90% sequence identity to an amino acid sequence set forth in SEQ ID NO: 110.

3. The antibody or the antigen-binding fragment thereof according to claim 1, comprising a heavy chain variable region and a light chain variable region selected from:
(i) a heavy chain variable region comprising an amino acid sequence set forth in SEQ ID NOs: 84, 85, 86, or 87, and a light chain variable region comprising an amino acid sequence set forth in SEQ ID NO: 104,
(ii) a heavy chain variable region comprising an amino acid sequence set forth in SEQ ID NOs: 88, 89, or 90, and a light chain variable region comprising an amino acid sequence set forth in SEQ ID NOs: 105 or 106,
(iii) a heavy chain variable region comprising an amino acid sequence set forth in SEQ ID NOs: 91, 92, or 93, and a light chain variable region comprising an amino acid sequence set forth in SEQ ID NO: 107,
(iv) a heavy chain variable region comprising an amino acid sequence set forth in SEQ ID NOs: 94, 95, 96, or 97, and a light chain variable region comprising an amino acid sequence set forth in SEQ ID NO: 108,
(v) a heavy chain variable region comprising an amino acid sequence set forth in SEQ ID NOs: 98, 99, or 100, and a light chain variable region comprising an amino acid sequence set forth in SEQ ID NO: 109, or (iv) a heavy chain variable region comprising an amino acid sequence set forth in SEQ ID NOs: 101, 102, or 103, and a light chain variable region comprising an amino acid sequence set forth in SEQ ID NO: 110.

4. The antibody or the antigen-binding fragment thereof according to claim 1, wherein the antibody is an antibody in the form of IgG1, IgG2, or IgG4, or an antigen-binding fragment thereof, optionally wherein the antibody has an IgG4 Fc region comprising S228P, F234A, and L235A mutations.

5. The antibody or the antigen-binding fragment thereof according to claim 1, wherein the antibody is a fully humanized antibody, a humanized antibody, or a chimeric antibody.

6. The antibody or the antigen-binding fragment thereof according to claim 1, wherein the antigen-binding fragment is an antibody fragment selected from: Fab, Fab', Fab'-SH, Fv, single chain antibody scFv, (Fab')$_2$ fragment, diabody (dAb), or linear antibody.

7. The antibody or the antigen-binding fragment thereof according to claim 1, wherein the antibody has one or more of the following properties:
(i) capacity of binding to human TIGIT with high affinity;
(ii) activity of cross-immunoreaction with monkey and/or murine TIGIT;
(iii) effectively binding to TIGIT on cell surface;
(iv) blocking the binding of TIGIT to its ligand CD155;
(v) relieving the inhibitory effect of binding of TIGIT to CD155 on a downstream IL-2 signaling pathway;
(vi) increasing IL-2 production in T cells;
(vii) anti-tumor activity; and
(viii) having better tumor inhibitory effect in combination with anti-PD-1 antibody.

8. An isolated nucleic acid encoding the anti-TIGIT antibody or the antigen-binding fragment thereof according to claim 1.

9. A vector comprising a nucleic acid encoding the anti-TIGIT antibody or the antigen-binding fragment thereof according to claim 1, optionally wherein the vector is an expression vector.

10. A host cell comprising a nucleic acid encoding the anti-TIGIT antibody or the antigen-binding fragment thereof according to claim 1, optionally wherein the host cell is prokaryotic or eukaryotic, further optionally wherein the host cell is a yeast cell or mammalian cell, and further optionally wherein the host cell is a 293 cell or a CHO cell.

11. A method for preparing an anti-TIGIT antibody or an antigen-binding fragment thereof according to claim 1, the method comprising cultivating a host cell comprising a nucleic acid encoding the anti-TIGIT antibody or the antigen-binding fragment thereof under conditions suitable for expressing the nucleic acid, and optionally isolating the antibody or the antigen-binding fragment thereof, wherein optionally, the method further comprises isolating the anti-TIGIT antibody or the antigen-binding fragment thereof from the host cell.

12. An immunoconjugate comprising the antibody or the antigen-binding fragment thereof according to claim 1 conjugated to a therapeutic or diagnostic agent.

13. A multispecific antibody comprising the antibody or the antigen-binding fragment thereof according to claim 1, wherein, optionally, the multispecific antibody is a bispecific antibody.

14. A pharmaceutical composition comprising the antibody or the antigen-binding fragment thereof according to claim 1, and optionally a pharmaceutical adjuvant.

15. The pharmaceutical composition according to claim 14, comprising the antibody or the antigen-binding fragment thereof and an anti-PD-1 antibody.

16. The pharmaceutical composition according to claim 14, comprising a second therapeutic agent.

17. A method for preventing or treating a tumor or a viral infectious disease in a subject, comprising: administering to the subject an effective amount of the anti-TIGIT antibody or the antigen-binding fragment thereof according to claim 1, wherein, optionally, the tumor is a gastrointestinal cancer, further optionally, wherein the tumor is a colon cancer.

18. The method according to claim 17, wherein the anti-TIGIT antibody or the antigen-binding fragment thereof is in combination with an anti-PD-1 anti antibody.

19. A method for blocking binding of TIGIT to CD155 so as to reduce or eliminate the immunosuppressive effect of TIGIT in a subject, the method comprising: administering to the subject an effective amount of the anti-TIGIT antibody or the antigen-binding fragment thereof according to claim 1.

20. A method for detecting TIGIT in a sample, the method comprising:
 (a) contacting the sample with the antibody or the antigen-binding fragment thereof according to claim 1; and
 (b) detecting a complex formed by the antibody or the antigen-binding fragment and TIGIT, wherein, optionally, the antibody is detectably labeled.

21. The antibody or the antigen-binding fragment thereof according to claim 1, comprising:
 HCDR1 comprising an amino acid sequence set forth in SEQ ID NO: 200,
 HCDR2 comprising an amino acid sequence set forth in SEQ ID NO: 64,
 HCDR3 comprising an amino acid sequence set forth in SEQ ID NO: 202,
 LCDR1 comprising an amino acid sequence set forth in SEQ ID NO: 69,
 LCDR2 comprising an amino acid sequence set forth in SEQ ID NO: 17, and
 LCDR3 comprising an amino acid sequence set forth in SEQ ID NO: 70.

22. The antibody or the antigen-binding fragment thereof according to claim 1, comprising:
 HCDR1 comprising an amino acid sequence set forth in SEQ ID NO: 189,
 HCDR2 comprising an amino acid sequence set forth in SEQ ID NO: 35,
 HCDR3 comprising an amino acid sequence set forth in SEQ ID NO: 191,
 LCDR1 comprising an amino acid sequence set forth in SEQ ID NO: 41,
 LCDR2 comprising an amino acid sequence set forth in SEQ ID NO: 42, and
 LCDR3 comprising an amino acid sequence set forth in SEQ ID NO: 43.

* * * * *